United States Patent
Kawamura et al.

(10) Patent No.: US 10,862,049 B2
(45) Date of Patent: Dec. 8, 2020

(54) COMPOSITION, ORGANIC-ELECTROLUMINESCENCE-DEVICE MATERIAL, COMPOSITION FILM, ORGANIC ELECTROLUMINESCENCE DEVICE, AND ELECTRONIC DEVICE

(71) Applicant: IDEMITSU KOSAN CO., LTD., Tokyo (JP)

(72) Inventors: Masahiro Kawamura, Sodegaura (JP); Hiroyuki Iwabuchi, Sodegaura (JP); Tetsuya Masuda, Sodegaura (JP); Hitoshi Kuma, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 313 days.

(21) Appl. No.: 15/928,636

(22) Filed: Mar. 22, 2018

(65) Prior Publication Data

US 2018/0277769 A1 Sep. 27, 2018

(30) Foreign Application Priority Data

Mar. 24, 2017 (JP) .................................. 2017-060034

(51) Int. Cl.
*H01L 51/00* (2006.01)
*C09K 11/06* (2006.01)
*C07D 403/14* (2006.01)
*C07D 209/86* (2006.01)
*H01L 51/50* (2006.01)

(52) U.S. Cl.
CPC ........ *H01L 51/0072* (2013.01); *C07D 209/86* (2013.01); *C07D 403/14* (2013.01);
(Continued)

(58) Field of Classification Search
None
See application file for complete search history.

(56) References Cited

U.S. PATENT DOCUMENTS

2012/0211736 A1* 8/2012 Kim ................. C09K 11/06
257/40

2013/0234119 A1* 9/2013 Mizuki ............... H01L 51/0072
257/40
2014/0110692 A1* 4/2014 Kato .................. H01L 51/0072
257/40

FOREIGN PATENT DOCUMENTS

WO WO-2011/132684 A1 10/2011
WO WO-2013/145923 A1 3/2013
WO WO-2013/084885 A1 6/2013

* cited by examiner

*Primary Examiner* — Robert S Loewe

(74) *Attorney, Agent, or Firm* — Foley & Lardner LLP

(57) ABSTRACT

A composition contains a mixture of at least two compounds, the at least two compounds containing a first compound represented by a formula (1) and a second compound represented by a formula (2). In the formula (1), $R^1$ to $R^4$, $A^1$ and $A^2$ include five cyclic structures in total each represented by a formula (1a) below. In the formula (2), one of $A^3$ and $A^4$ is a substituent represented by a formula (2a), and the other thereof is represented by a formula (2b).

(1)

(1a)

(Continued)

-continued
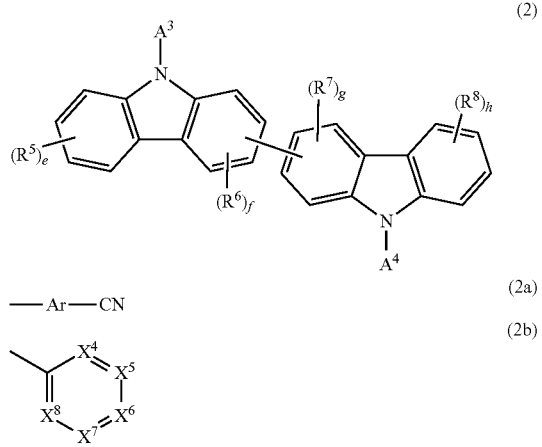
(2)
—Ar—CN   (2a)
(2b)
28 Claims, 1 Drawing Sheet
(52) U.S. Cl.
CPC .......... *C09K 11/06* (2013.01); *H01L 51/0052* (2013.01); *H01L 51/0067* (2013.01); *C09K 2211/1018* (2013.01); *C09K 2211/1029* (2013.01); *C09K 2211/185* (2013.01); *H01L 51/0085* (2013.01); *H01L 51/5016* (2013.01); *H01L 51/5056* (2013.01); *H01L 51/5072* (2013.01); *H01L 51/5096* (2013.01); *H01L 2251/5384* (2013.01)

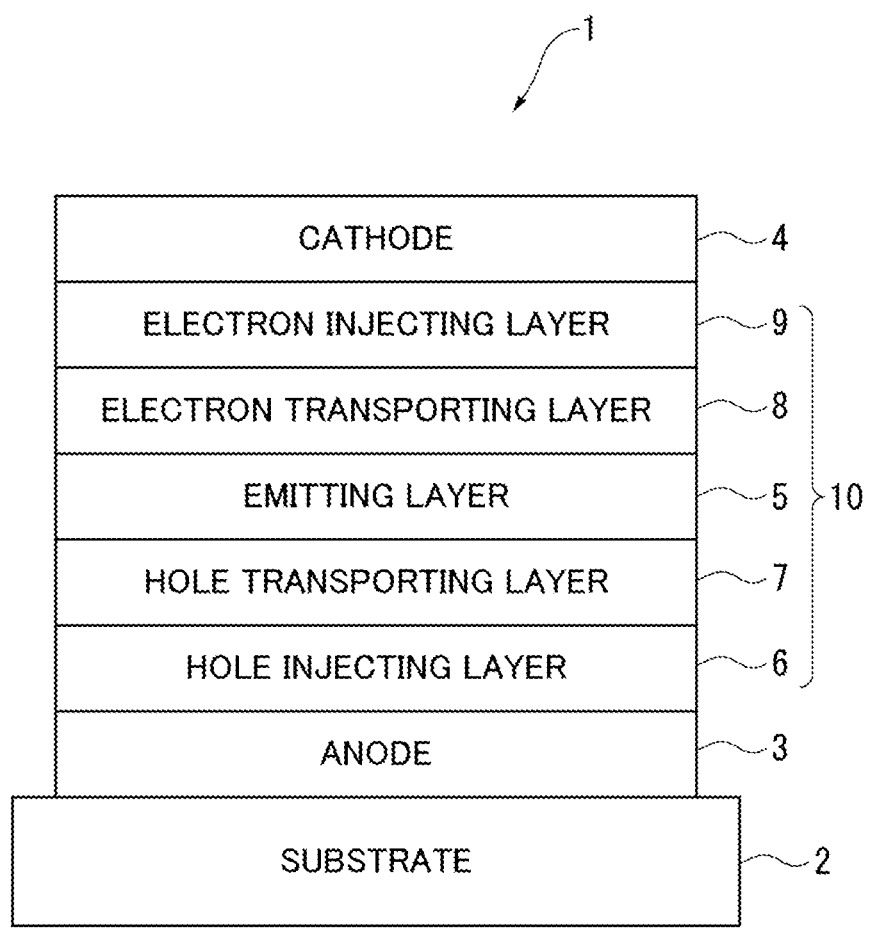

COMPOSITION, ORGANIC-ELECTROLUMINESCENCE-DEVICE MATERIAL, COMPOSITION FILM, ORGANIC ELECTROLUMINESCENCE DEVICE, AND ELECTRONIC DEVICE

CROSS-REFERENCE TO RELATED APPLICATION

This application claims priority to Japanese Patent Application No. 2017-060034, filed Mar. 24, 2017, the disclosure of which is hereby incorporated by reference in its entirety.

TECHNICAL FIELD

The present invention relates to a composition, a material for an organic electroluminescence device (also referred to as an organic-electroluminescence-device material), a composition film, an organic electroluminescence device, and an electronic device.

BACKGROUND ART

Patent Literature 1 (International Publication No. WO2013/084885) and Patent Literature 2 (International Publication No. WO2013/145923) each disclose an organic electroluminescence device including a first host that is a biscarbazole derivative in a specific structure having a cyano group and a second host that is a compound having both a carbazolyl derivative structure and a nitrogen-containing hetero aromatic ring. Patent Literatures 1 and 2 each disclose that the organic electroluminescence device has a long lifetime.

When two materials (e.g., the first host and the second host) are respectively evaporated from different evaporation sources, a manufacturing process of the organic electroluminescence device becomes complicated. However, an organic electroluminescence device including a single material (e.g., only one of the first host and the second host) exhibits a shorter lifetime. For this reason, a technique of stably evaporating two materials (or a plurality of materials) from a single evaporation source is desired.

In Patent Literatures 1 and 2, when two host materials that is a combination of the first host and the second host are evaporated from a single evaporation source, an organic electroluminescence device including a layer formed at an initial stage of evaporation exhibits a favorable performance. However, when the evaporation from the same evaporation source continues for a long time, as an evaporation time passes, a ratio between the first host and the second host contained in the formed layer becomes unstable, resulting in an unstable performance of the organic electroluminescence device.

SUMMARY OF THE INVENTION

An object of the invention is to provide a composition capable of being evaporated from a single evaporation source at a stable material ratio while maintaining a performance of an organic electroluminescence device, to provide an organic-electroluminescence-device material containing the composition, to provide a composition film containing the composition, to provide an organic electroluminescence device containing the composition, and to provide an electronic device provided with the organic electroluminescence device.

In an aspect of the invention, a composition contains a mixture of at least two compounds, the at least two compounds including a first compound represented by a formula (1) and a second compound represented by a formula (2).

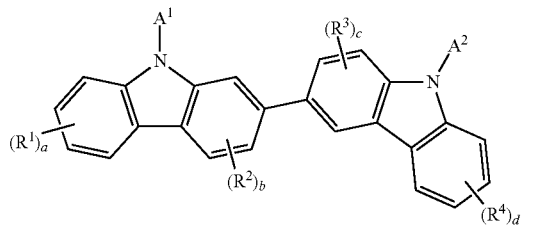

(1)

In the formula (1), $R^1$ to $R^4$ each independently represent a halogen atom, a substituted or unsubstituted alkyl group having 1 to 25 carbon atoms, a substituted or unsubstituted cycloalkyl group having 3 to 25 ring carbon atoms, a substituted or unsubstituted aryl group having 6 to 18 ring carbon atoms, a substituted or unsubstituted heterocyclic group having 6 to 18 ring atoms, a silyl group substituted by at least one group selected from the group consisting of an alkyl group having 1 to 25 carbon atoms and an aryl group having 6 to 18 ring carbon atoms, or a cyano group.

a is 0, 1, 2, 3 or 4.
b is 0, 1, 2 or 3.
c is 0, 1, 2 or 3.
d is 0, 1, 2, 3 or 4.
A plurality of $R^1$ are mutually the same or different when a is 2 or more.
A plurality of $R^2$ are mutually the same or different when b is 2 or more.
A plurality of $R^3$ are mutually the same or different when c is 2 or more.
A plurality of $R^4$ are mutually the same or different when d is 2 or more.
$A^1$ and $A^2$ each independently represent a substituted or unsubstituted aryl group having 6 to 24 ring carbon atoms, or a substituted or unsubstituted heterocyclic group having 6 to 24 ring atoms.
$R^1$ to $R^4$, $A^1$ and $A^2$ include five cyclic structures in total each represented by a formula (1a) below.

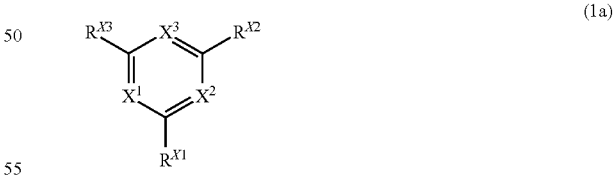

(1a)

In the formula (1a), $X^1$, $X^2$ and $X^3$ each independently represent $CR^X$ or a nitrogen atom. In at least one cyclic structure of the five cyclic structures each represented by the formula (1a), at least one of $X^1$, $X^2$ and $X^3$ is a nitrogen atom. The cyclic structures each represented by the formula (1a) are bonded to each other to form a fused ring, or are not bonded.

$R^X$, $R^{X1}$, $R^{X2}$ and $R^{X3}$ each independently represent a single bond, a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

When a plurality of $R^X$ are present, the plurality of $R^X$ are mutually the same or different.

At least one of $R^{X1}$, $R^{X2}$, $R^{X3}$ and one or more $R^X$ is a single bond.

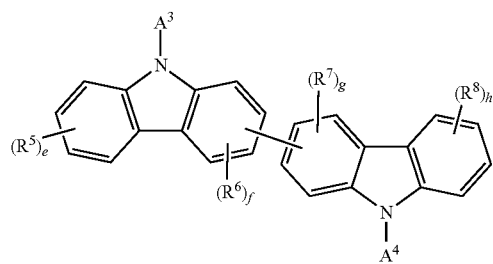

(2)

In the formula (2), $R^5$ to $R^8$ each independently represent: a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

e is 0, 1, 2, 3 or 4.
f is 0, 1, 2 or 3.
g is 0, 1, 2 or 3.
h is 0, 1, 2, 3 or 4.

A plurality of $R^5$ are mutually the same or different when e is 2 or more.

A plurality of $R^6$ are mutually the same or different when f is 2 or more.

A plurality of $R^7$ are mutually the same or different when g is 2 or more.

A plurality of $R^8$ are mutually the same or different when h is 2 or more.

One of $A^3$ and $A^4$ is a substituent represented by a formula (2a), and the other of $A^3$ and $A^4$ is represented by a formula (2b).

—Ar—CN    (2a)

In the formula (2a), Ar represents a substituted or unsubstituted phenanthrylene group.

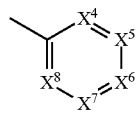

(2b)

In the formula (2b), $X^4$, $X^5$, $X^6$, $X^7$ and $X^8$ each independently represent $CR^Y$ or a nitrogen atom. $R^Y$ represents a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

A plurality of $R^Y$ are mutually the same or different.

According to another aspect of the invention, an organic-electroluminescence-device material containing the composition according to the above aspect of the invention is provided.

According to still another aspect of the invention, a composition film containing the composition according to the above aspect of the invention is provided.

According to a further aspect of the invention, an organic EL device including: an anode; a cathode; and at least one organic layer provided between the anode and the cathode, in which the at least one organic layer includes the composition according to the above aspect of the invention, is provided.

According to a still further aspect of the invention, an electronic device including the organic electroluminescence device according to the above aspect of the invention is provided.

The above aspects of the invention allows to provide a composition capable of being evaporated from a single evaporation source at a stable material ratio while maintaining a performance of an organic electroluminescence device, to provide an organic-electroluminescence-device material containing the composition, to provide a composition film containing the composition, to provide an organic electroluminescence device containing the composition, and to provide an electronic device including the organic electroluminescence device.

BRIEF DESCRIPTION OF DRAWING(S)

FIGURE schematically shows an exemplary arrangement of an organic electroluminescence device according to an exemplary embodiment of the invention.

DESCRIPTION OF EMBODIMENT(S)

First Exemplary Embodiment

Composition

A composition according to a first exemplary embodiment of the invention is a composition in a mixture of at least two compounds.

The composition of the exemplary embodiment at least contains a first compound represented by a formula (1) below and a second compound represented by a formula (2) below.

The composition of the exemplary embodiment may be in any forms. Examples of the forms of the composition of the exemplary embodiment include solid, powder, a solution and a film. When the composition of the exemplary embodiment is solid, the composition may be pelletized.

First Compound

The first compound is represented by the formula (1) below.

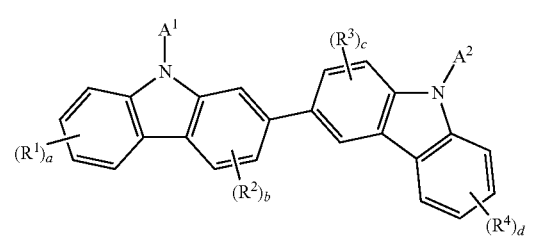

(1)

In the formula (1), $R^1$ to $R^4$ each independently represent a halogen atom, a substituted or unsubstituted alkyl group having 1 to 25 carbon atoms, a substituted or unsubstituted cycloalkyl group having 3 to 25 ring carbon atoms, a substituted or unsubstituted aryl group having 6 to 18 ring carbon atoms, a substituted or unsubstituted heterocyclic group having 6 to 18 ring atoms, a silyl group substituted by at least one group selected from the group consisting of an alkyl group having 1 to 25 carbon atoms and an aryl group having 6 to 18 ring carbon atoms, or a cyano group.

a is 0, 1, 2, 3 or 4.
b is 0, 1, 2 or 3.
c is 0, 1, 2 or 3.
d is 0, 1, 2, 3 or 4.

A plurality of $R^1$ are mutually the same or different when a is 2 or more.

A plurality of $R^2$ are mutually the same or different when b is 2 or more.

A plurality of $R^3$ are mutually the same or different when c is 2 or more.

A plurality of $R^4$ are mutually the same or different when d is 2 or more.

$A^1$ and $A^2$ each independently represent a substituted or unsubstituted aryl group having 6 to 24 ring carbon atoms, or a substituted or unsubstituted heterocyclic group having 6 to 24 ring atoms.

$R^1$ to $R^4$, $A^1$ and $A^2$ include five cyclic structures in total each represented by a formula (1a) below.

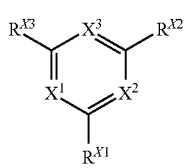

(1a)

In the formula (1a), $X^1$, $X^2$ and $X^3$ each independently represent $CR^X$ or a nitrogen atom. In at least one cyclic structure of the five cyclic structures each represented by the formula (1a), at least one of $X^1$, $X^2$ and $X^3$ is a nitrogen atom. The cyclic structures represented by the formula (1a) are bonded to each other to form a fused ring, or are not bonded.

$R^X$, $R^{X1}$, $R^{X2}$ and $R^{X3}$ each independently represent a single bond, a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

When a plurality of $R^X$ are present, the plurality of $R^X$ may be mutually the same or different.

At least one of $R^{X1}$, $R^{X2}$, $R^{X3}$ and one or more $R^X$ is a single bond.

Herein, that "$R^1$ to $R^4$, $A^1$ and $A^2$ include five cyclic structures in total each represented by the formula (1a)" means that $R^1$ to $R^4$, $A^1$ and $A^2$ include five six-membered rings each represented by the formula (1a). The five six-membered rings each represented by the formula (1a) are mutually the same or different.

When the cyclic structures each represented by the formula (1a) are bonded to each other to form a fused ring, the number of the six-membered ring forming the fused ring is counted in the five six-membered rings included in $R^1$ to $R^4$, $A^1$ and $A^2$. In this arrangement, for instance, when the cyclic structures each represented by the formula (1a) are bonded to each other to form a fused ring represented by a formula (1b), the fused ring includes two six-membered rings.

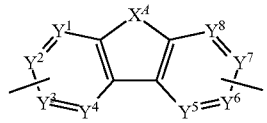

(1b)

In the formula (1b), $X^A$ represents $CR^{101}R^{102}$, $NR^{103}$, an oxygen atom, or a sulfur atom.

$R^{101}$ to $R^{103}$ each independently represent a substituted or unsubstituted alkyl group having 1 to 25 carbon atoms, or a substituted or unsubstituted cycloalkyl group having 3 to 25 ring carbon atoms.

$Y^1$ to $Y^8$ each independently represent $CR^X$ or a nitrogen atom.

$R^X$ represents a single bond, a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

When a plurality of $R^X$ are present, the plurality of $R^X$ may be mutually the same or different.

At least one of the plurality of $R^X$ is a single bond.

In the first compound, a, b, c and d are preferably 0.

When a, b, c and d are 0 in the formula (1), the first compound is represented by a formula (1A) below.

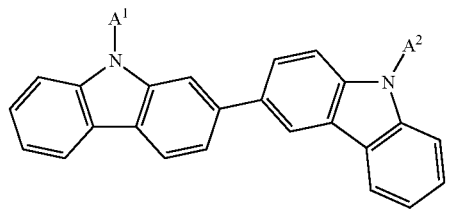

(1A)

In the formula (1A), $A^1$ and $A^2$ each independently represent a substituted or unsubstituted aryl group having 6 to 24 ring carbon atoms, or a substituted or unsubstituted heterocyclic group having 6 to 24 ring atoms.

$A^1$ and $A^2$ include five cyclic structures in total each represented by the formula (1a).

The first compound is preferably a compound represented by a formula (3).

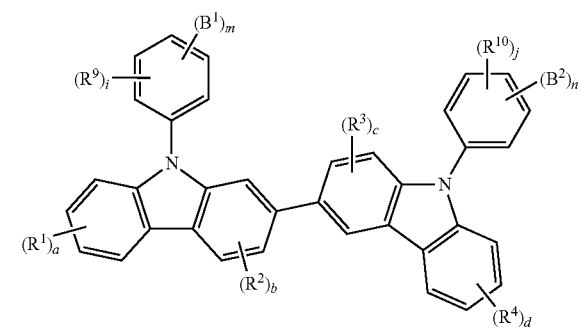

(3)

In the formula (3), $R^1$ to $R^4$, $R^9$ and $R^{10}$ each independently represent a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

a is 0, 1, 2, 3 or 4.
b is 0, 1, 2 or 3.
c is 0, 1, 2 or 3.
d is 0, 1, 2, 3 or 4.
i is 0, 1, 2, 3, 4 or 5.
j is 0, 1, 2, 3, 4 or 5.

A plurality of $R^1$ are mutually the same or different when a is 2 or more.

A plurality of $R^2$ are mutually the same or different when b is 2 or more.

A plurality of $R^3$ are mutually the same or different when c is 2 or more.

A plurality of $R^4$ are mutually the same or different when d is 2 or more.

A plurality of $R^9$ are mutually the same or different when i is 2 or more.

A plurality of $R^{10}$ are mutually the same or different when j is 2 or more.

$B^1$ and $B^2$ each independently represent a substituent represented by a formula (4) below.

m is 0 or 1.
n is 0 or 1.
m+n=1

(4)

In the formula (4), $X^1$ to $X^3$ represent $CR^Z$ or a nitrogen atom.

$R^Z$ represents a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

A plurality of $R^Z$ are mutually the same or different.

$R^{11}$ and $R^{12}$ each independently represent a halogen atom, a substituted or unsubstituted alkyl group having 1 to 25 carbon atoms, a substituted or unsubstituted cycloalkyl group having 3 to 25 ring carbon atoms, or a cyano group.

k is 0, 1, 2, 3, 4 or 5.
l is 0, 1, 2, 3, 4 or 5.

A plurality of $R^{11}$ are mutually the same or different when k is 2 or more.

A plurality of $R^{12}$ are mutually the same or different when l is 2 or more.

When a, b, c and d are 0 in the formula (3), the first compound is represented by a formula (3A) below.

(3A)

In the formula (3A), $R^9$ and $R^{10}$ each independently represent a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

i is 0, 1, 2, 3, 4 or 5.
j is 0, 1, 2, 3, 4 or 5.

A plurality of $R^9$ are mutually the same or different when i is 2 or more.

A plurality of $R^{10}$ are mutually the same or different when j is 2 or more.

$B^1$ and $B^2$ each independently represent a substituent represented by a formula (4) below.

m is 0 or 1.
n is 0 or 1.
m+n=1

In the first compound, a, b, c, d, i and j are preferably 0.

When a, b, c, d, i and j are 0 in the formula (3), the first compound is represented by a formula (3B) below.

(3B)

In the formula (3B), $B^1$ and $B^2$ each independently represent a substituent represented by a formula (4) below.

m is 0 or 1.
n is 0 or 1.
m+n=1

In the first compound, two or three of $X^1$, $X^2$ and $X^3$ are preferably nitrogen atoms and, more preferably, $X^1$, $X^2$ and $X^3$ are nitrogen atoms.

In the first compound, it is also preferable that $X^1$ and $X^3$ are nitrogen atoms and $X^2$ is $CR^Z$.

In the first compound, it is preferable that m is 1 and n is 0.

When m is 1 and n is 0 in the formula (3), the first compound is represented by a formula (3C) below.

(3C)

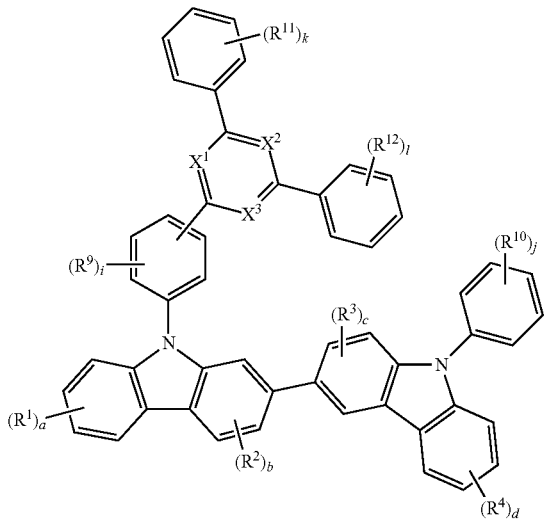

In the formula (3C), $R^1$ to $R^4$, $R^9$ and $R^{10}$ each independently represent a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

a is 0, 1, 2, 3 or 4.
b is 0, 1, 2 or 3.
c is 0, 1, 2 or 3.
d is 0, 1, 2, 3 or 4.
i is 0, 1, 2, 3 or 4.
j is 0, 1, 2, 3, 4 or 5.

A plurality of $R^1$ are mutually the same or different when a is 2 or more.
A plurality of $R^2$ are mutually the same or different when b is 2 or more.
A plurality of $R^3$ are mutually the same or different when c is 2 or more.
A plurality of $R^4$ are mutually the same or different when d is 2 or more.
A plurality of $R^9$ are mutually the same or different when i is 2 or more.
A plurality of $R^{10}$ are mutually the same or different when j is 2 or more.

$X^1$ to $X^3$ represent $CR^Z$ or a nitrogen atom.

$R^Z$ represents a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

A plurality of $R^Z$ are mutually the same or different.

$R^{11}$ and $R^{12}$ each independently represent a halogen atom, a substituted or unsubstituted alkyl group having 1 to 25 carbon atoms, a substituted or unsubstituted cycloalkyl group having 3 to 25 ring carbon atoms, or a cyano group.

k is 0, 1, 2, 3, 4 or 5.
l is 0, 1, 2, 3, 4 or 5.

A plurality of $R^{11}$ are mutually the same or different when k is 2 or more.
A plurality of $R^{12}$ are mutually the same or different when l is 2 or more.

In the first compound, it is also preferable that $A^1$ or $A^2$ is represented by a formula (4A) below.

(4A)

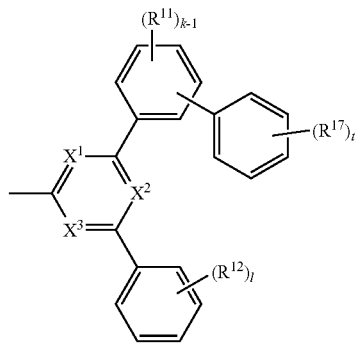

In the formula (4A), $X^1$ to $X^3$ represent $CR^Z$ or a nitrogen atom.

$R^Z$ represents a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

A plurality of $R^Z$ are mutually the same or different.

$R^{11}$, $R^{12}$ and $R^{17}$ each independently represent a halogen atom, a substituted or unsubstituted alkyl group having 1 to 25 carbon atoms, a substituted or unsubstituted cycloalkyl group having 3 to 25 ring carbon atoms, or a cyano group.

k is 1, 2, 3, 4 or 5.
l is 0, 1, 2, 3, 4 or 5.
t is 0, 1, 2, 3, 4 or 5.

A plurality of $R^{11}$ are mutually the same or different when k is 3 or more (i.e., (k−1) is equal to or more than 2).
A plurality of $R^{12}$ are mutually the same or different when l is 2 or more.
A plurality of $R^{17}$ are mutually the same or different when t is 2 or more.

In the first compound, it is also preferable that $A^1$ or $A^2$ is represented by a formula (4B) below.

(4B)

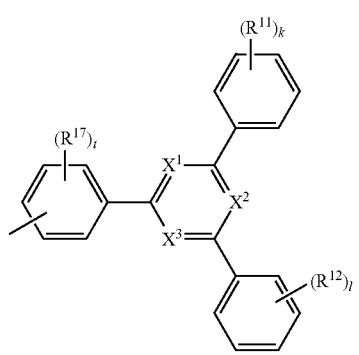

In the formula (4B), $X^1$ to $X^3$ represent $CR^Z$ or a nitrogen atom.

$R^Z$ represents a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

A plurality of $R^Z$ are mutually the same or different.

$R^{11}$, $R^{12}$ and $R^{17}$ each independently represent a halogen atom, a substituted or unsubstituted alkyl group having 1 to 25 carbon atoms, a substituted or unsubstituted cycloalkyl group having 3 to 25 ring carbon atoms, or a cyano group.

k is 0, 1, 2, 3, 4 or 5.

l is 0, 1, 2, 3, 4 or 5.

t is 0, 1, 2, 3 or 4.

A plurality of $R^{11}$ are mutually the same or different when k is 2 or more.

A plurality of $R^{12}$ are mutually the same or different when l is 2 or more.

A plurality of $R^{17}$ are mutually the same or different when t is 2 or more.

In the first compound, it is preferable that $R^1$ to $R^4$ each independently represent a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

The first compound can be manufactured by a combination of known methods (e.g., International Publication No. WO2011/132684).

Examples of the first compound according to the exemplary embodiment are given below. It should be noted that the first compound in the exemplary embodiment are by no means limited to the examples below.

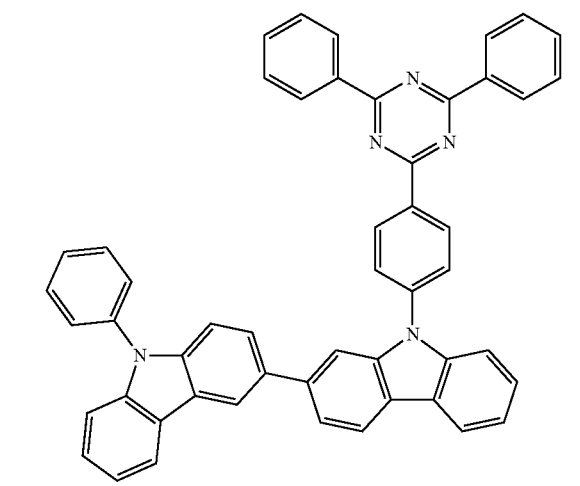

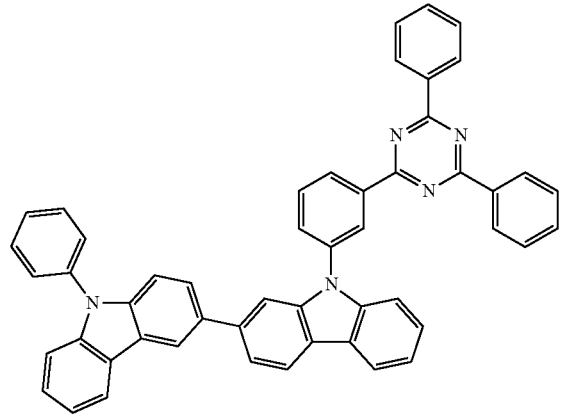

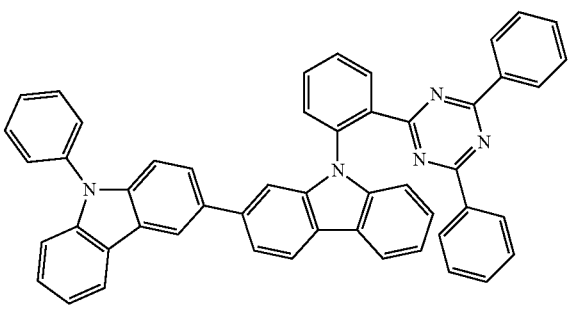

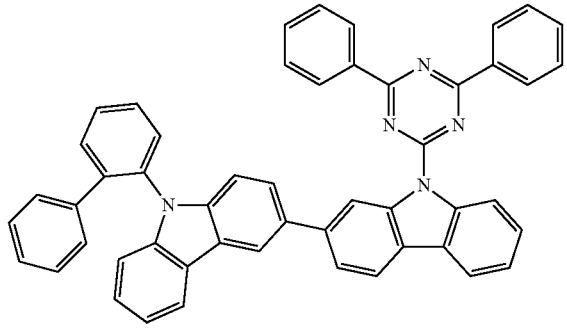

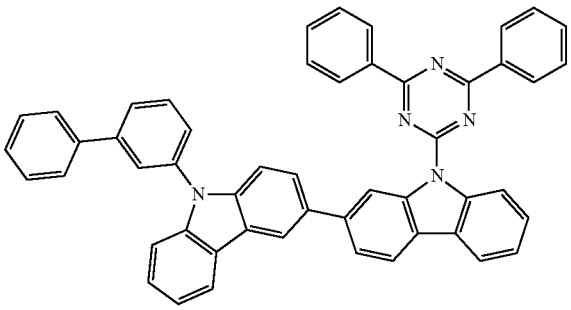

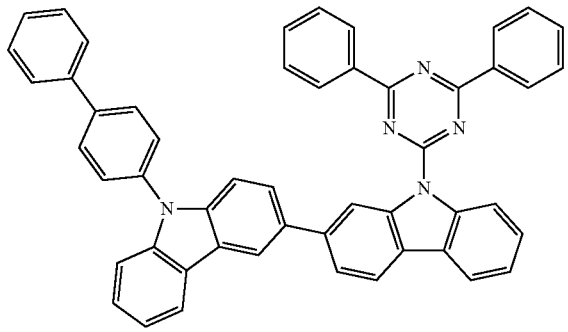

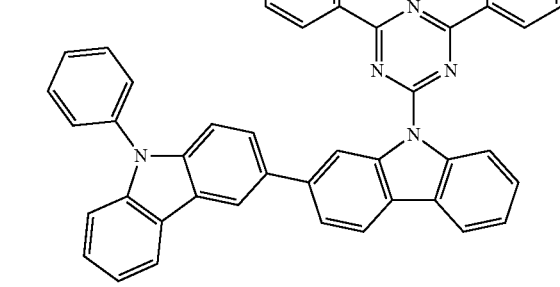

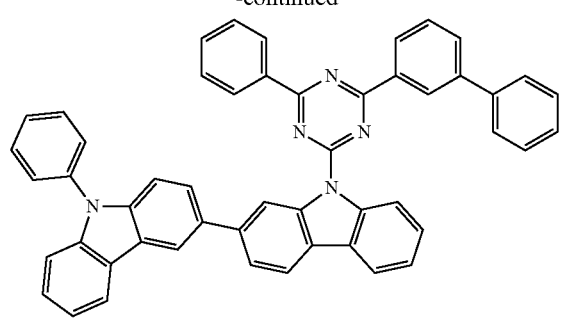
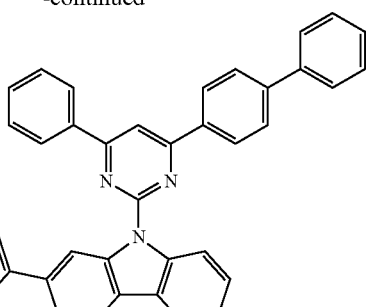
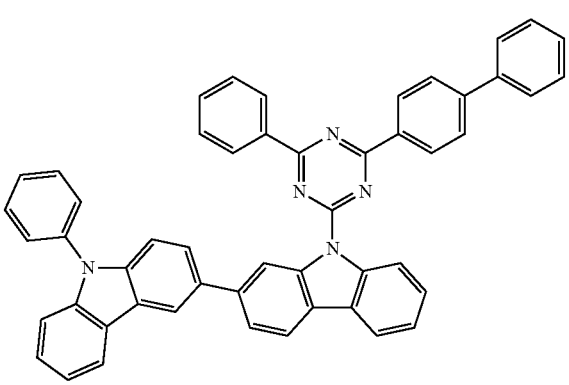
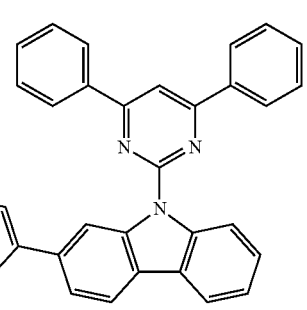
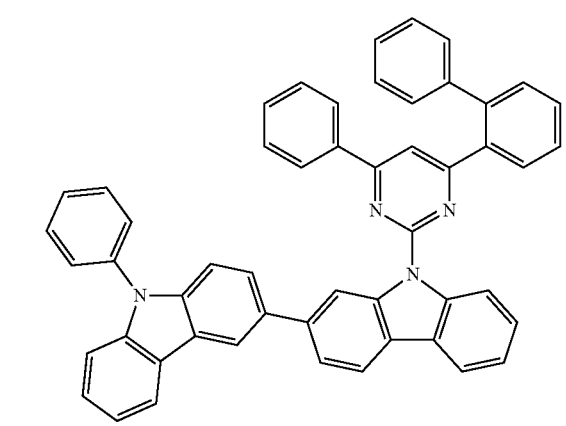
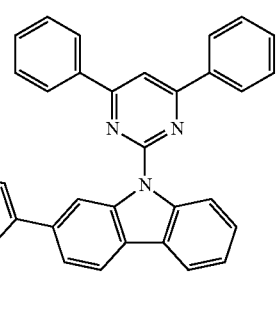
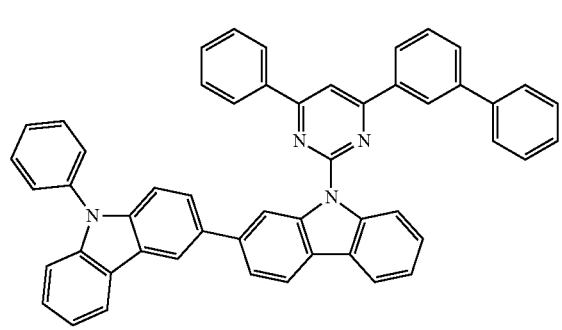
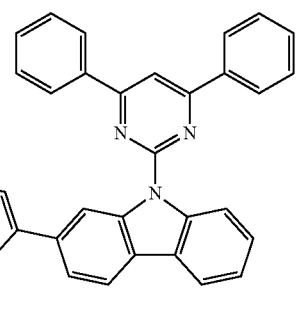

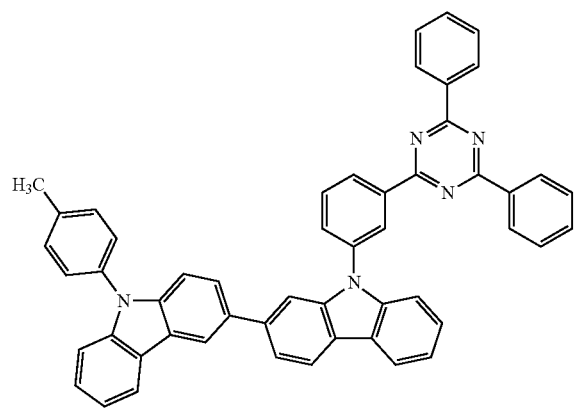
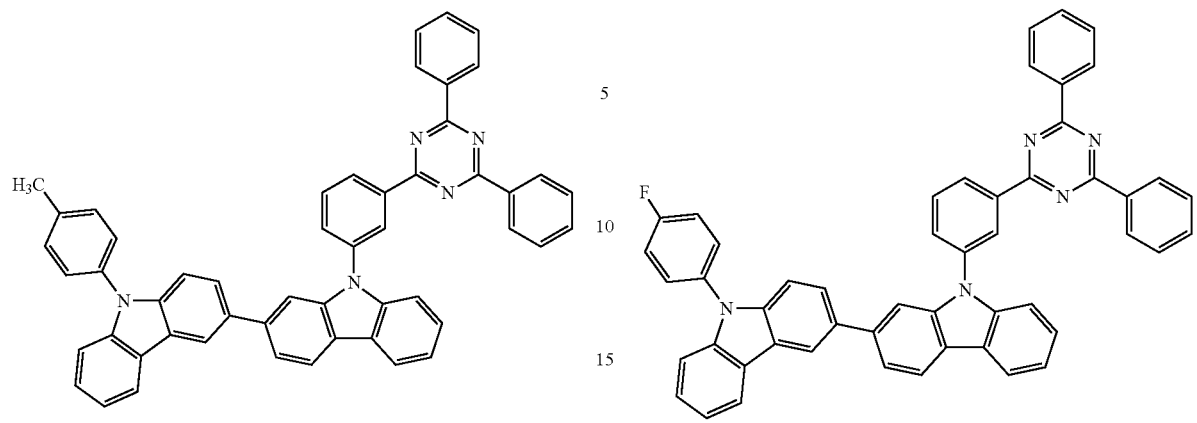
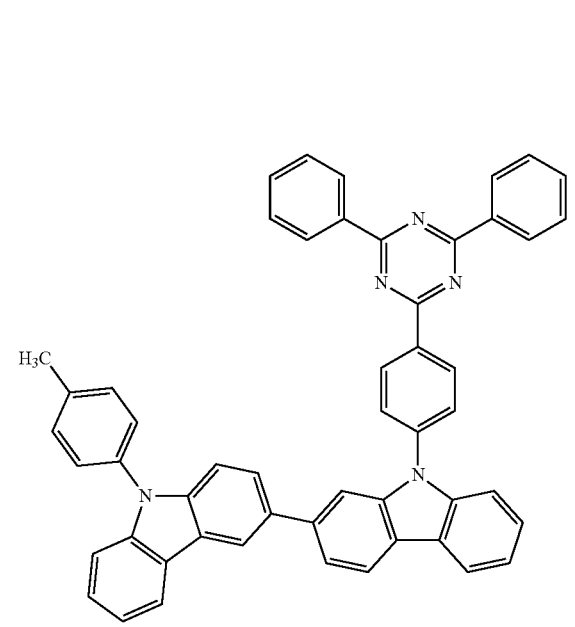
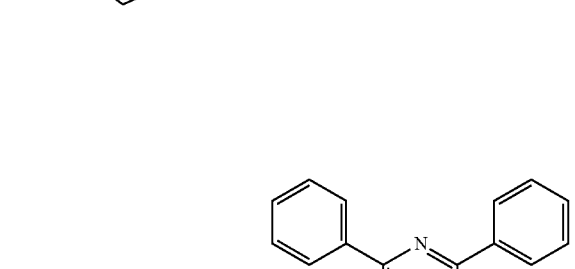
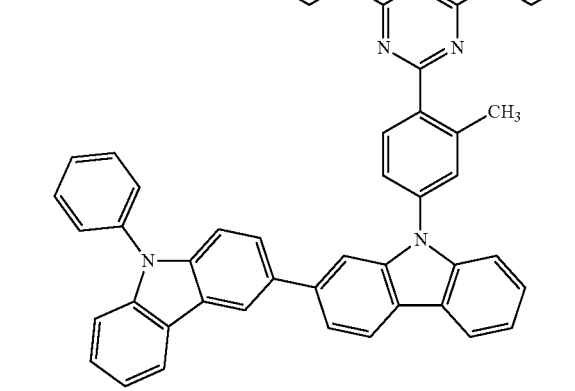
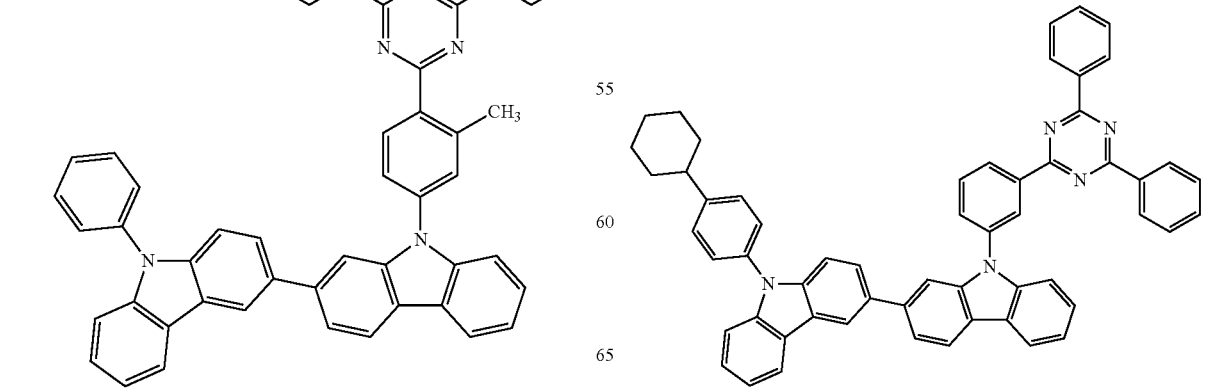

-continued

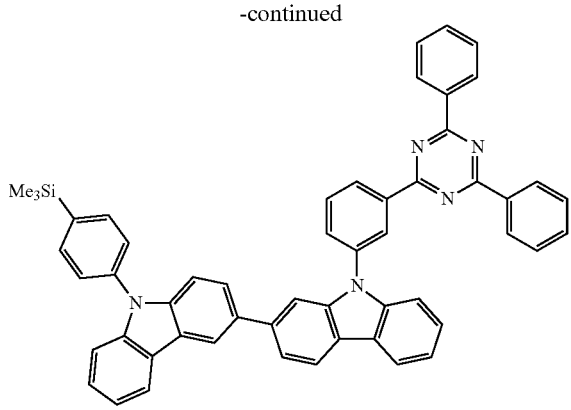

Second Compound

A second compound is represented by a formula (2) below.

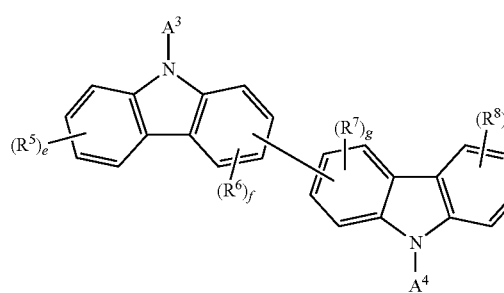
(2)

In the formula (2), $R^5$ to $R^8$ each independently represent: a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

e is 0, 1, 2, 3 or 4.
f is 0, 1, 2 or 3.
g is 0, 1, 2 or 3.
h is 0, 1, 2, 3 or 4.

A plurality of $R^5$ are mutually the same or different when e is 2 or more.

A plurality of $R^6$ are mutually the same or different when f is 2 or more.

A plurality of $R^7$ are mutually the same or different when g is 2 or more.

A plurality of $R^8$ are mutually the same or different when h is 2 or more.

One of $A^3$ and $A^4$ is a substituent represented by a formula (2a), and the other thereof is represented by a formula (2b).

—Ar—CN    (2a)

In the formula (2a), Ar represents a substituted or unsubstituted phenanthrylene group.

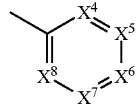
(2b)

In the formula (2b), $X^4$, $X^5$, $X^6$, $X^7$ and $X^8$ each independently represent $CR^Y$ or a nitrogen atom. $R^Y$ represents a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

A plurality of $R^Y$ are mutually the same or different.

In the second compound, it is preferable that $X^4$, $X^5$, $X^6$, $X^7$ and $X^8$ are each independently $CR^Y$, in which $R^Y$ represents a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group, and a plurality of $R^Y$ are mutually the same or different.

In the second compound, it is also preferable that $X^4$, $X^5$, $X^6$, $X^7$ and $X^8$ are $CR^Y$, in which $R^Y$ is a hydrogen atom.

In the second compound, e, f, g and h are preferably 0.

When e, f, g and h are 0 in the formula (2), the second compound is represented by a formula (2A) below.

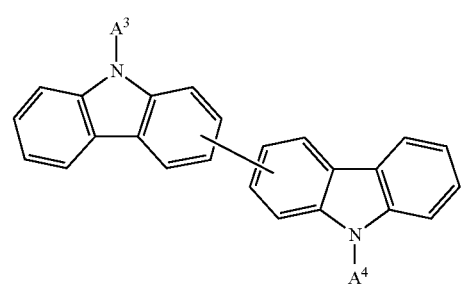
(2A)

In the formula (2A), one of $A^3$ and $A^4$ is the substituent represented by the formula (2a), and the other thereof is represented by the formula (2b).

The substituent represented by the formula (2a) is preferably a substituent represented by a formula (2c), a formula (2d) or a formula (2e) below.

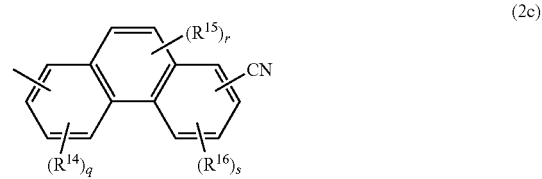
(2c)

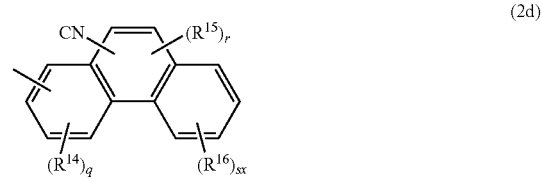
(2d)

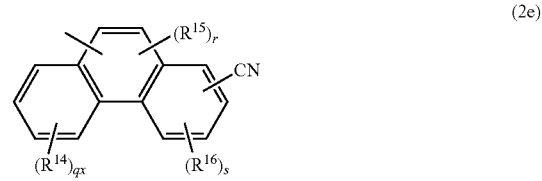
(2e)

In the formulae (2c), (2d) and (2e), $R^{14}$ to $R^{16}$ each independently represent: a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

In the formula (2c), q is 0, 1, 2 or 3.
r is 0, 1 or 2.
s is 0, 1, 2 or 3.
A plurality of $R^{14}$ are mutually the same or different when q is 2 or more.
A plurality of $R^{15}$ are mutually the same or different when r is 2 or more.
A plurality of $R^{16}$ are mutually the same or different when s is 2 or more.
In the formula (2d), q is 0, 1, 2 or 3.
r is 0 or 1.
sx is 0, 1, 2, 3 or 4.
A plurality of $R^{14}$ are mutually the same or different when q is 2 or more.
A plurality of $R^{16}$ are mutually the same or different when sx is 2 or more.
In the formula (2e), qx is 0, 1, 2, 3 or 4.
r is 0 or 1.
s is 0, 1, 2 or 3.
A plurality of $R^{14}$ are mutually the same or different when qx is 2 or more.
A plurality of $R^{16}$ are mutually the same or different when s is 2 or more.

The substituent represented by the formula (2a) is more preferably the substituent represented by the formula (2c).

The substituent represented by the formula (2c) is preferably a substituent represented by a formula (2f) below, more preferably a substituent represented by a formula (2g) below.

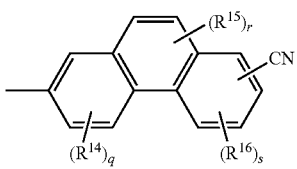
(2f)

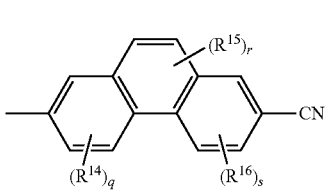
(2g)

In the formulae (2f) and (2g), $R^{14}$ to $R^{16}$ each independently represent: a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.
q is 0, 1, 2 or 3.
r is 0, 1 or 2.
s is 0, 1, 2 or 3.

A plurality of $R^{14}$ are mutually the same or different when q is 2 or more.
A plurality of $R^{15}$ are mutually the same or different when r is 2 or more.
A plurality of $R^{16}$ are mutually the same or different when s is 2 or more.

In the second compound, q, r, s, qx and sx are preferably 0.

The second compound is preferably a compound represented by a formula (5) below.

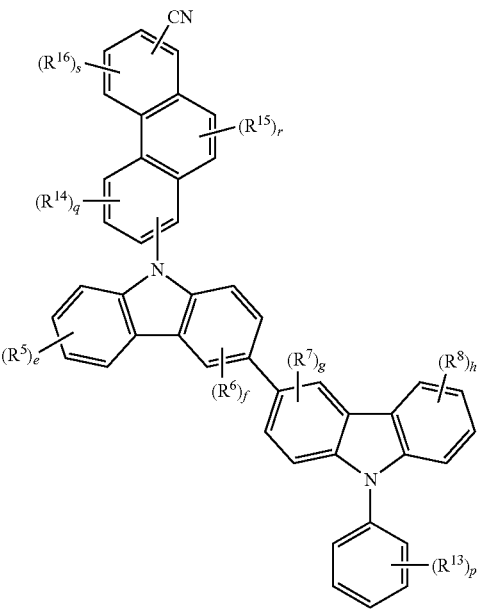
(5)

In the formula (5), $R^5$ to $R^8$ and $R^{13}$ to $R^{16}$ each independently represent: a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.
e is 0, 1, 2, 3 or 4.
f is 0, 1, 2 or 3.
g is 0, 1, 2 or 3.
h is 0, 1, 2, 3 or 4.
p is 0, 1, 2, 3, 4 or 5.
q is 0, 1, 2 or 3.
r is 0, 1 or 2.
s is 0, 1, 2 or 3.
A plurality of $R^5$ are mutually the same or different when e is 2 or more.
A plurality of $R^6$ are mutually the same or different when f is 2 or more.
A plurality of $R^7$ are mutually the same or different when g is 2 or more.
A plurality of $R^8$ are mutually the same or different when h is 2 or more.
A plurality of $R^{13}$ are mutually the same or different when p is 2 or more.
A plurality of $R^{14}$ are mutually the same or different when q is 2 or more.

A plurality of $R^{15}$ are mutually the same or different when r is 2 or more.

A plurality of $R^{16}$ are mutually the same or different when s is 2 or more.

When e, f, g and h are 0 in the formula (5), the second compound is represented by a formula (5A) below.

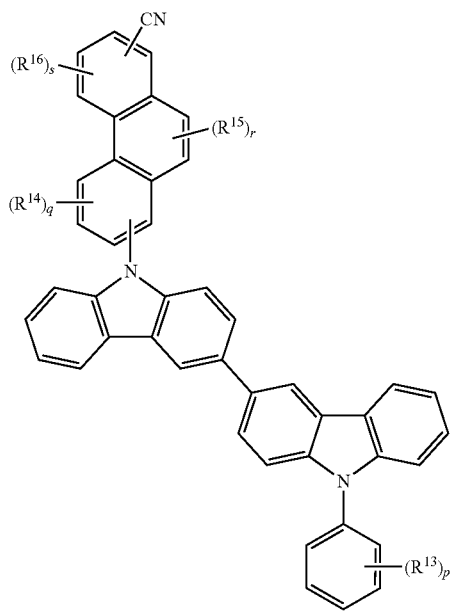

(5A)

In the formula (5A): $R^{13}$ to $R^{16}$ each independently represent: a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group.

p is 0, 1, 2, 3, 4 or 5.

q is 0, 1, 2 or 3.

r is 0, 1 or 2.

s is 0, 1, 2 or 3.

A plurality of $R^{13}$ are mutually the same or different when p is 2 or more.

A plurality of $R^{14}$ are mutually the same or different when q is 2 or more.

A plurality of $R^{15}$ are mutually the same or different when r is 2 or more.

A plurality of $R^{16}$ are mutually the same or different when s is 2 or more.

In the second compound, p, q, r and s are preferably 0.

In the second compound, e, f, g, h, p, q, r and s are preferably 0.

When e, f, g, h, p, q, r and s are 0 in the formula (5), the second compound is represented by a formula (5B).

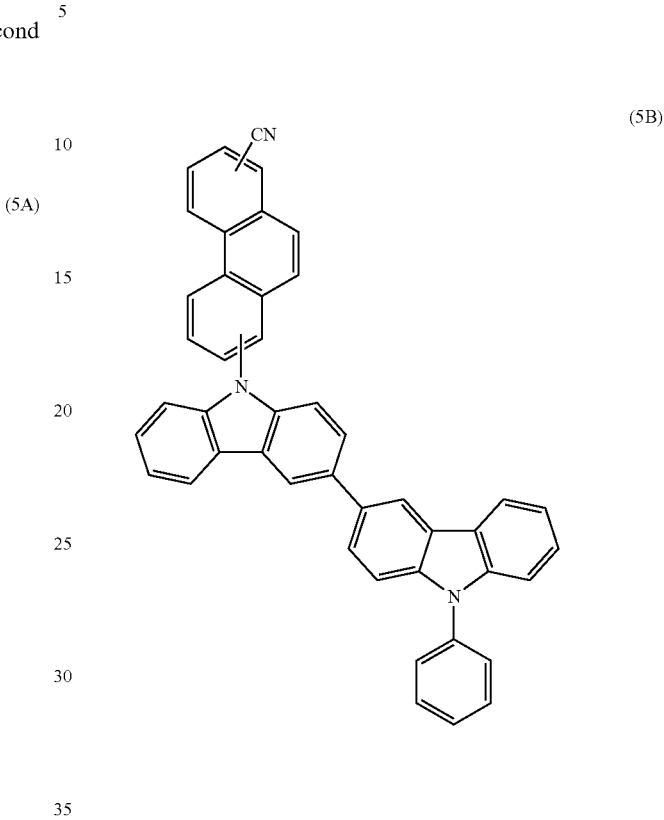

(5B)

The second compound can be manufactured by a combination of known methods (e.g., International Publication No. WO2013/084885).

Examples of the second compound according to the exemplary embodiment are given below. It should be noted that the second compound in the exemplary embodiment are by no means limited to the examples below.

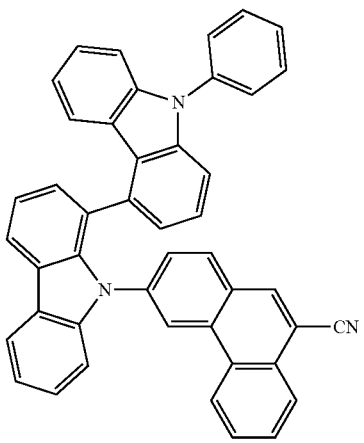

-continued
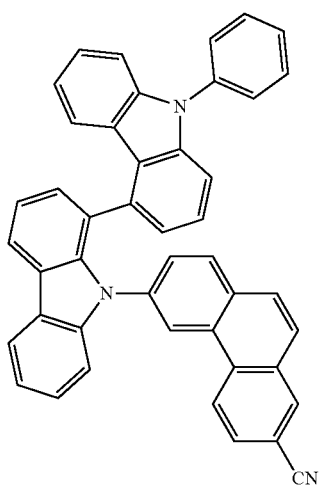
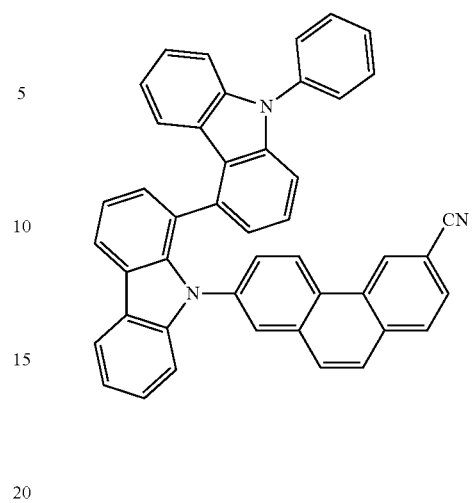
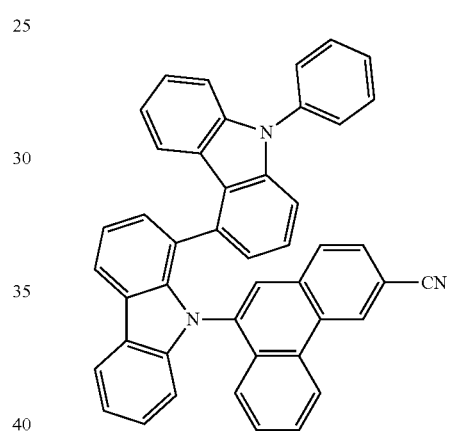
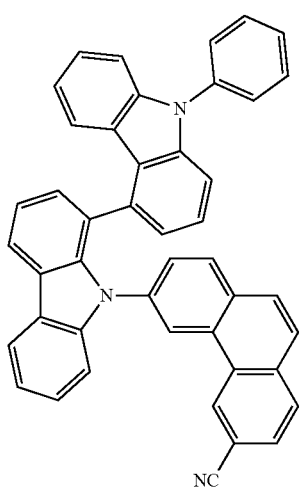
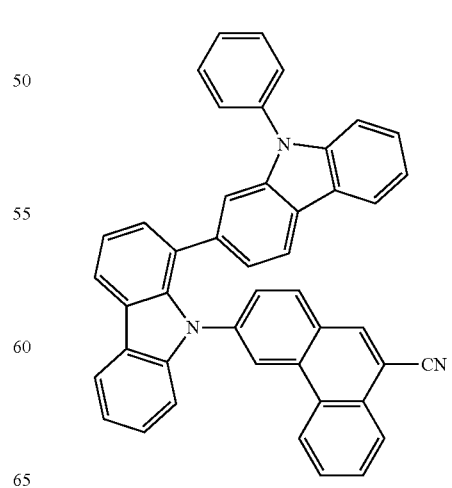

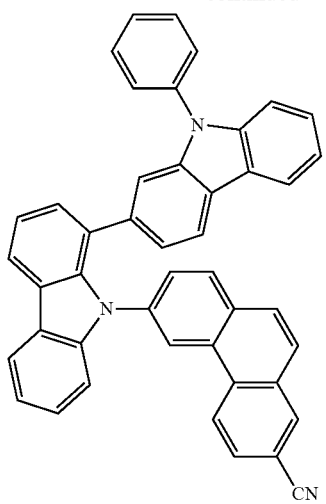
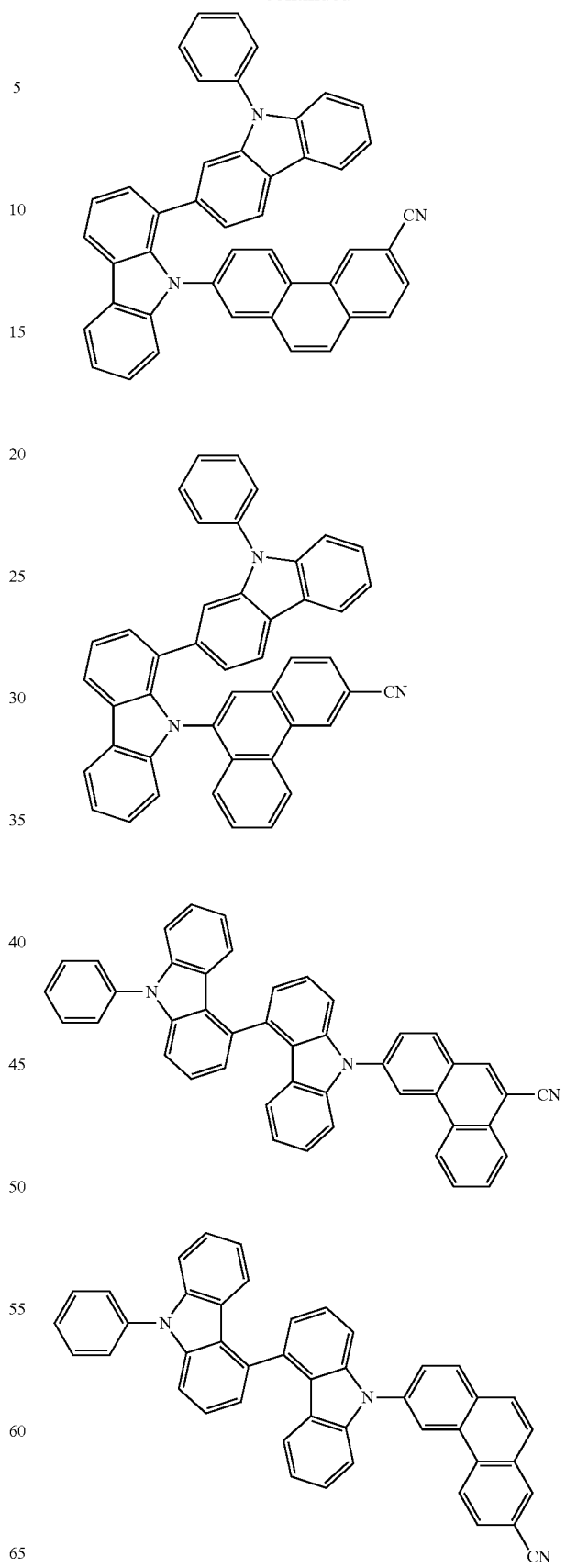

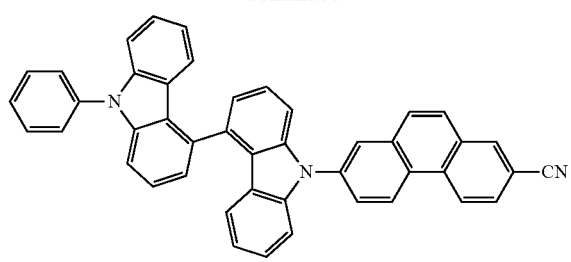
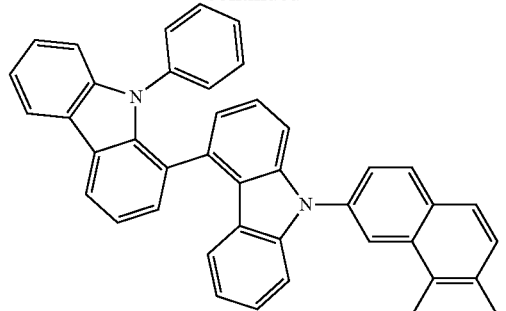
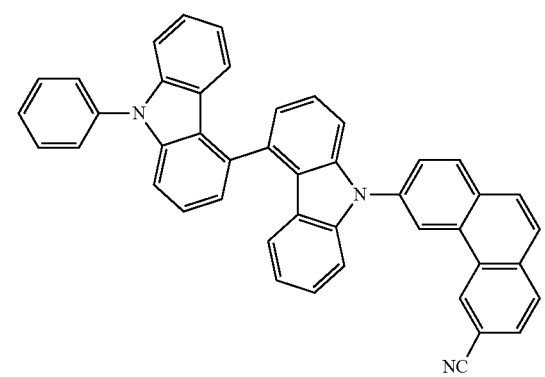
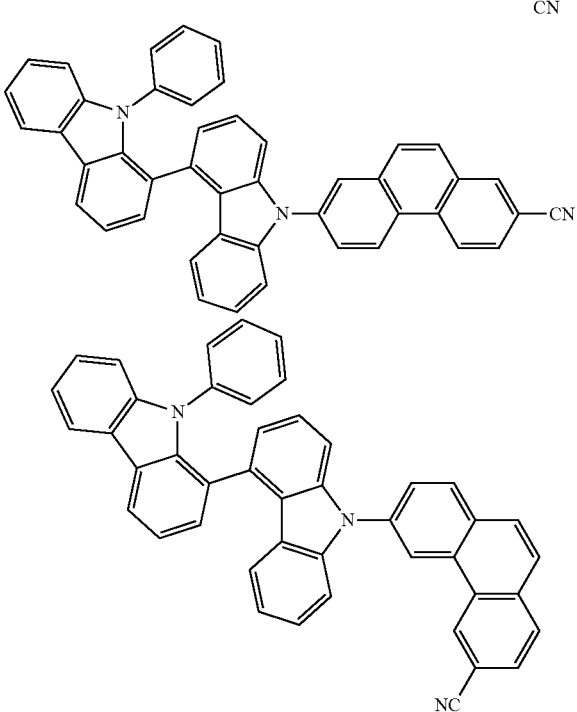
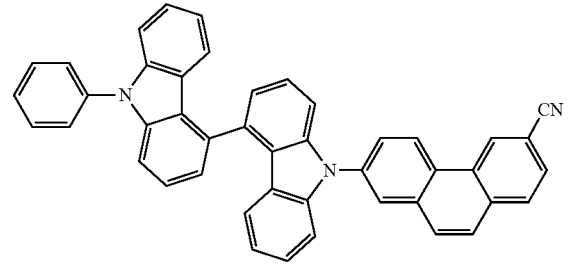
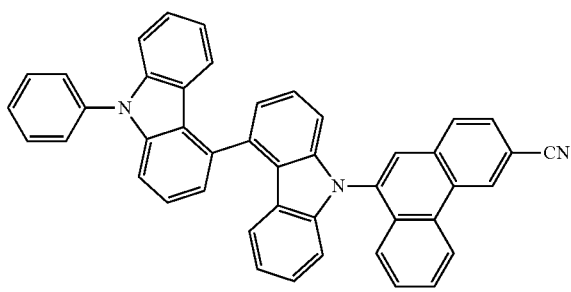
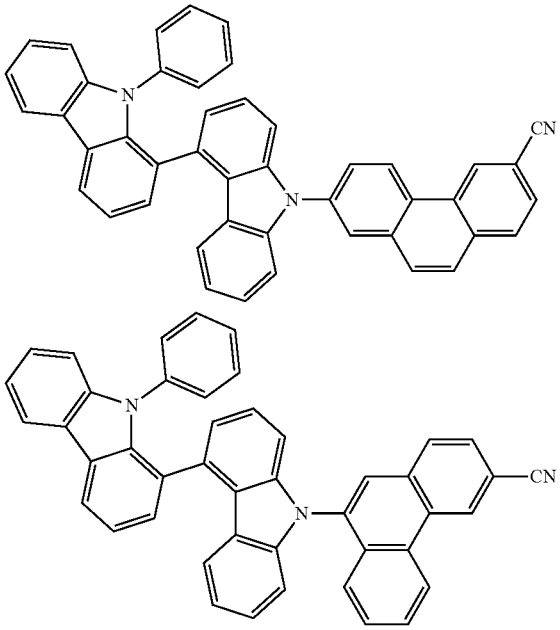
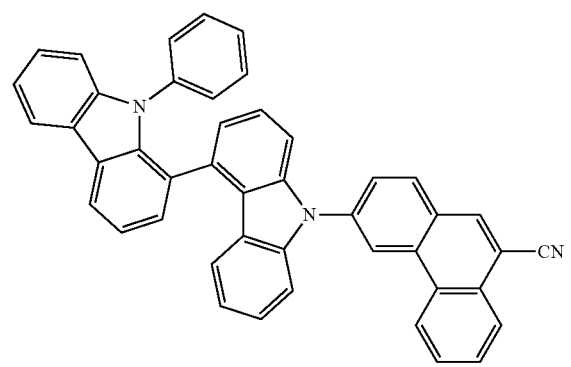

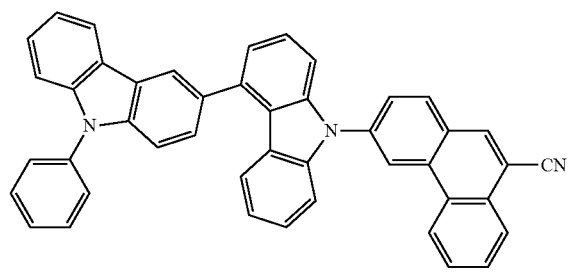
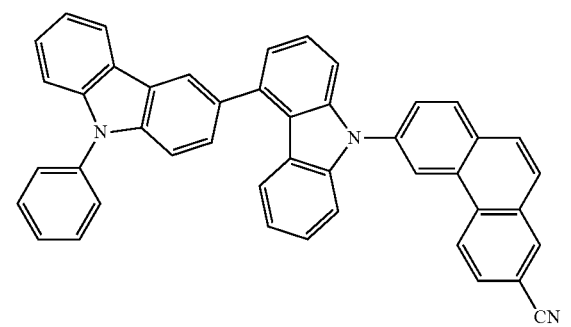
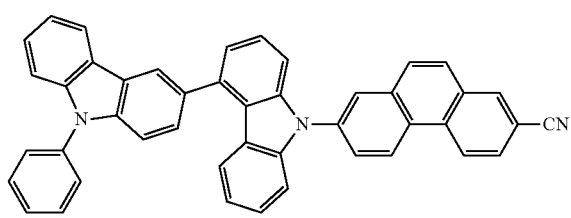
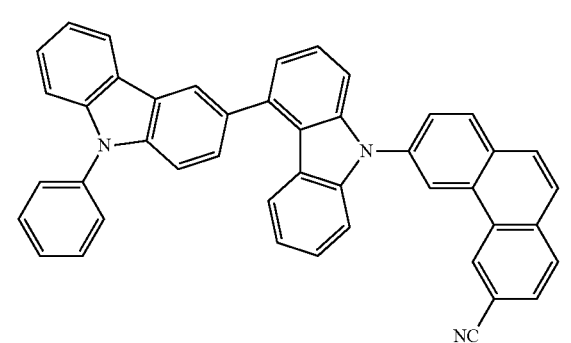
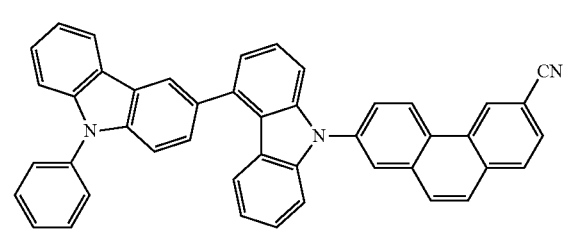
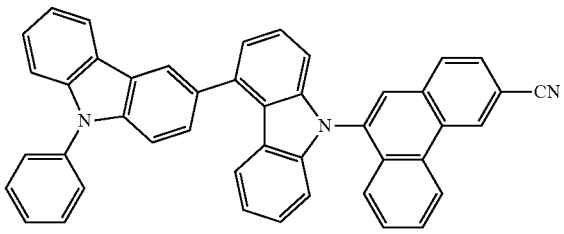
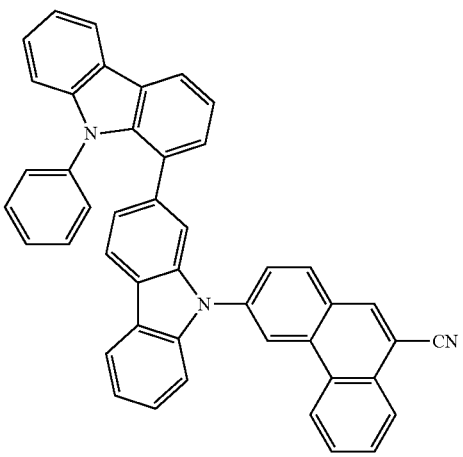
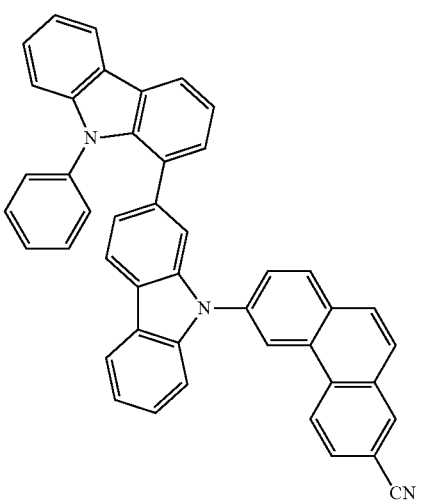
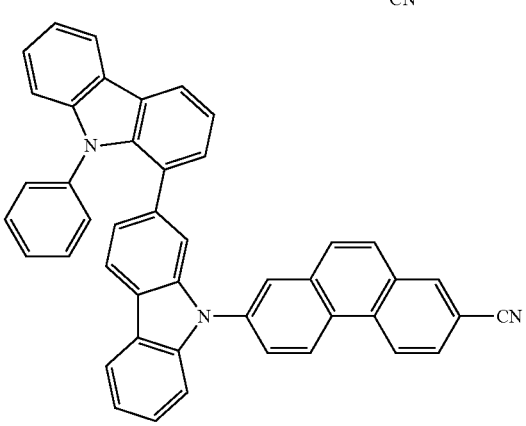

31
-continued
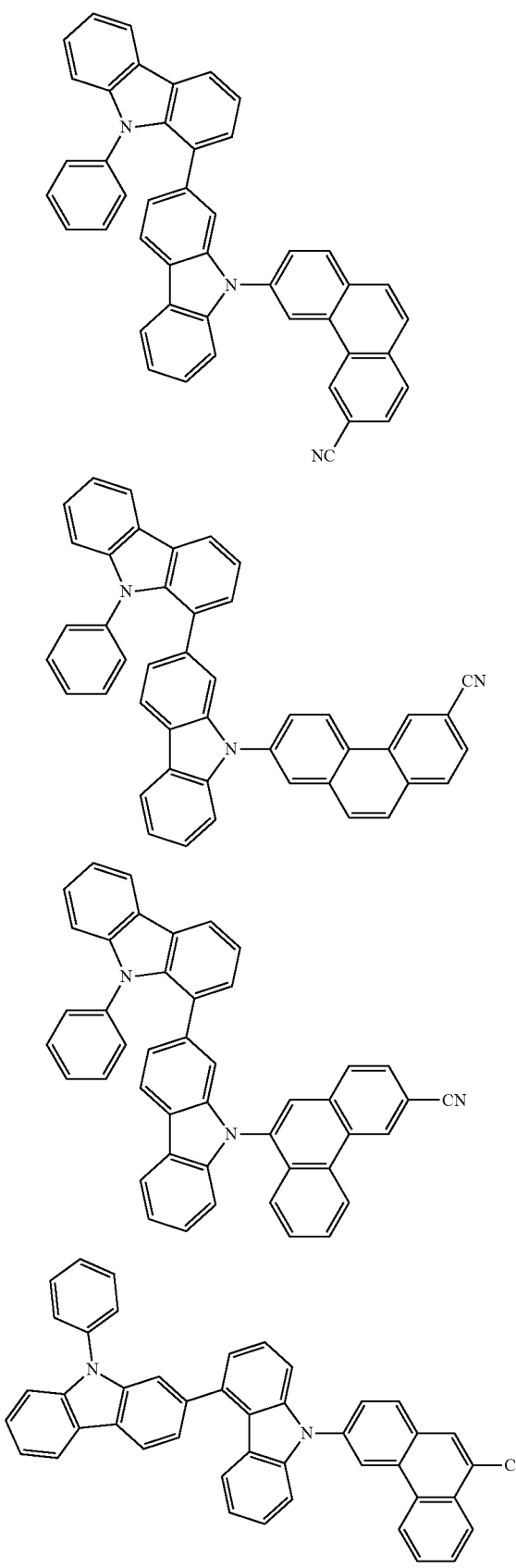
32
-continued
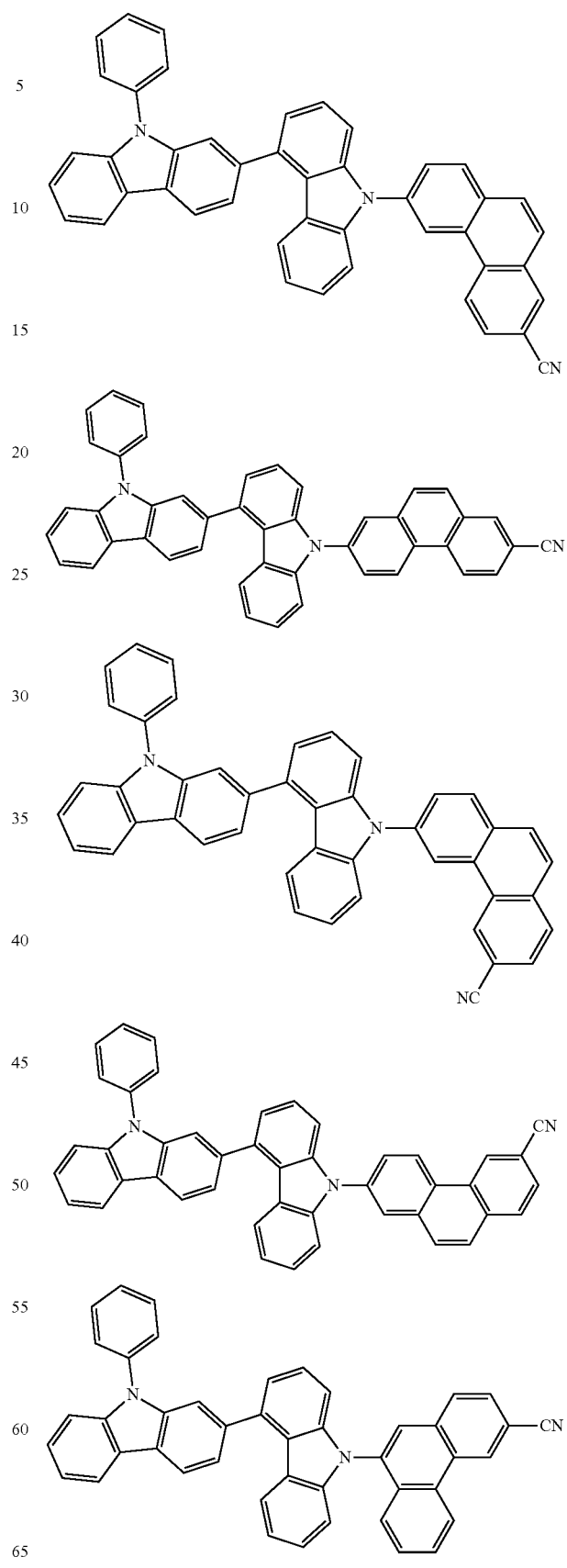

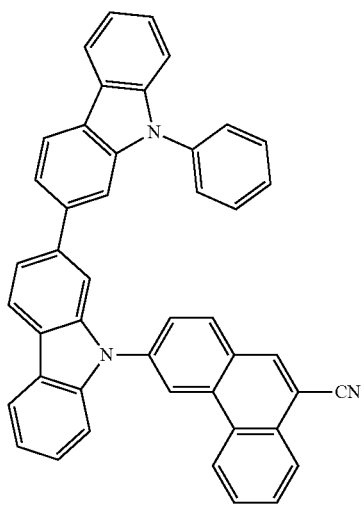
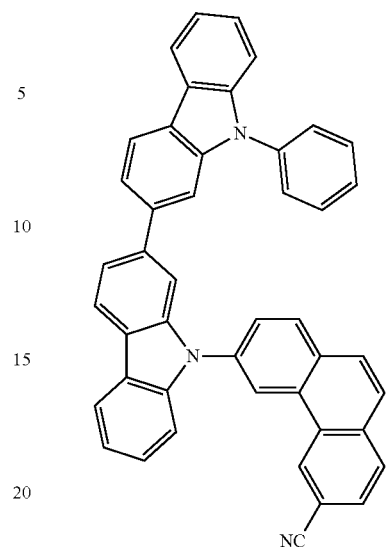
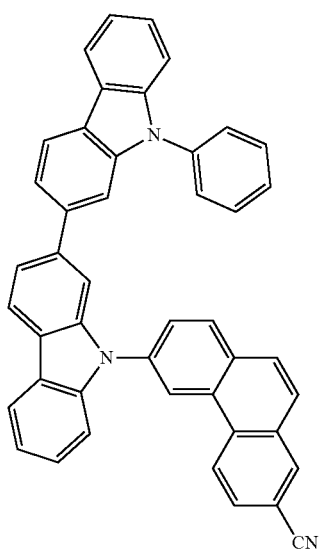
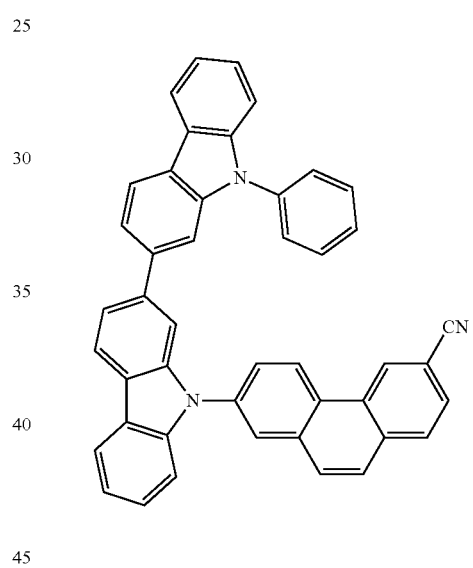
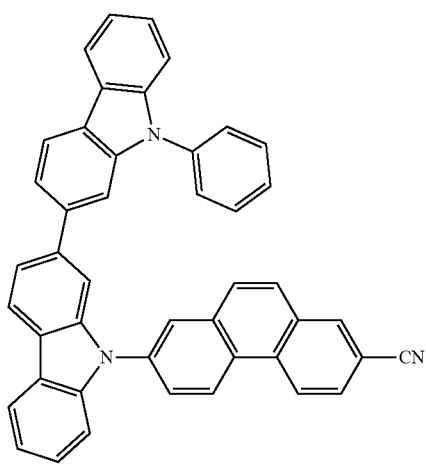
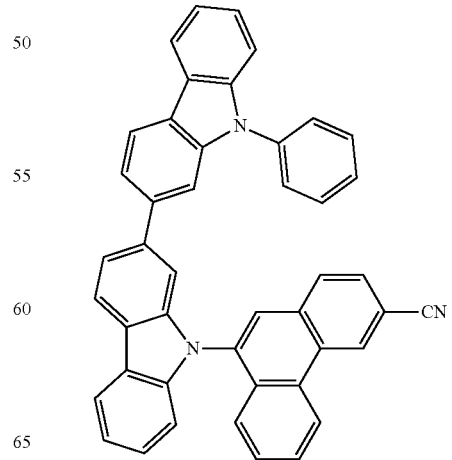

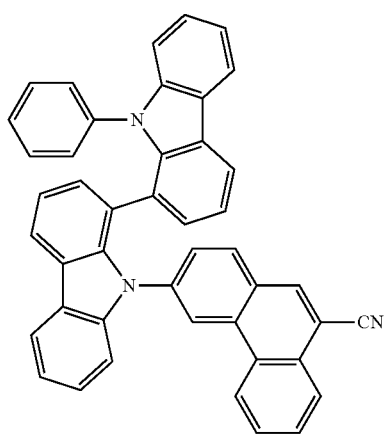
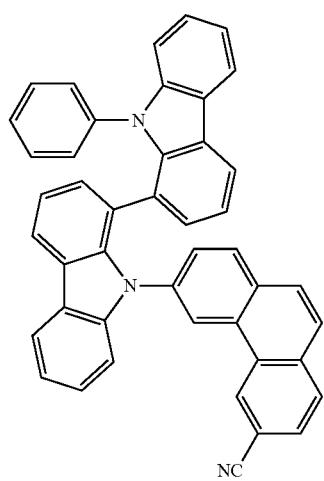
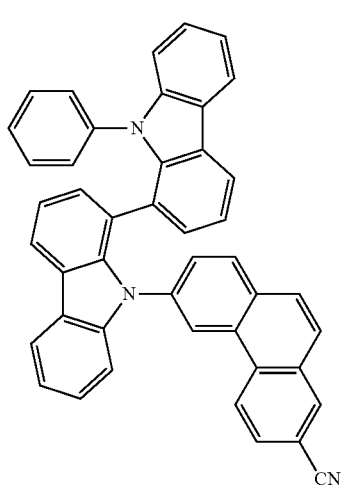
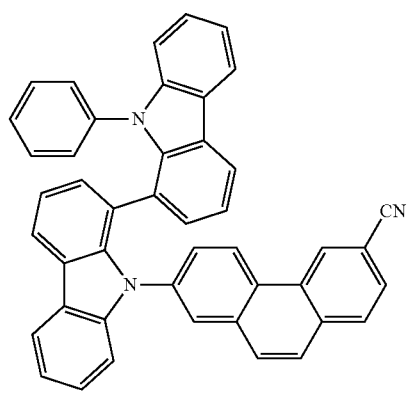
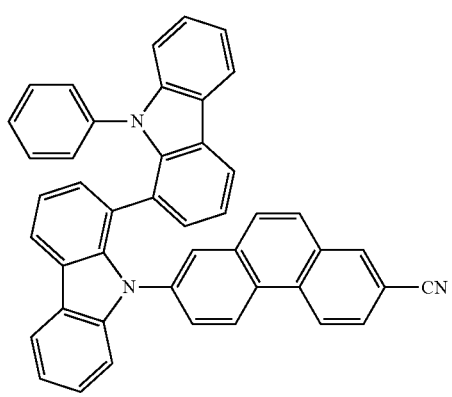
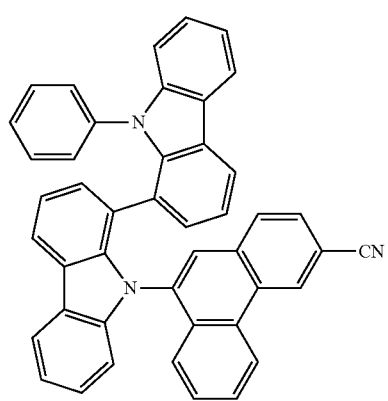

37
-continued
38
-continued
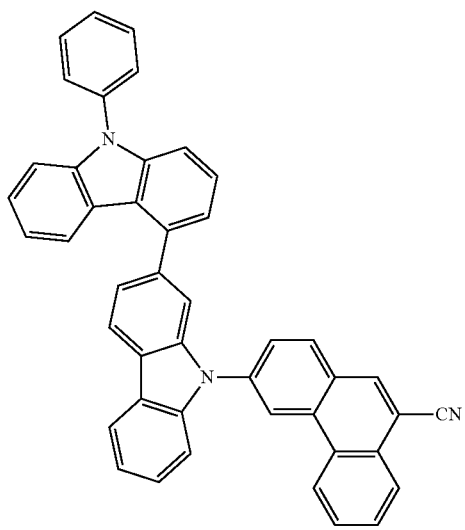
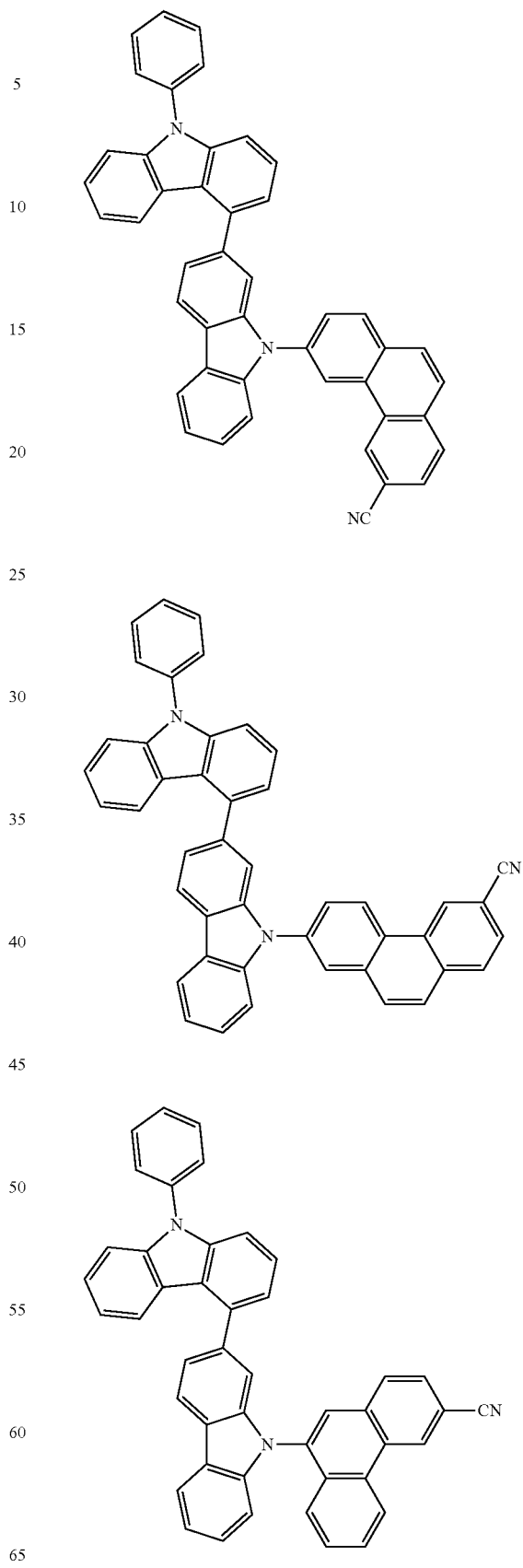

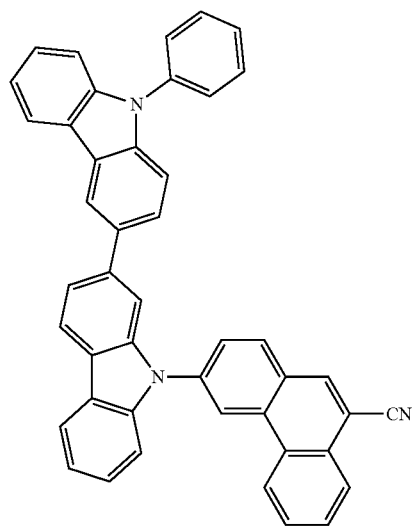
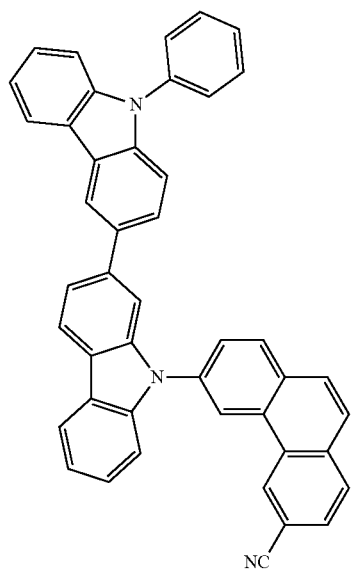
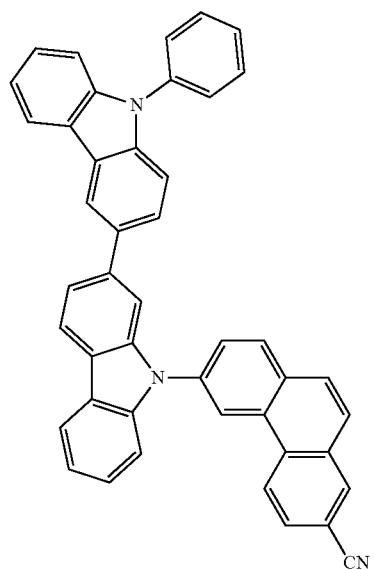
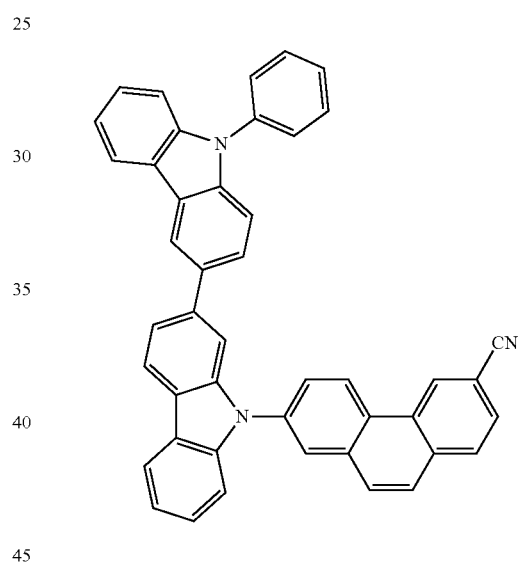
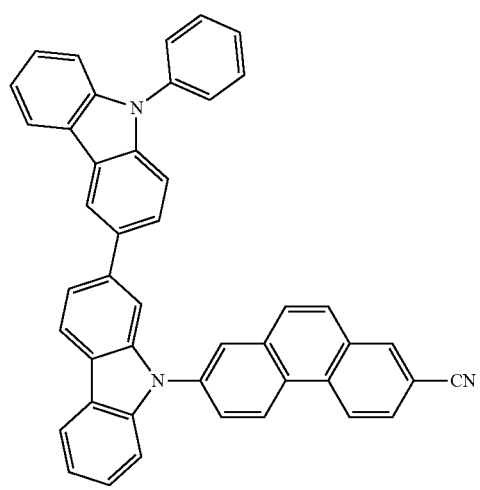
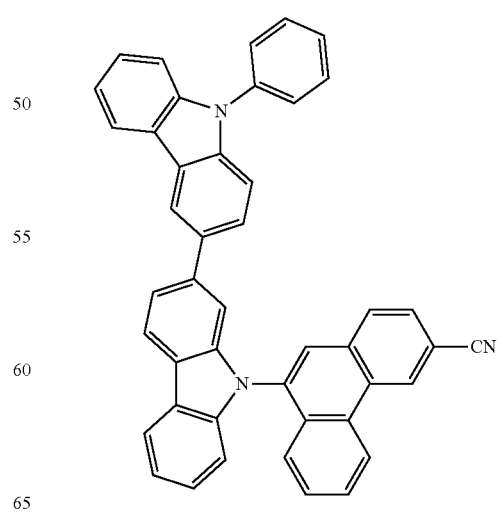

-continued
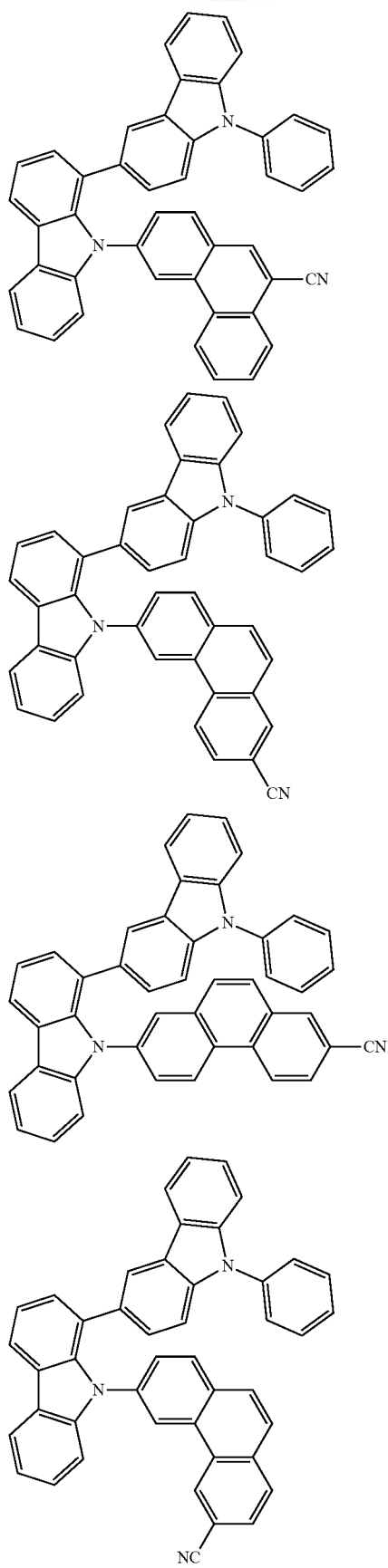
-continued
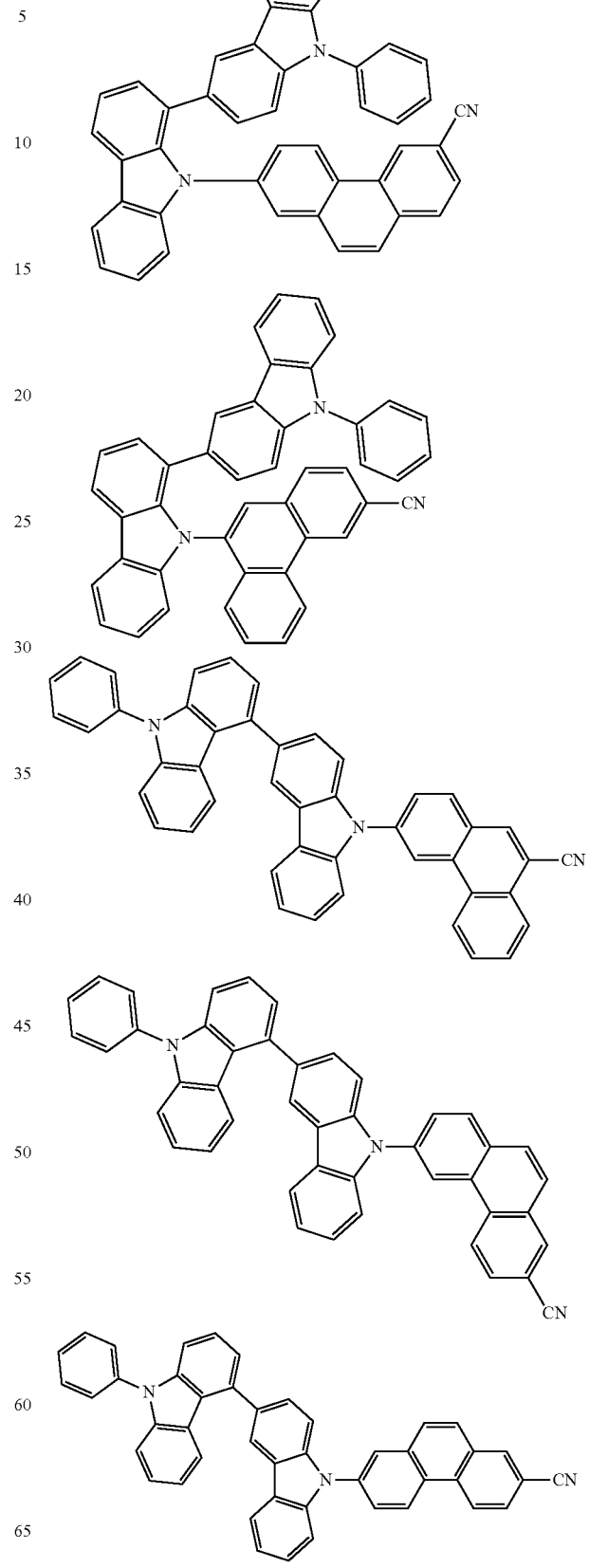

-continued
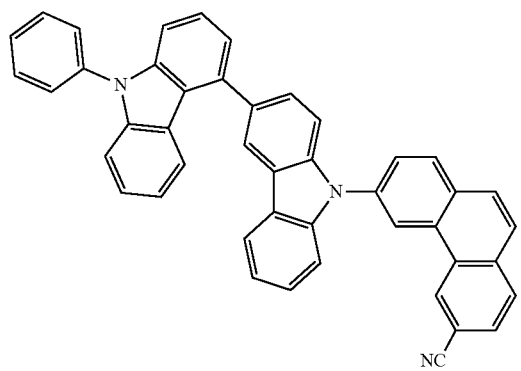
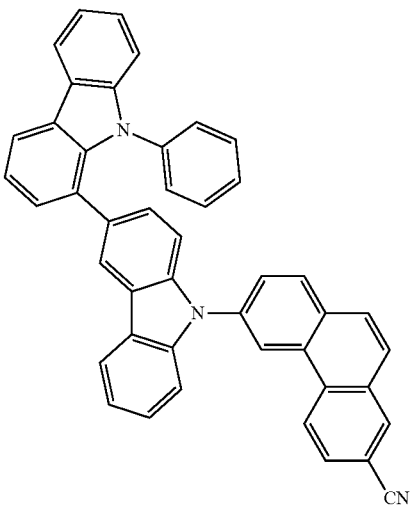
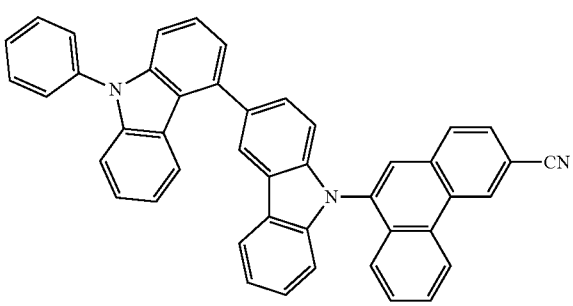
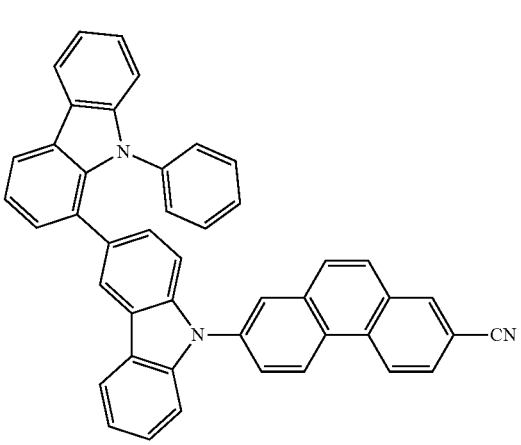
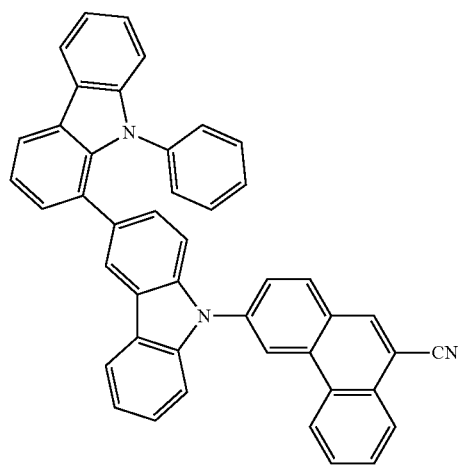
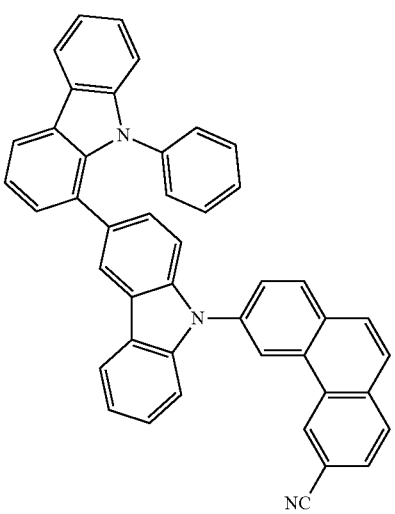

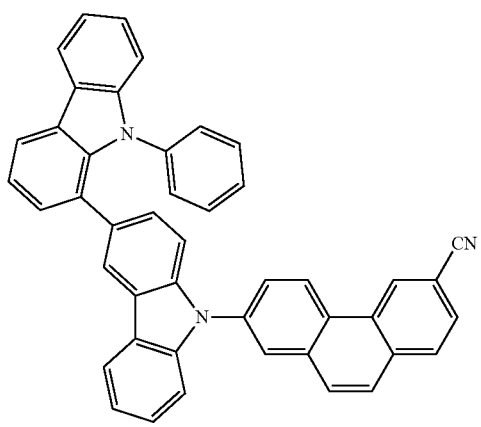
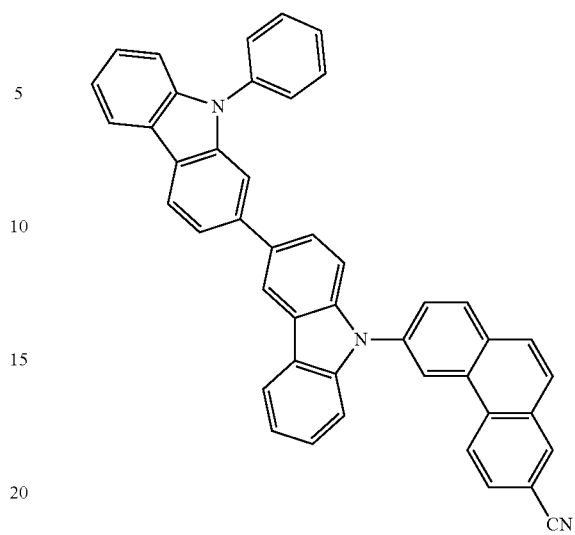
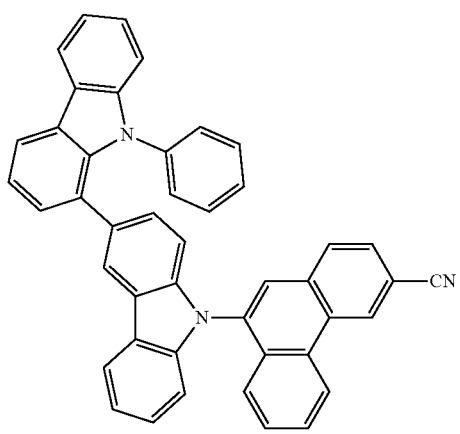
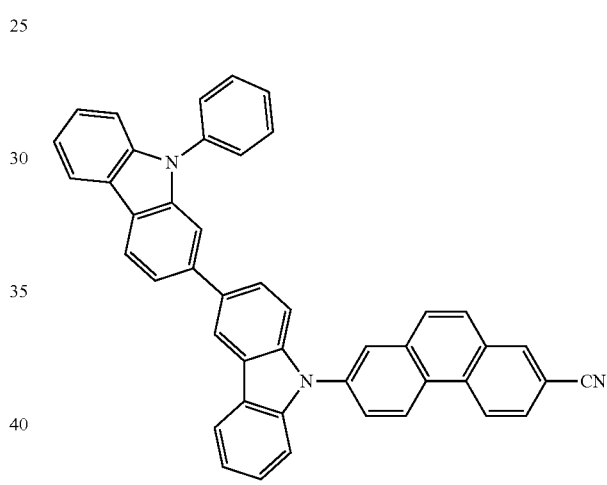
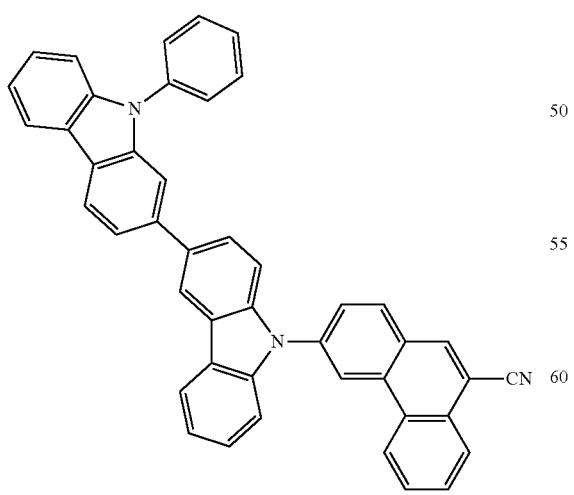
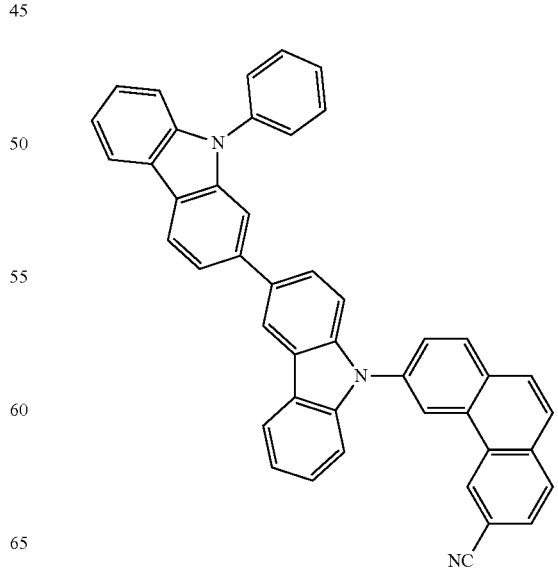

47
-continued
48
-continued
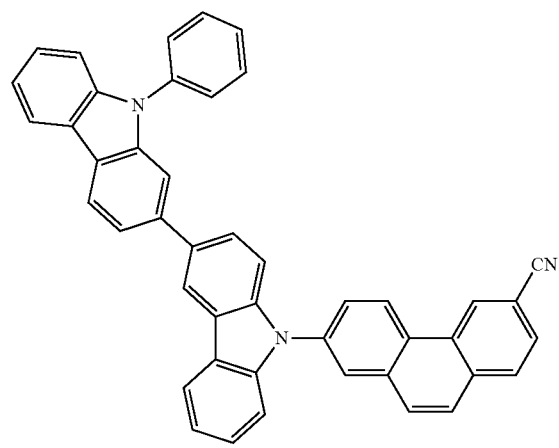
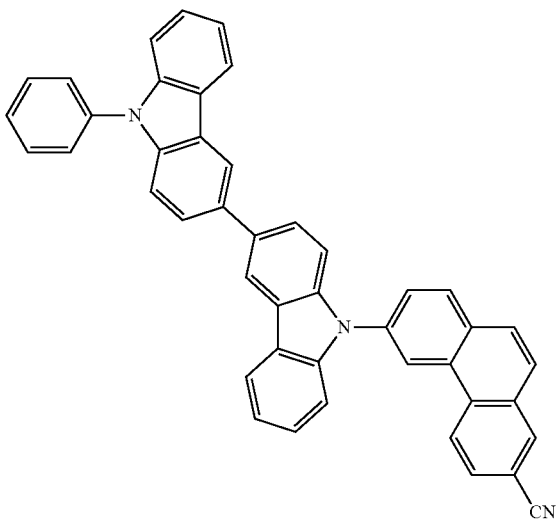
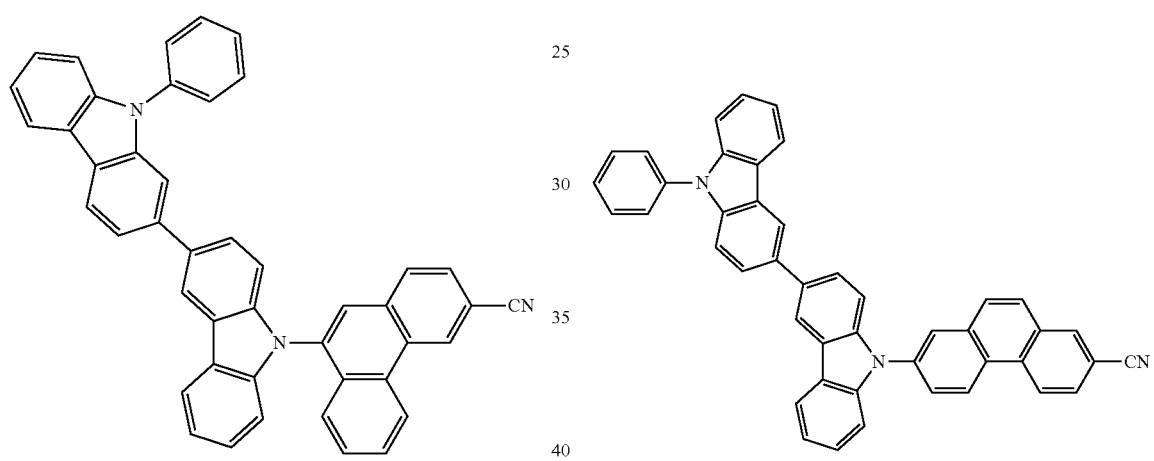
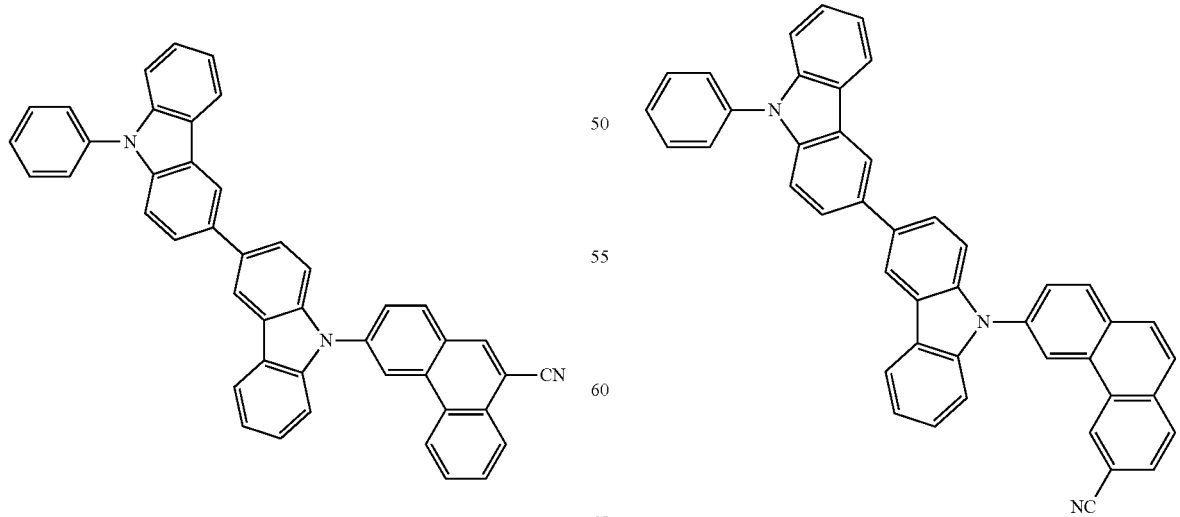

-continued

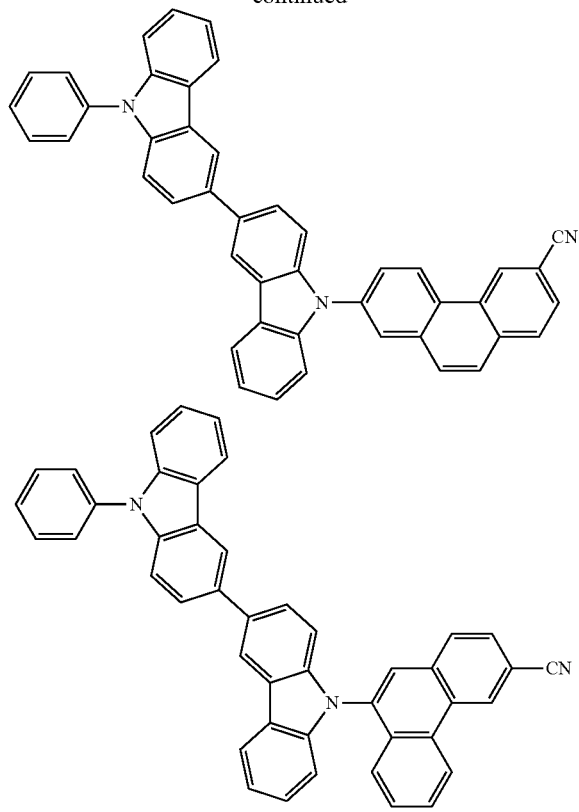

Since the composition of the exemplary embodiment contains a combination of the first compound and the second compound, the composition of the exemplary embodiment can be evaporated from a single evaporation source at a stable material ratio while maintaining the performance of the organic electroluminescence device.

Compounding Ratio of Composition

In an exemplary embodiment of the invention, a compounding ratio of the first compound and the second compound is not particularly limited. The compounding ratio of the first compound and the second compound only needs to be appropriately determined depending on desired effects of the composition. The compounding ratio (mass ratio) represented by the first compound the second compound is usually in a range from 1:99 to 99:1, preferably in a range from 10:90 to 90:10.

Organic-Electroluminescence-Device Material

An organic-electroluminescence-device material according to the exemplary embodiment includes the composition according to the exemplary embodiment. Specifically, the organic-electroluminescence-device material according to the exemplary embodiment includes the first compound and the second compound.

The organic-electroluminescence-device material according to the exemplary embodiment may further include an additional compound. When the organic-electroluminescence-device material according to the exemplary embodiment further includes the additional compound, the additional compound may be solid or liquid.

Composition Film

A composition film according to the exemplary embodiment includes the composition according to the exemplary embodiment. Specifically, a film containing the composition according to the exemplary embodiment (hereinafter, also referred to as a composition film) means a film containing the first compound and the second compound.

The composition film according to the exemplary embodiment may further include an additional compound.

A forming method of the composition film according to the exemplary embodiment is not particularly limited unless otherwise specified herein. Known methods such as a dry film-forming method and a wet film-forming method are usable as the forming method of the composition film. Examples of the dry film-forming method include vacuum evaporation, sputtering, plasma deposition and ion plating. Examples of the wet film-forming include spin coating, dipping, flow coating and ink-jet.

Device Arrangement of Organic EL Device

An organic EL device according to the exemplary embodiment includes an anode, a cathode, and an organic layer between the anode and the cathode. The organic layer includes at least one layer formed from an organic compound. Alternatively, the organic layer is a laminate of a plurality of layers formed from the organic compound. The organic layer may further include an inorganic compound. In the organic EL device according to the exemplary embodiment, at least one layer of the organic layer is an emitting layer. Accordingly, the organic layer may be a single emitting layer, or may further include a layer(s) usable for the organic EL device. The layer(s) usable for the organic EL device is not particularly limited but is at least one layer selected from the group consisting of a hole injecting layer, a hole transporting layer, an electron injecting layer, an electron transporting layer, and a blocking layer.

In the exemplary embodiment, it is preferable that the organic layer includes the plurality of layers and at least one of the plurality of layers contains the composition of the exemplary embodiment.

Since the composition of the exemplary embodiment is used in the at least one of the layers in the organic EL device of the exemplary embodiment, a high performance of the organic EL device (e.g., at least one luminescent performance of a drive voltage, a luminous efficiency and a lifetime) is obtainable. Further, when the composition of the exemplary embodiment is formed into a film using the method of the exemplary embodiment (e.g., vacuum evaporation), a material ratio between the first compound and the second compound in the emitting layer is stable during an evaporation time from an evaporation initial stage to an evaporation terminal stage. As a result, the organic electroluminescence device can maintain a high and stable luminescent performance irrespective of the evaporation time.

In the organic EL device of the exemplary embodiment, the emitting layer preferably contains the composition of the exemplary embodiment.

In the exemplary embodiment, the organic EL device preferably further includes a hole transporting layer between the anode and the emitting layer.

In the exemplary embodiment, the organic EL device preferably further includes an electron transporting layer between the cathode and the emitting layer.

In another exemplary embodiment, it is also preferable that the composition of the exemplary embodiment is used in the electron transporting zone.

Typical device arrangements of an organic EL device include the following arrangements (a) to (f) and the like:
(a) anode/emitting layer/cathode;
(b) anode/hole injecting•transporting layer/emitting layer/cathode;

(c) anode/emitting layer/electron injecting•transporting layer/cathode;

(d) anode/hole injecting•transporting layer/emitting layer/electron injecting•transporting layer/cathode.

(e) anode/hole injecting•transporting layer/emitting layer/blocking layer/electron injecting•transporting layer/cathode; and (f) anode/hole injecting•transporting layer/blocking layer/emitting layer/blocking layer/electron injecting•transporting layer/cathode.

While the arrangement (d) is preferably used among the above device arrangements, the arrangement of the invention is not limited to the above. It should be noted that the above-described "emitting layer" is an organic layer having an emitting function. The above-described "hole injecting•transporting layer" means at least one of a hole injecting layer and a hole transporting layer." The above-described "electron injecting•transporting layer" means at least one of an electron injecting layer and an electron transporting layer." When the organic EL device includes the hole injecting layer and the hole transporting layer, the hole injecting layer is preferably provided between the hole transporting layer and the anode. When the organic EL device includes the electron injecting layer and the electron transporting layer, the electron injecting layer is preferably provided between the electron transporting layer and the cathode. Each of the hole injecting layer, the hole transporting layer, the electron transporting layer, and the electron injecting layer may consist of a single layer or a plurality of layers.

The FIGURE schematically shows an arrangement of the organic EL device of the exemplary embodiment.

An organic EL device 1 includes a light-transmissive substrate 2, an anode 3, a cathode 4 and an organic layer 10 disposed between the anode 3 and the cathode 4. The organic layer 10 includes a hole injecting layer 6, a hole transporting layer 7, an emitting layer 5, an electron transporting layer 8, and an electron injecting layer 9. The organic layer 10 includes the hole injecting layer 6, the hole transporting layer 7, the emitting layer 5, the electron transporting layer 8, and the electron injecting layer 9, which are sequentially laminated on the anode 3.

The emitting layer 5 of the organic EL device 1 contains the composition of the exemplary embodiment. In other words, the emitting layer 5 contains the first compound and the second compound.

The organic EL device of the exemplary embodiment is driven at a low voltage since the first compound and the second compound are used in combination in the organic layer. In order to drive the organic EL device at a low voltage, the first compound and the second compound are preferably contained in a single emitting layer.

Compounding Ratio of Organic EL Device

In an exemplary embodiment of the invention, a compounding ratio of the first compound and the second compound is not particularly limited. The compounding ratio of the first compound and the second compound only needs to be appropriately determined depending on desired effects of the organic EL device. The compounding ratio (mass ratio) represented by the first compound the second compound is usually in a range from 1:99 to 99:1, preferably in a range from 10:90 to 90:10.

Layer Formation Method(s)

A forming method of each layer of the organic EL device according to the exemplary embodiment is not particularly limited unless otherwise specified herein. Known methods such as a dry film-forming method and a wet film-forming method are usable as the forming method of the layer. Examples of the dry film-forming include vacuum evaporation, sputtering, plasma deposition and ion plating. Examples of the wet film-forming include spin coating, dipping, flow coating and ink-jet.

Film Thickness

A film thickness of each layer in the organic EL device according to the exemplary embodiment is not limited except for the above particular description. The film thickness of each layer needs to be set at an appropriate thickness. When the film thickness is too thick, a large applied voltage may be required for obtaining emission at a certain level, which may deteriorate efficiency. When the film thickness is too thin, pin holes and the like may generate, which may cause an insufficient luminescence intensity even when an electric field is applied The film thickness is typically preferably in a range from 5 nm to 10 µm, more preferably in a range of 10 nm to 0.2 µm.

Materials and the like of components of the organic EL device will be described below.

Substrate

A substrate is used as a support for an emitting device. For instance, glass, quartz, plastics and the like are usable as the substrate. A flexible substrate is also usable. The flexible substrate is a bendable substrate, which is exemplified by a plastic substrate formed from polycarbonate and polyvinyl chloride.

Anode

Metal, an alloy, an electrically conductive compound, a mixture thereof and the like, which have a large work function, specifically, 4.0 eV or more, are preferably usable as the anode formed on the substrate. Specific examples of the material for the anode include indium tin oxide (ITO), indium tin oxide containing silicon or silicon oxide, indium zinc oxide, tungsten oxide, indium oxide containing zinc oxide, and graphene. In addition, the examples of the material for the anode further include nitrides of gold (Au), platinum (Pt), or metal materials (e.g., titanium nitride).

Hole Injecting Layer

The hole injecting layer is a layer for efficiently injecting holes from the anode into the organic layer. Examples of a substance used for the hole injecting layer include molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, aromatic amine compound, acceptor compound, and high-molecular compound (e.g., oligomer, dendrimer, and polymer).

Among the above examples, the substance used for the hole injecting layer is preferably an aromatic amine derivative or the acceptor compound, more preferably the acceptor compound. Preferable examples of the acceptor compound include a heterocyclic derivative substituted by an electron-withdrawing group, a quinone derivative substituted by an electron-withdrawing group, an aryl borane derivative, and a heteroaryl borane derivative. Among the examples, hexacyanohexaazatriphenylene, $F_4$TCNQ (2,3,5,6-tetrafluoro-7,7,8,8-tetracyanoquinodimethane), or 1,2,3-tris[(cyano)(4-cyano-2,3,5,6-tetrafluorophenyl)methylene]cyclopropane is preferably used.

It is also preferable that a layer containing the acceptor compound further contains a matrix material. Organic-EL-device materials are widely usable as the matrix material. The matrix material used in combination with the acceptor compound is preferably a donor compound, more preferably an aromatic amine compound.

Hole Transporting Layer

The hole transporting layer is a layer containing a highly hole-transporting substance. An aromatic amine compound, carbazole derivative, anthracene derivative and the like are usable for the hole transporting layer. Moreover, a high-molecular compound such as poly(N-vinylcarbazole) (abbreviation: PVK) and poly(4-vinyltriphenylamine) (abbreviation: PVTPA) is also usable for the hole transporting layer. However, any substance having a hole transporting performance higher than an electron transporting performance may be used in addition to the above substances. The layer including the highly hole-transporting substance may be provided in the form of a single layer or a laminate of two or more layers containing the above substance. A hole transporting material is preferably a compound represented by a formula (H) below.

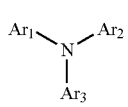

(H)

In the formula (H), $Ar_1$ to $Ar_3$ each independently represent a substituted or unsubstituted aryl group having 6 to 50 ring carbon atoms, a substituted or unsubstituted heterocyclic group having 5 to 50 ring atoms, or a group formed by combining the substituted or unsubstituted aryl group with the substituted or unsubstituted heterocyclic group. The aryl group is preferably a substituent such as a phenyl group, biphenyl group, terphenyl group, fluorenyl group, spirobifluorenyl group, indenofluorenyl group, naphthyl group, phenanthryl group, anthryl group, and triphenylenyl group. The heterocyclic group is preferably a dibenzofuranyl group, dibenzothiophenyl group, carbazolyl group and the like. The group formed by combining the aryl group with the heterocyclic group is preferably a dibenzofuran-substituted aryl group, dibenzothiophene-substituted aryl group, and carbazole-substituted aryl group. The above substituents may have an additional substituent, preferable examples of which are described below.

The compound represented by the formula (H) is preferably in a form of a compound in which at least one of $Ar_1$ to $Ar_3$ is further substituted by an aryl amino group, and is also preferably a diamine derivative, a triamine derivative, or a tetramine derivative. Preferable examples of the diamine derivative include a tetraaryl-substituted benzidine derivative, and TPTE (4,4'-bis[N-phenyl-N-[4'-diphenylamino-1,1'-biphenyl-4-yl]amino]-1,1'-biphenyl).

The hole transporting material used for a layer adjacent to a phosphorescent layer preferably has a high triplet level. Each of $Ar_1$ to $Ar_3$ in the formula (H) is preferably a substituent such as a fluorenyl group, spirofluorenyl group, phenyl group, biphenyl group, phenanthryl group, triphenylenyl group, dibenzofuranyl group, and dibenzothiophenyl group, and a group formed by combining the substituents.

Emitting Layer

The emitting layer is a layer containing a highly emittable substance and can be formed of various materials. The emitting layer typically contains a highly emittable luminescent material (a dopant material) and a host material for promoting an efficient emission of the luminescent material. For instance, a fluorescent compound emitting fluorescence and a phosphorescent compound emitting phosphorescence are usable as the highly emittable substance. The fluorescent compound is a compound capable of emitting in a singlet state. The phosphorescent compound is a compound capable of emitting in a triplet state. The emitting layer containing the fluorescent compound is referred to as a fluorescent layer. The emitting layer containing the phosphorescent compound is referred to as a phosphorescent layer.

The fluorescent compound is widely usable as the dopant material of the fluorescent layer. Preferable examples of the dopant material of the fluorescent layer include a fused polycyclic aromatic derivative, styrylamine derivative, fused cyclic amine derivative, boron-containing compound, pyrrole derivative, indole derivative, and carbazole derivative. More preferably, the dopant material of the fluorescent layer is a fused cyclic amine derivative and a boron-containing compound. Examples of the fused cyclic amine derivative include a diaminopyrene derivative, diaminochrysene derivative, diaminoanthracene derivative, diaminofluorene derivative, and diaminofluorene derivative to which one or more benzofuro skeletons are fused. Examples of the boron-containing compound include a pyrromethene derivative and a triphenyl borane derivative. Herein, a derivative of a certain compound refers to a compound having a skeleton of the certain compound as a partial structure, and the derivative further encompasses a compound in which an additional ring is fused to the skeleton and a compound in which a plurality of substituents of the skeleton form a ring. For instance, a fused polycyclic aromatic derivative refers to a compound having a fused polycyclic aromatic skeleton as a partial structure, and further encompasses a compound in which an additional ring is fused to the fused polycyclic aromatic skeleton and a compound in which a plurality of substituents of the fused polycyclic aromatic skeleton form a ring.

A general fluorescent material is usable as the host material used in the fluorescent layer. The host material used in the fluorescent layer is preferably a compound having the fused polycyclic aromatic derivative as a main skeleton, particularly preferably an anthracene derivative, pyrene derivative, chrysene derivative, naphthacene derivative and the like. A particularly suitable host as a blue host material (i.e., a host material usable in combination with a blue fluorescent dopant material) and a green host material (a host material usable in combination with a green fluorescent dopant material) is an anthracene derivative represented by a formula (X) below.

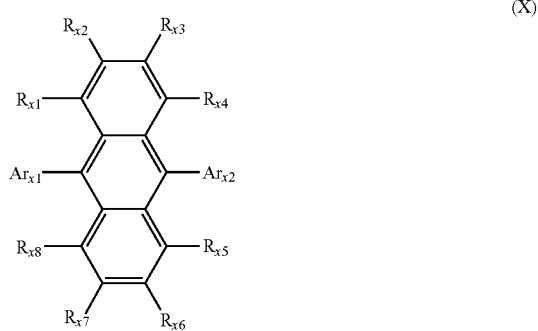

(X)

In the formula (X), $Ar_{X1}$ and $Ar_{X2}$ each independently represent a substituted or unsubstituted aryl group having 6 to 50 ring carbon atoms, or a substituted or unsubstituted heterocyclic group having 3 to 50 ring atoms. Preferably, $Ar_{X1}$ and $Ar_{X2}$ each independently represent a substituted or unsubstituted aryl group having 6 to 30 ring carbon atoms, or a heterocyclic group having 5 to 30 ring atoms.

A phosphorescent material (the dopant material) usable for the phosphorescent layer is exemplified by a metal complex such as an iridium complex, osmium complex, and platinum complex.

The phosphorescent material that is an ortho-metalated complex of a metal atom selected from the group consisting of iridium (Ir), osmium (Os) and platinum (Pt) is preferably a complex represented by a formula (α) below.

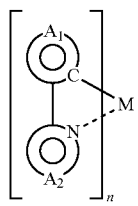

(α)

In the formula (α), M represents at least one metal selected from the group consisting of osmium, iridium, and platinum, and n represents a valence of the selected metal.

A ring $A_1$ represents a substituted or unsubstituted aryl group having 6 to 24 ring carbon atoms or a substituted or unsubstituted heteroaryl group having 5 to 30 ring atoms. A ring $A_2$ represents a substituted or unsubstituted heteroaryl group having 5 to 30 ring atoms and containing nitrogen as an atom forming a hetero ring.

The aryl group having 6 to 24 ring carbon atoms in the ring $A_1$ of the formula (α) is exemplified by the aryl group in the formula (1).

The heteroaryl group ring having 5 to 30 ring atoms in the rings $A_1$ and $A_2$ of the formula (α) is exemplified by the heteroaryl group in the formula (1).

The rings $A_1$ and $A_2$ of the formula (α) can have the same substituents as those in the formula (1).

Further preferably, the complex represented by the formula (α) is a complex represented by a formula (T) or (U) below.

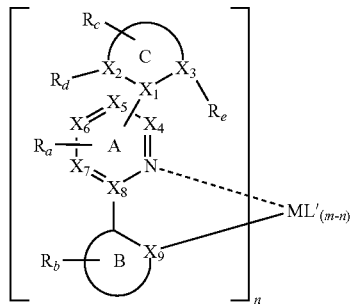

(T)

In the formula (T), M represents metal, and rings B and C each independently represent an aryl group or heteroaryl group having 5 or 6 ring atoms.

Ring A-Ring B represent a bonding pair of the ring A and an aryl or heteroaryl group and are coordinated with the metal M through a nitrogen atom of the ring A and an $sp^2$ composite atom of the ring B.

Ring A-Ring C represent a bonding pair of the ring A and an aryl or heteroaryl group.

$R_a$, $R_b$ and $R_c$ each independently represent one selected from the group consisting of a hydrogen atom, a substituted or unsubstituted alkyl group having 1 to 25 carbon atoms, a substituted or unsubstituted alkoxy group having 1 to 25 carbon atoms, a substituted or unsubstituted amino group, a substituted or unsubstituted alkenyl group having 2 to 25 carbon atoms, a substituted or unsubstituted alkynyl group having 2 to 25 carbon atoms, a substituted or unsubstituted aralkyl group having 7 to 50 carbon atoms, a substituted or unsubstituted aryl group having 6 to 24 ring carbon atoms, and a substituted or unsubstituted heteroaryl group having 5 to 30 ring atoms.

The number of $R_a$, $R_b$ and $R_c$ each independently ranges from 1 to 4.

$X_1$ to $X_9$ each independently represent a carbon atom or a nitrogen atom.

$R_d$ and $R_e$ each independently represent one selected from the group consisting of a hydrogen atom, a substituted or unsubstituted alkyl group having 1 to 25 carbon atoms, a substituted or unsubstituted alkoxy group having 1 to 25 carbon atoms, a substituted or unsubstituted amino group, a substituted or unsubstituted alkenyl group having 2 to 25 carbon atoms, a substituted or unsubstituted alkynyl group having 2 to 25 carbon atoms, a substituted or unsubstituted aralkyl group having 7 to 50 carbon atoms, a substituted or unsubstituted aryl group having 6 to 24 ring carbon atoms, and a substituted or unsubstituted heteroaryl group having 5 to 30 ring atoms. At least one of $R_c$, $R_d$ and $R_e$ bonded to the ring C is not a hydrogen atom.

m represents an oxidized state of the metal M. n is 1 or more. L' represents a mono-anionic bidentate ligand.

In the formula (T), M is exemplified by osmium, iridium and platinum, among which iridium is preferable.

The aryl group having 5 or 6 ring atoms represented by the ring B and the ring C is exemplified by the above-described aryl group in the formula (1).

The heteroaryl group having 5 or 6 ring atoms represented by the ring B and the ring C is exemplified by the above-described heteroaryl group in the formula (1).

The substituted or unsubstituted alkyl group having 1 to 25 carbon atoms, substituted or unsubstituted alkoxy group having 1 to 25 carbon atoms, substituted or unsubstituted aralkyl having 7 to 50 carbon atoms, substituted or unsubstituted aryl group having 6 to 24 ring carbon atoms, and substituted or unsubstituted heteroaryl group having 5 to 30 ring atoms represented by $R_1$, $R_2$, $R_a$, $R_b$ and $R_c$ are the same as those described above.

The substituted or unsubstituted alkenyl group having 2 to 25 carbon atoms and substituted or unsubstituted alkynyl group having 2 to 25 carbon atoms represented by $R_1$, $R_2$, $R_a$, $R_b$ and $R_c$ are the same as those described above.

The mono-anionic bidentate ligand represented by L' is exemplified by a ligand represented by a formula (L') below.

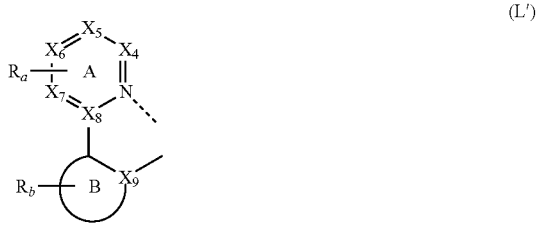

(L')

In the formula (L'), $X_4$ to $X_9$, $R_a$ and $R_b$ are the same as $X_4$ to $X_9$, $R_a$ and $R_b$ in the formula (T). Preferable examples of $X_4$ to $X_9$, $R_a$ and $R_b$ in the formula (L') are the same as those in the formula (T).

The ligand represented by the formula (L') is coordinated with the metal M represented in the formula (T) through a solid line extending from $X_9$ to an outside of the ring B and a dashed line extending from a nitrogen atom of the ring A to an outside of the ring A.

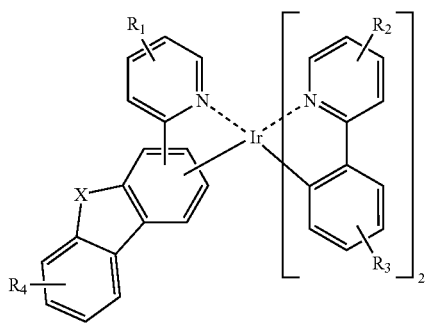

(U)

In the formula (U), X represents one selected from the group consisting of NR, an oxygen atom, a sulfur atom, BR, and a selenium atom. R represents a hydrogen atom or a substituted or unsubstituted alkyl group having 1 to 25 carbon atoms.

$R_1$, $R_2$, $R_3$ and $R_4$ each independently represent one selected from the group consisting of a hydrogen atom, a substituted or unsubstituted alkyl group having 1 to 25 carbon atoms and a substituted or unsubstituted aryl group having 6 to 24 ring carbon atoms. The number of $R_1$, $R_2$, $R_3$ and $R_4$ each independently ranges from 1 to 4.

In the formula (U), the alkyl group having 1 to 25 carbon atoms represented by R, $R_1$, $R_2$, $R_3$ and $R_4$ is exemplified by the above-described groups. Preferable examples of the alkyl group having 1 to 25 carbon atoms represented by R, $R_1$, $R_2$, $R_3$ and $R_4$ are the same as those described above.

Moreover, the aryl group having 6 to 24 ring carbon atoms represented by $R_1$, $R_2$, $R_3$ and $R_4$ is exemplified by the above-described groups. Preferable examples of the aryl group having 6 to 24 ring carbon atoms represented by $R_1$, $R_2$, $R_3$ and $R_4$ are the same as those described above.

The complex represented by the formula (T) or (U) is preferably compounds shown below, but is not limited thereto.

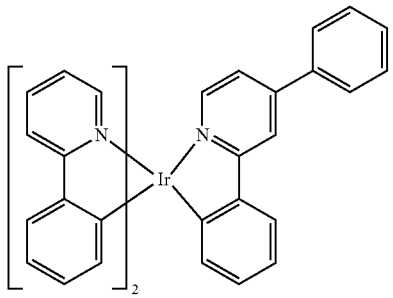

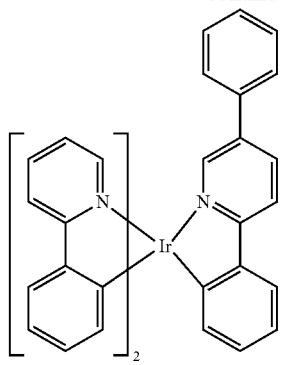

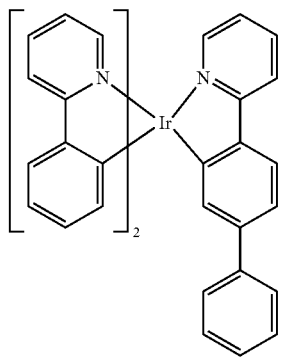

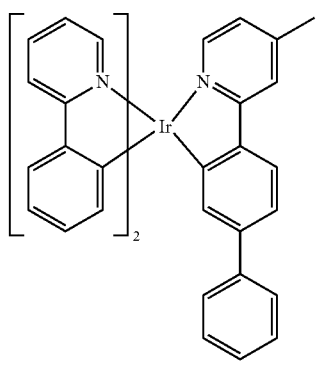

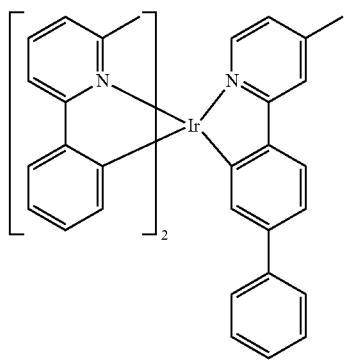

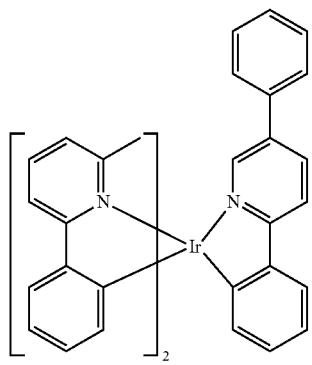
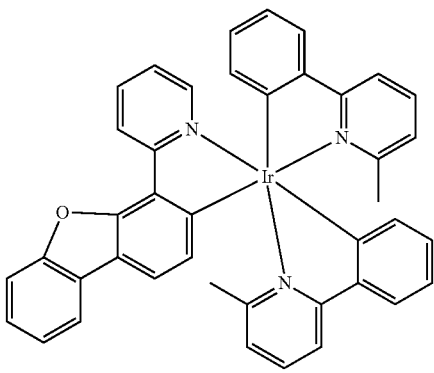
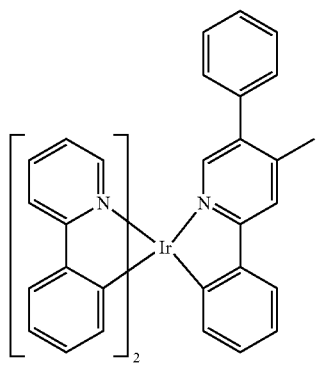
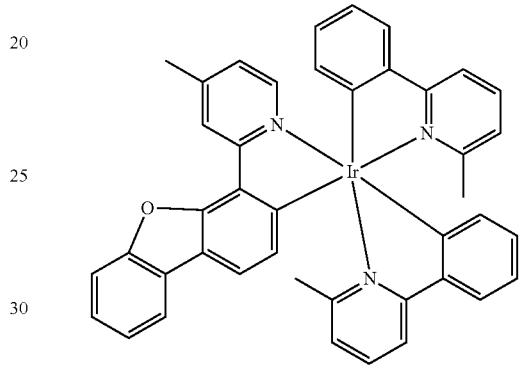
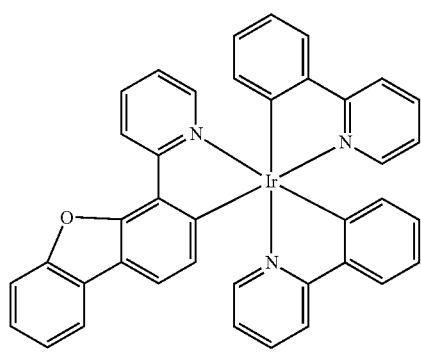
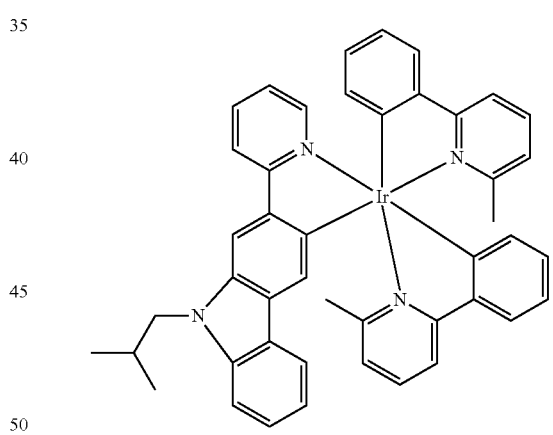
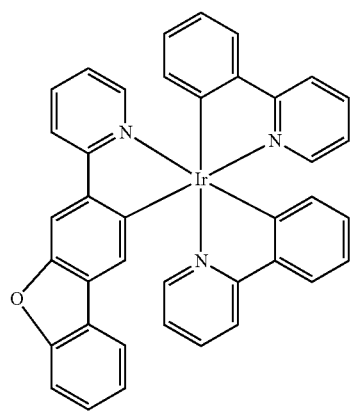
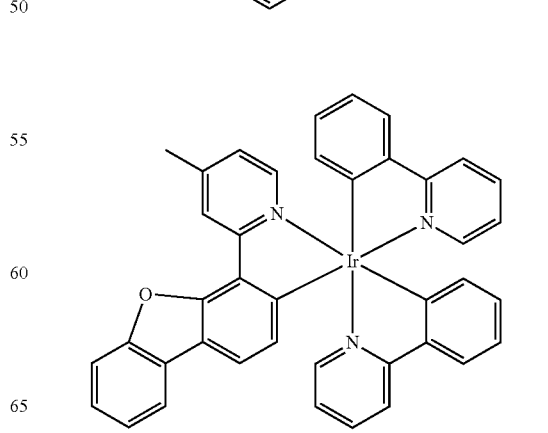

-continued

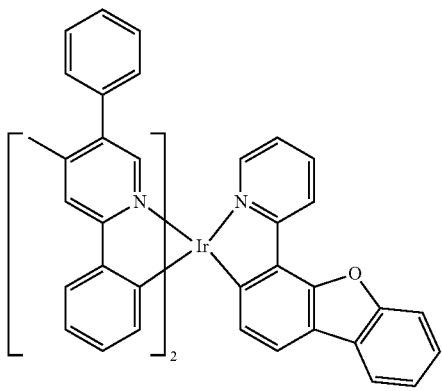

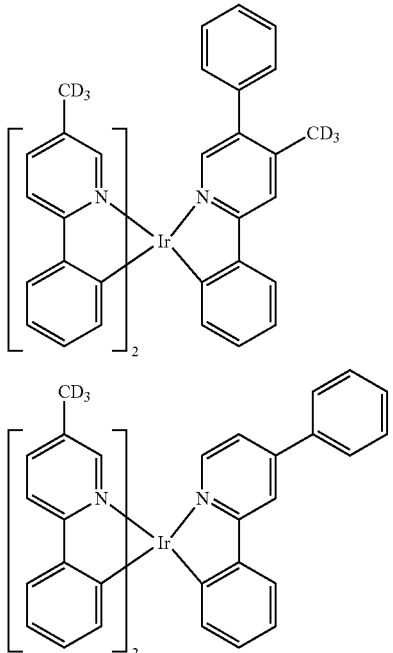

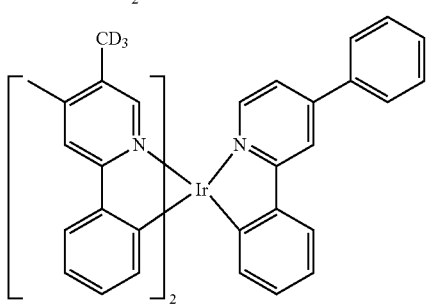

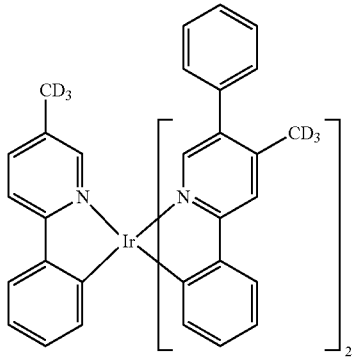

-continued

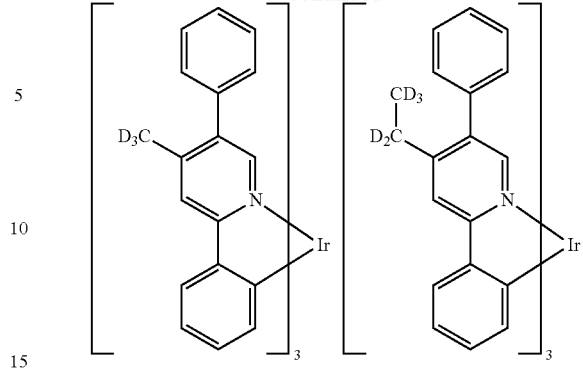

The phosphorescent material is also preferably an iridium complex represented by a formula (β) below.

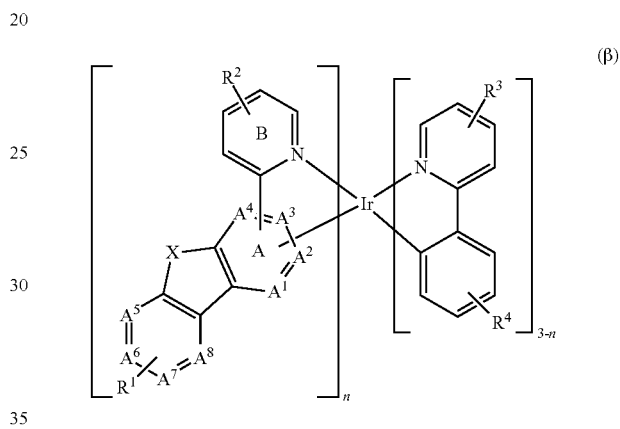

In the formula (β), $A^1$ to $A^8$ include a carbon atom or a nitrogen atom, at least one of $A^1$ to $A^8$ is a nitrogen atom, the ring B is bonded to the ring A by C—C bond, and iridium (Ir) is bonded to the ring A by Ir—C bond.

In the formula (β), only one of $A^1$ to $A^8$ is preferably a nitrogen atom, more preferably only one of $A^5$ to $A^8$ is a nitrogen atom, and further preferably $A^5$ is a nitrogen atom. In the formula (β), $A^3$ and $A^4$ of $A^1$ to $A^4$ are preferably carbon atoms. In the formula (β), it is preferable that $A^5$ is a nitrogen atom and $A^1$ to $A^4$ and $A^6$ to $A^8$ are carbon atoms.

$A^6$ is preferably CR (carbon atom bonded with R), in which R is selected from the group consisting of a substituted or unsubstituted alkyl group having 1 to 25 carbon atoms, a substituted or unsubstituted cycloalkyl group having 3 to 25 ring carbon atoms, and a combination thereof. R is preferably a substituted or unsubstituted alkyl group having 1 to 25 carbon atoms or a substituted or unsubstituted cycloalkyl group having 3 to 25 ring carbon atoms.

In the formula (β), X is O, S or Se, preferably O.

In the formula (β), $R^1$ to $R^4$ are each independently mono-substituted, di-substituted, tri-substituted, tetra-substituted, or unsubstituted. Adjacent ones of $R^1$ to $R^4$ are optionally bonded to each other to form a ring. $R^1$ to $R^4$ are each independently selected from the group consisting of hydrogen, deuterium, halogen, a substituted or unsubstituted alkyl group having 1 to 25 carbon atoms, a substituted or unsubstituted cycloalkyl group having 3 to 25 ring carbon atoms, a substituted or unsubstituted heteroalkyl group having 2 to 25 atoms, a substituted or unsubstituted arylalkyl group having 7 to 50 carbon atoms, a substituted or unsubstituted alkoxy group having 1 to 25 carbon atoms, a substituted or unsubstituted aryloxy group having 6 to 24 ring carbon atoms, a substituted or unsubstituted amino group, a substituted silyl group, a substituted or unsubstituted alkenyl group having 2 to 25 carbon atoms, a cycloalkenyl group having 3 to 25 ring carbon atoms, a heteroalkenyl group having 3 to 25 atoms, an alkynyl group having 2 to 25 carbon atoms, an aryl group having 6 to 24 ring carbon atoms, a heteroaryl group having 5 to 30 ring atoms, an acyl group, a substituted carbonyl group, carboxylic acid, ester, a nitrile group, an isonitrile group, a sulfanyl group, a sulfinyl group, a sulfonyl group, a phosphino group, and a combination thereof. The substituted silyl group is a silyl group substituted by at least one group selected from the group consisting of an alkyl group having 1 to 25 carbon atoms and an aryl group having 6 to 24 ring carbon atoms. The substituted carbonyl group is a carbonyl group substituted by at least one group selected from the group consisting of an alkyl group having 1 to 25 carbon atoms and an aryl group having 6 to 24 ring carbon atoms. In the formula (β), it is preferable that $R^1$ to $R^4$ are each independently selected from the group consisting of hydrogen, deuterium, an alkyl group having 1 to 25 carbon atoms, and a combination thereof. At least one of $R^2$ and $R^3$ is preferably an alkyl group having 1 to 25 carbon atoms, in which the alkyl group is more preferably deuterated or partially deuterated.

In the formula (β), n is an integer of 1 to 3, preferably 1.

Examples of the iridium complex represented by the formula (β) are shown below, but the iridium complex is not limited to the examples.

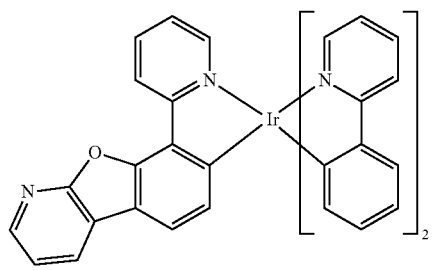

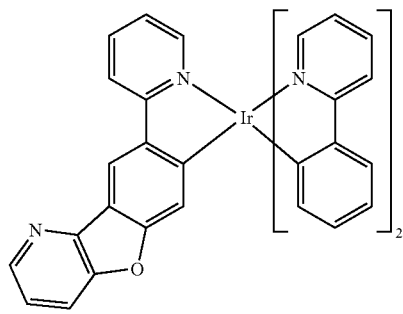

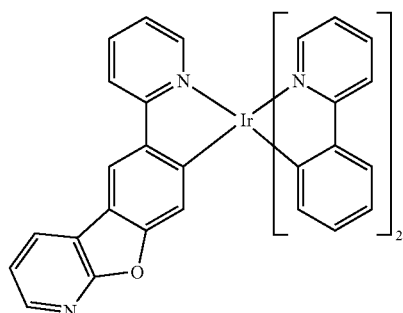

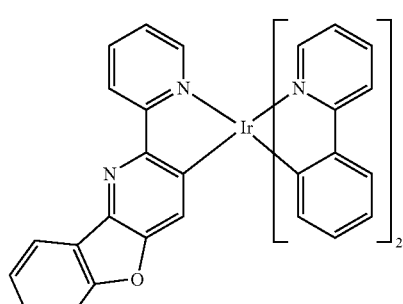

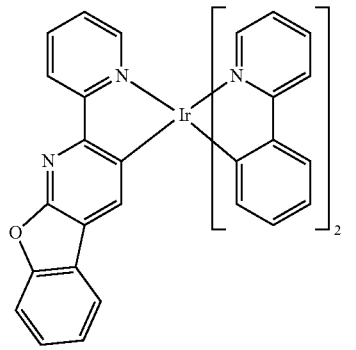

65
-continued
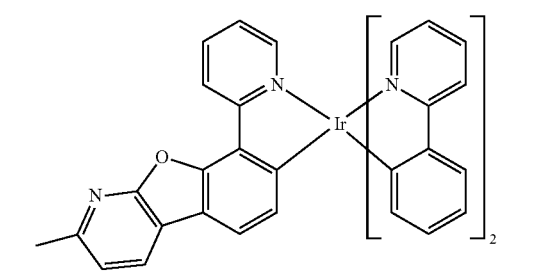
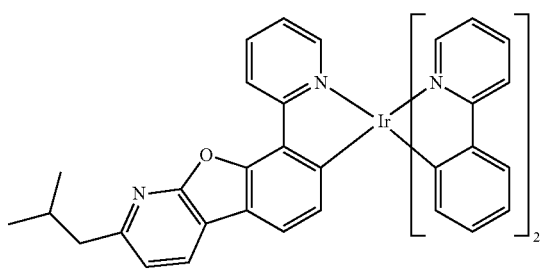
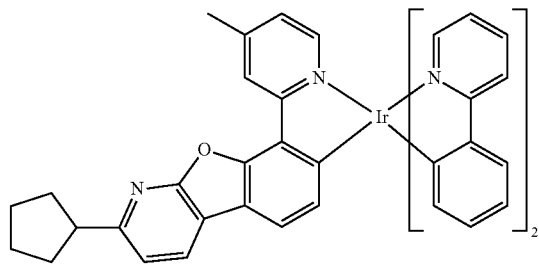
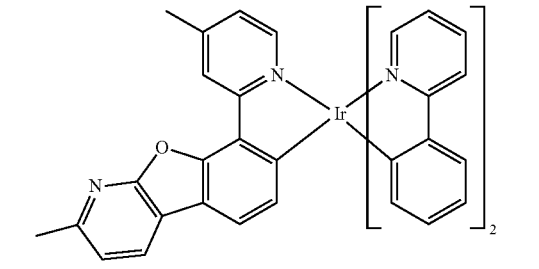
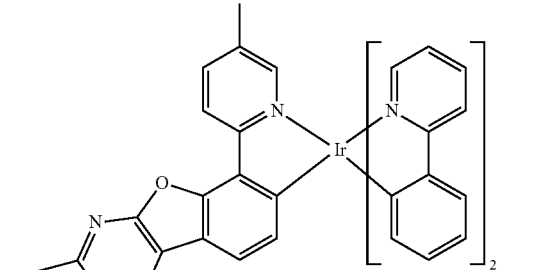
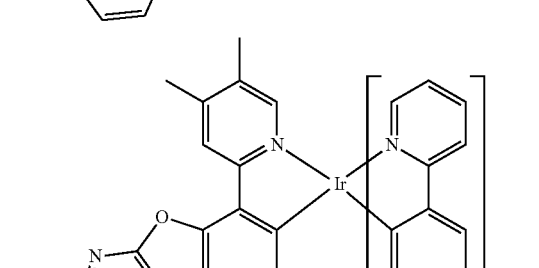
66
-continued
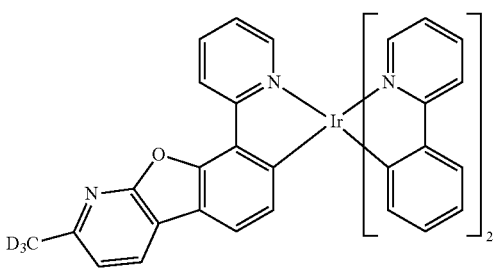
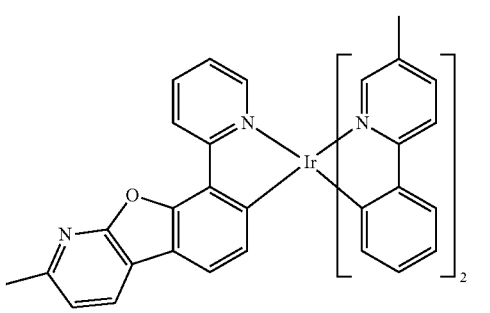
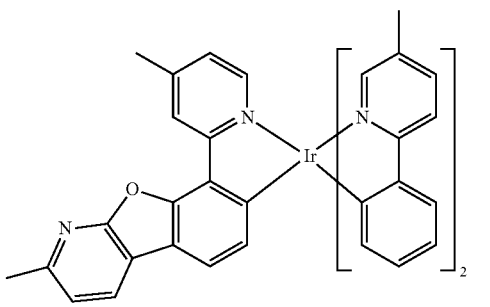
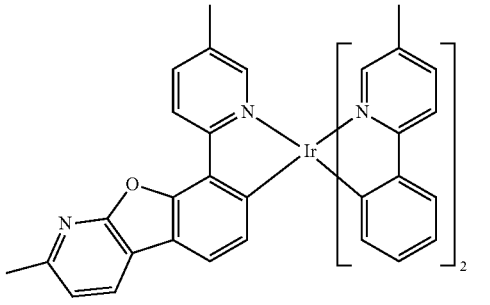
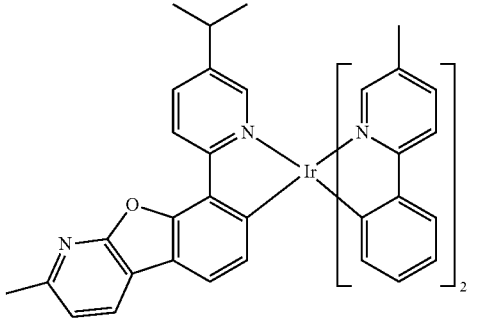

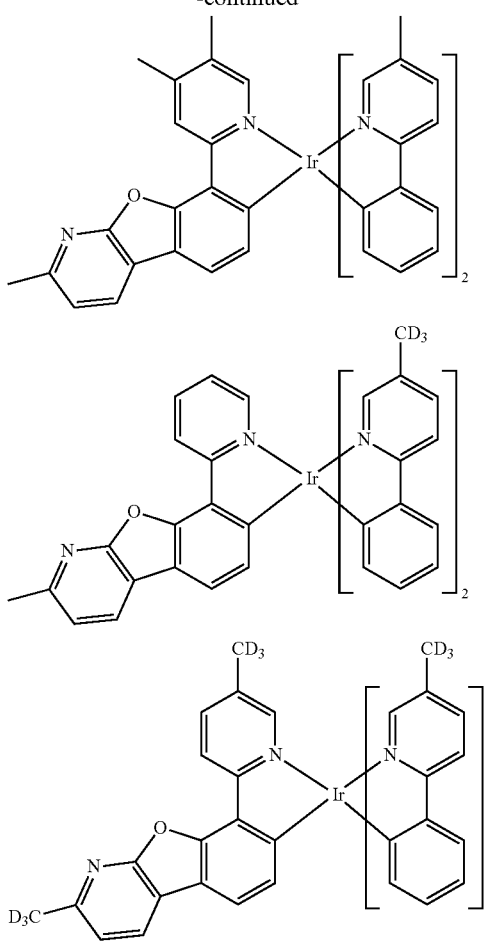

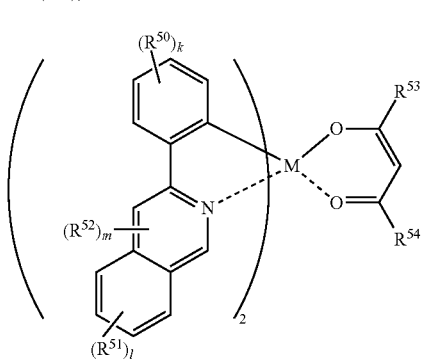

The complex represented by the formula (α) may be a complex represented by a formula (V), (X), (Y) or (Z) below in addition to the complex represented by the formula (T) or (U).

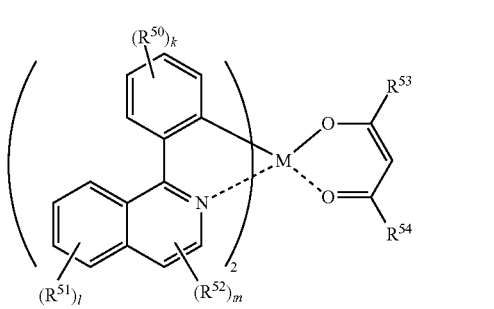

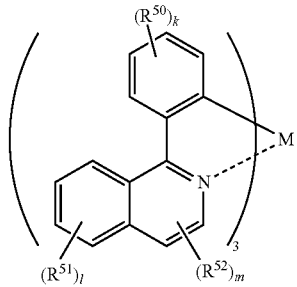

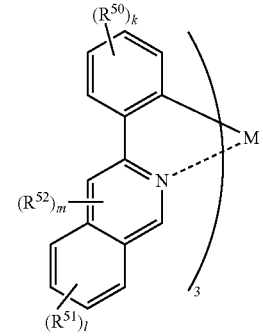

In the formula (V), (X), (Y) or (Z), $R^{50}$ to $R^{54}$ each independently represent a hydrogen atom or a substituent, k is an integer of 1 to 4, l is an integer of 1 to 4, and m is an integer of 1 to 2. M is Ir, Os, or Pt.

Examples of the substituent represented by $R^{50}$ to $R^{54}$ are the same substituent as those described above.

The formula (V) is preferably represented by a formula (V-1). The formula (X) is preferably represented by a formula (X-1) or (X-2). In the following formulae (V-1), (X-1) and (X-2), $R^{50}$, k and M represent the same as $R^{50}$, k and M described above.

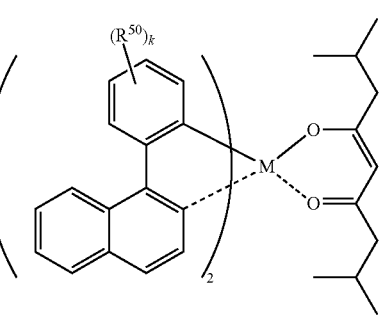

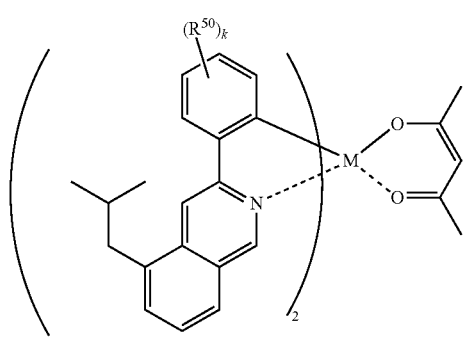
(X-2)
Examples of the complex represented by the formula (V), (X), (Y) or (Z) are shown below, but the complex is not limited to the examples.
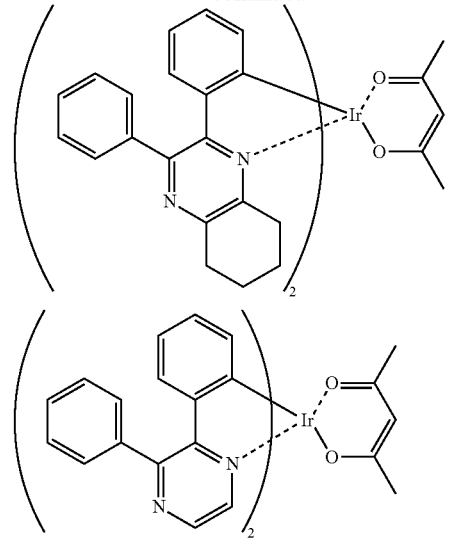
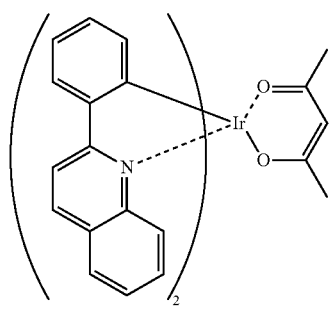
PqIr
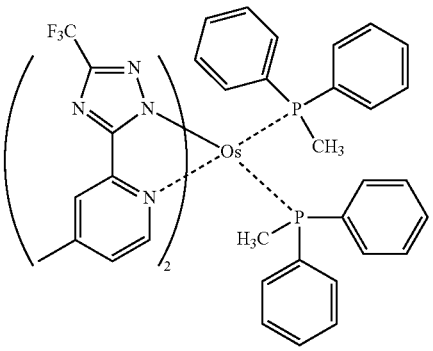
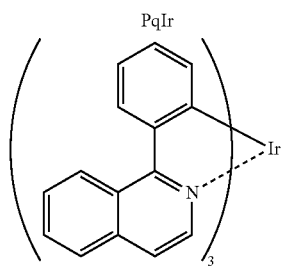
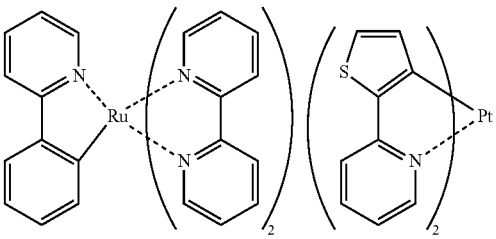
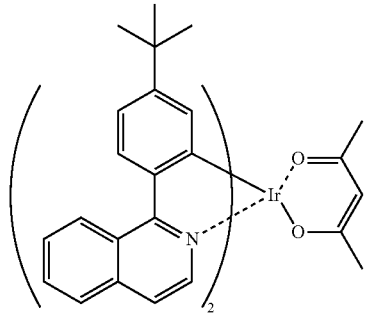
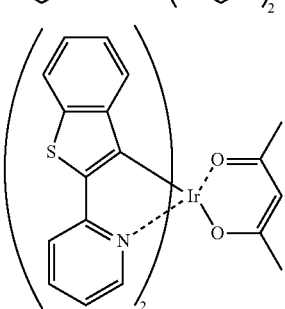
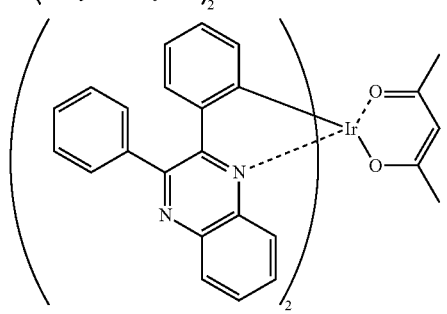
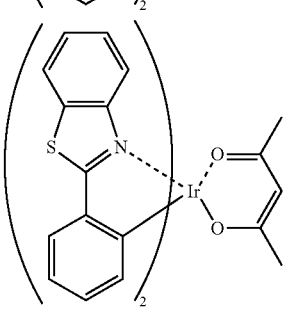

71
-continued
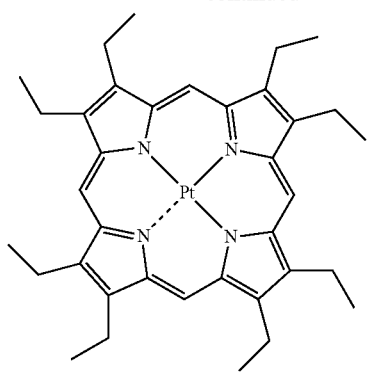
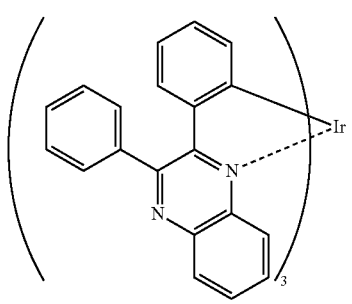
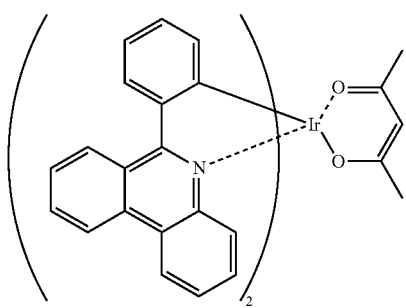
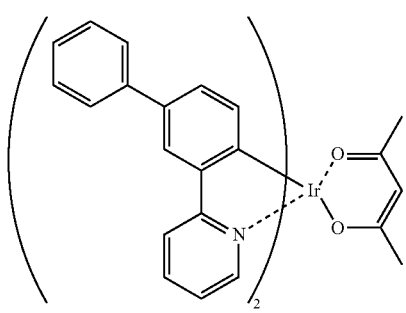
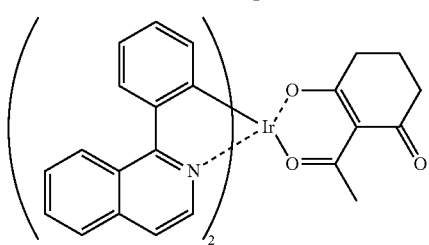
72
-continued
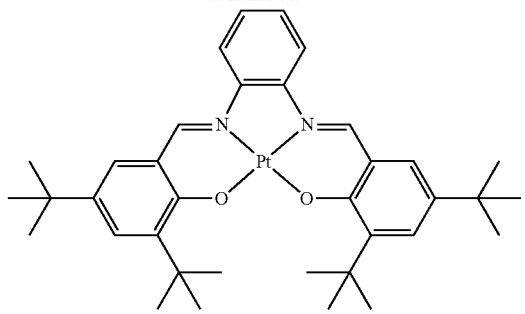
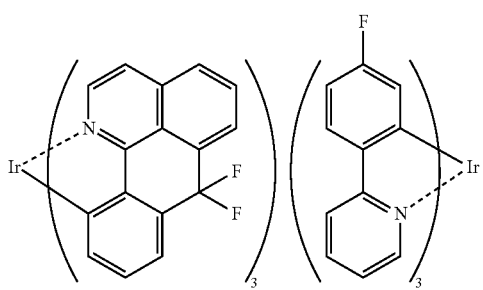
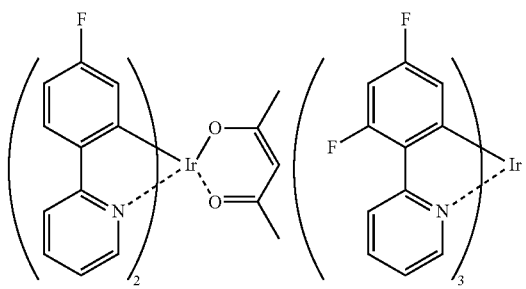
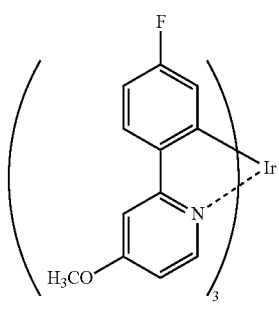
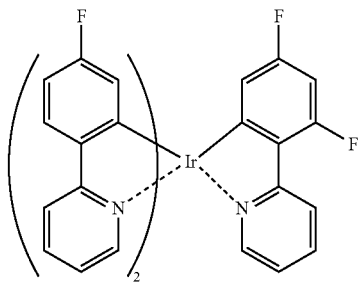

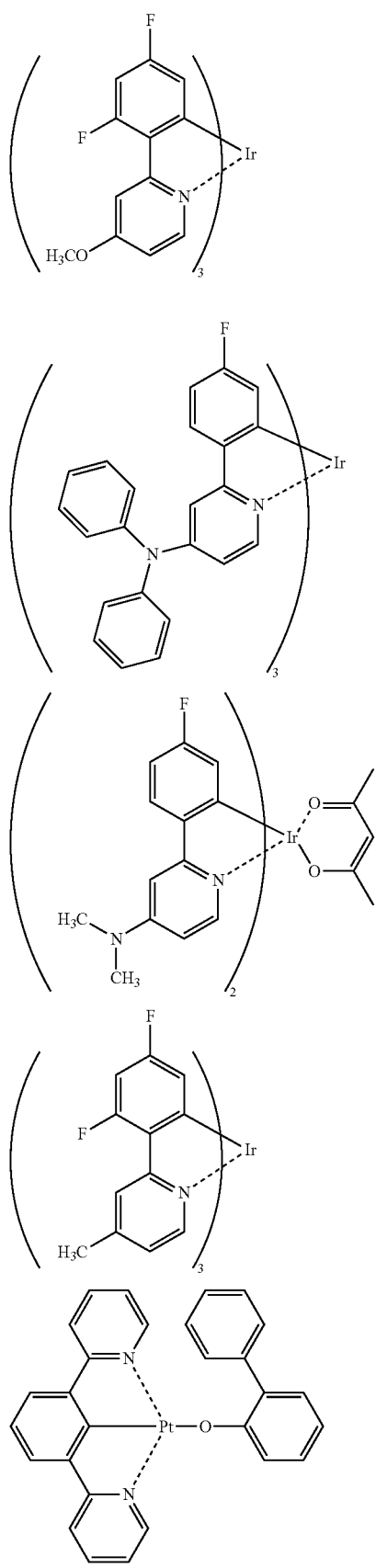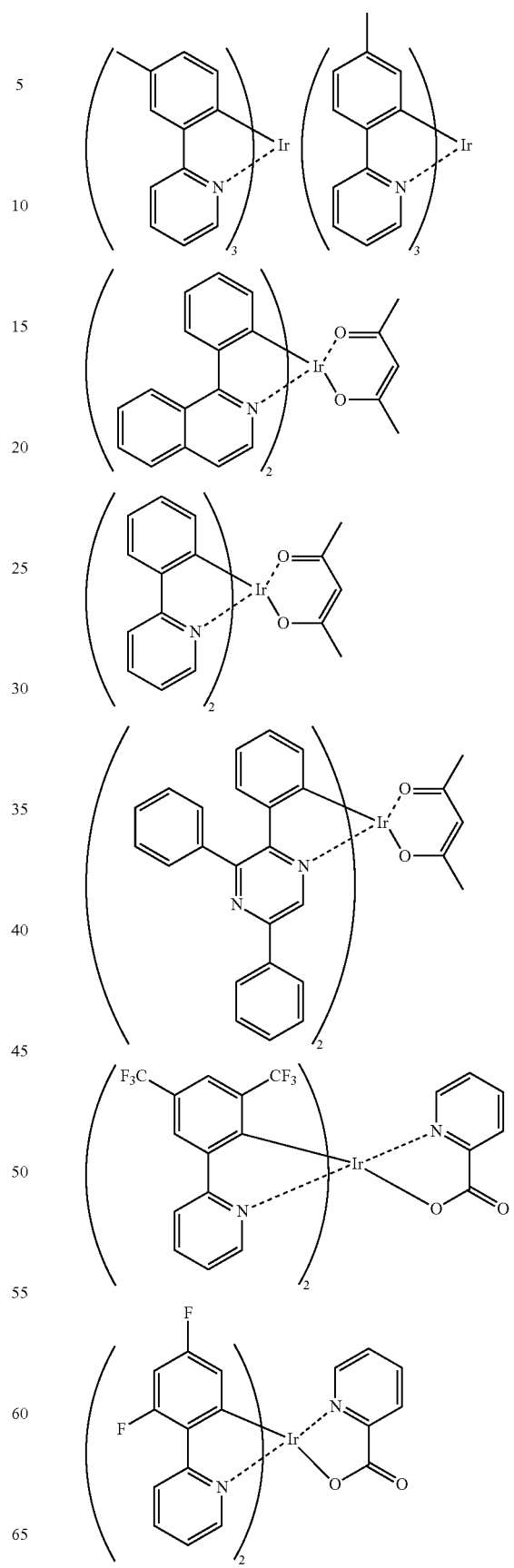

-continued
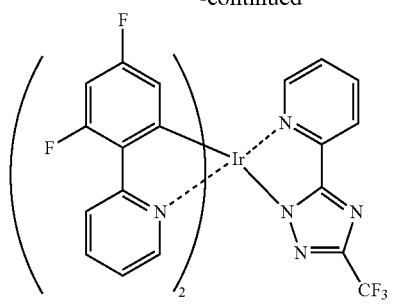
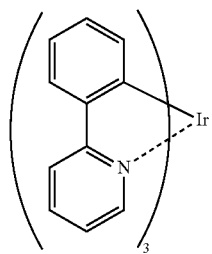
Ir(ppy)₃
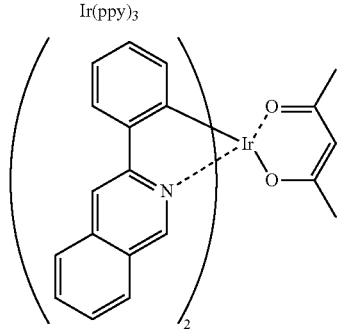
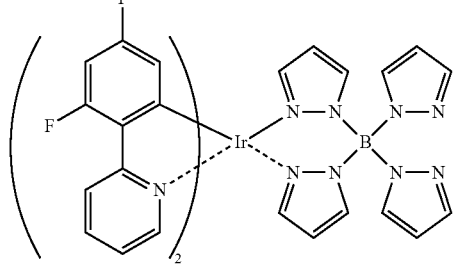
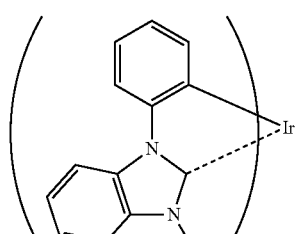
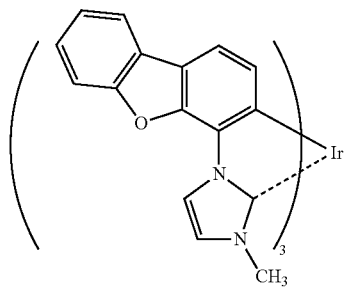
-continued
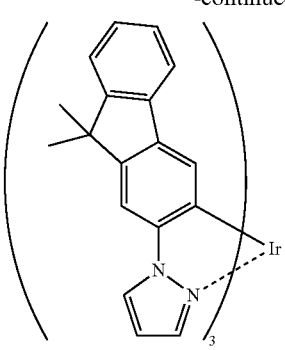
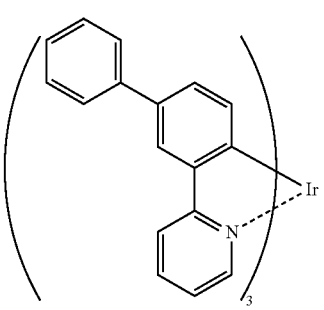
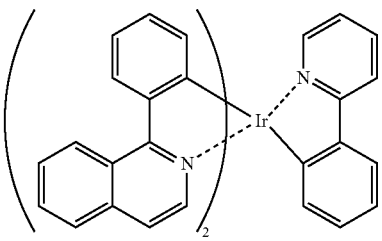
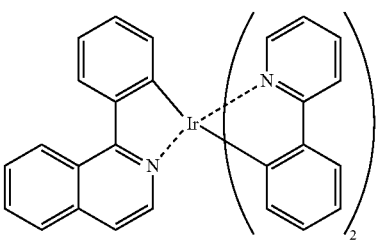
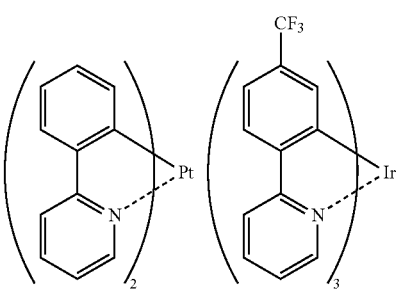
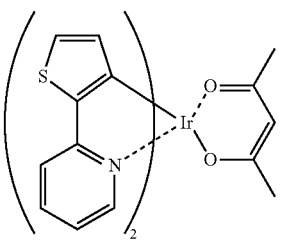

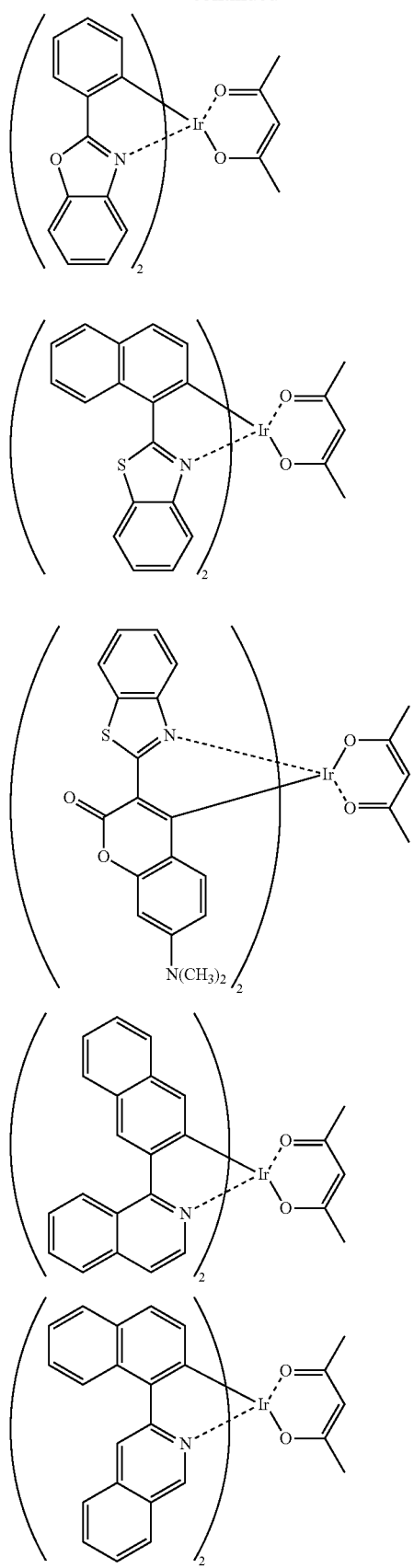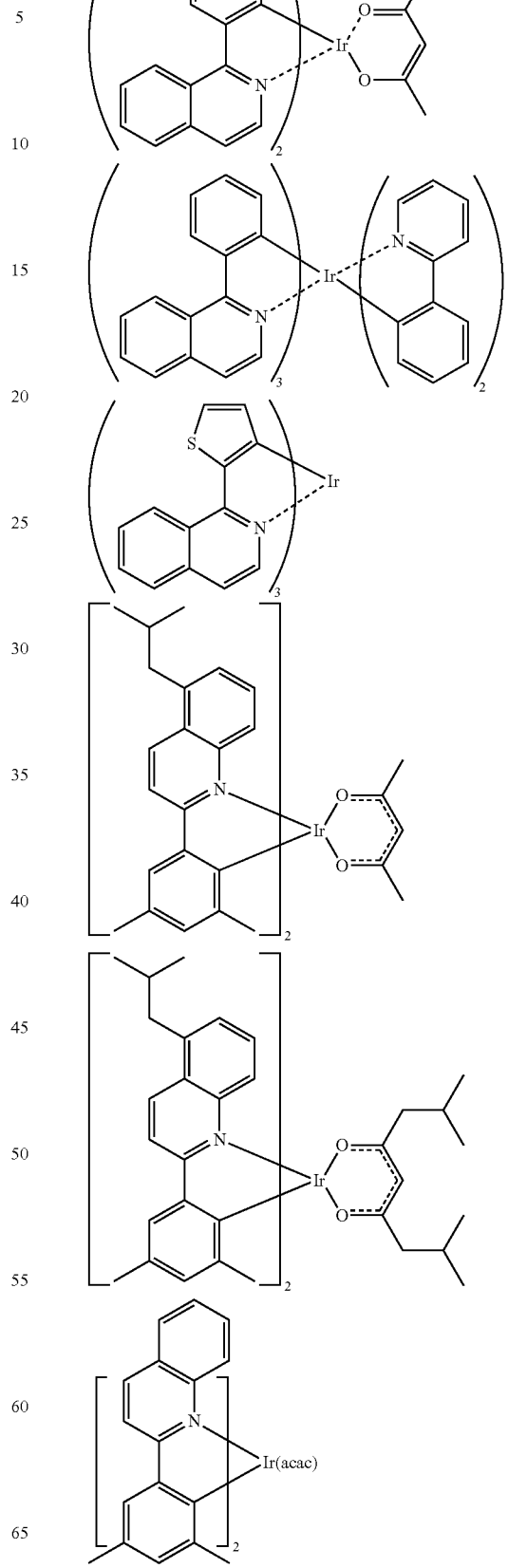

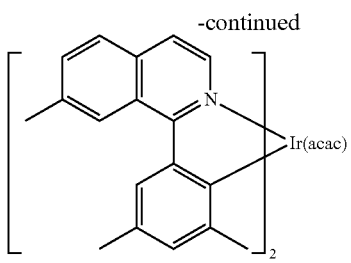

Host Material in Emitting Layer

The host material used in the phosphorescent layer is preferably a material having a higher triplet level than a phosphorescent dopant. A general phosphorescent host material such as an aromatic derivative, a heterocyclic derivative, and a metal complex is usable as the host material used in the phosphorescent layer. Among the examples of the host material used in the phosphorescent layer, an aromatic derivative and a heterocyclic derivative are preferable. Examples of the aromatic derivative include a naphthalene derivative, triphenylene derivative, phenanthrene derivative, and a fluoranthene derivative. Examples of the heterocyclic derivative include an indole derivative, carbazole derivative, pyridine derivative, pyrimidine derivative, triazine derivative, quinoline derivative, isoquinoline derivative, quinazoline derivative, dibenzofuran derivative, and dibenzothienyl derivative. Herein, the derivative is defined the same as described above.

The composition of the exemplary embodiment is a preferable example of the host material used in the phosphorescent layer.

Electron Transporting Layer

The electron transporting layer is a layer containing a highly electron-transporting substance.

At least one layer may be provided between the electron transporting layer and the emitting layer in order to improve the performance of the organic EL device. The at least one layer is referred to as a second electron transporting layer, hole blocking layer or triplet block layer. In order to improve hole blocking capability, a material having a deep HOMO level is preferably used. In order to improve triplet block capability, a material having a high triplet level is preferably used.

In the electron transporting layer, a metal complex such as an aluminum complex, beryllium complex and zinc complex; a hetero cyclic compound such as an imidazole derivative, benzimidazole derivative, azine derivative, carbazole derivative, and phenanthroline derivative; a fused aromatic hydrocarbon derivative; and a high-molecular compound are usable. Preferable examples of the material for the electron transporting layer include an imidazole derivative (e.g., a benzimidazole derivative, imidazopyridine derivative, and benzimidazophenanthridine derivative), an azine derivative (e.g., a pyrimidine derivative, triazine derivative, quinoline derivative, isoquinoline derivative, and phenanthroline derivative (i.e., a hetero ring), which may be substituted by a phosphine oxide substituent), and an aromatic hydrocarbon derivative (e.g., an anthracene derivative and fluoranthene derivative).

The composition of the exemplary embodiment is a preferable example of the material included in the electron transporting layer, the hole blocking layer or the triplet block layer.

As a preferable example, the electron transporting layer may include at least one selected from the group consisting of an alkali metal (e.g., Li and Cs), an alkaline earth metal (e.g., Mg), an alloy thereof, a derivative of the alkali metal (e.g., a lithium quinolinato complex), and a derivative of the alkaline earth metal. When the electron transporting layer includes at least one of the alkali metal, the alkaline earth metal, and the alloy thereof, a content ratio of the at least one included in the electron transporting layer is preferably in a range from 0.1 to 50 mass %, more preferably in a range from 0.1 to 20 mass %, further preferably in a range from 1 to 10 mass %. When the electron transporting layer includes at least one of the derivative of the alkali metal and the derivative of the alkaline earth metal, a content ratio of the at least one derivative included in the electron transporting layer is preferably in a range from 1 to 99 mass %, more preferably in a range from 10 to 90 mass %.

Electron Injecting Layer

The electron injecting layer is a layer containing a highly electron-injectable substance. Examples of a material for the electron injecting layer include an alkali metal, an alkaline earth metal, and an alloy thereof, examples of which include lithium (Li), lithium fluoride (LiF), cesium fluoride (CsF), calcium fluoride (CaF$_2$), and lithium oxide (LiOx), a derivative of the alkali metal (e.g., a lithium quinolinato complex), and a derivative of the alkaline earth metal.

Cathode

Metal, an alloy, an electrically conductive compound, a mixture thereof and the like, which have a small work function, specifically, of 3.8 eV or less, is preferably usable as a material for the cathode. Examples of the material for the cathode include elements belonging to Groups 1 and 2 in the periodic table of the elements, specifically, an alkali metal such as lithium (Li) and cesium (Cs), an alkaline earth metal such as magnesium (Mg), and an alloy (e.g., MgAg and AlLi) including the alkali metal or the alkaline earth metal, a rare earth metal, and an alloy including the rare earth metal.

Herein, a hydrogen atom encompasses isotopes having different numbers of neutrons, specifically, protium, deuterium and tritium.

Herein, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, the "ring carbon atoms" do not include carbon(s) contained in the substituent. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When the benzene ring and/or the naphthalene ring is substituted by, for instance, an alkyl group, the number of carbon atoms of the alkyl group is not included in the number of the ring carbon atoms. When a fluorene ring is substituted by, for instance, a fluorene ring (e.g., a spirofluorene ring), the number of carbon atoms of the fluorene ring as a substituent is not counted in the number of the ring carbon atoms for the fluorene ring.

Herein, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming a ring and atom(s) included in a substituent when the ring is substituted by the substituent are not counted in the number of the ring atoms. Unless specifically described, the same applies to the "ring atoms" described later. For instance, a pyridine ring has 6 ring atoms, a quinazoline ring has 10 ring atoms, and a furan ring has 5 ring atoms. Hydrogen atoms respectively bonded to the pyridine ring and the quinazoline ring and atoms forming the substituents are not counted in the number of the ring atoms. When a fluorene ring is substituted by, for instance, a fluorene ring (e.g., a spirofluorene ring), the number of atoms of the fluorene ring as a substituent is not counted in the number of the ring atoms for the fluorene ring.

Herein, "XX to YY carbon atoms" in the description of "a substituted or unsubstituted ZZ group having XX to YY carbon atoms" represent carbon atoms of an unsubstituted ZZ group and do not include carbon atoms of a substituent(s) of the substituted ZZ group.

Herein, "XX to YY atoms" in the description of "substituted or unsubstituted ZZ group having XX to YY atoms" represent atoms of an unsubstituted ZZ group and does not include atoms of a substituent(s) of the substituted ZZ group.

"Unsubstituted" in the description of "substituted or unsubstituted" herein means that a group is not substituted by the above-described substituents but bonded with a hydrogen atom.

Specific examples of each of the group in the formulae and specific examples of the substituent in the description of "substituted or unsubstituted" herein will be described.

Herein, the substituent in the description of "substituted or unsubstituted" is at least one group selected from the group consisting of an aryl group having 6 to 30 ring carbon atoms, heteroaryl group having 5 to 30 ring atoms, alkyl group (a linear or branched alkyl group) having 1 to 25 carbon atoms, cycloalkyl group having 3 to 25 ring carbon atoms, halogenated alkyl group having 1 to 25 carbon atoms, alkylsilyl group having 3 to 25 carbon atoms, arylsilyl group having 6 to 30 ring carbon atoms, alkoxy group having 1 to 25 carbon atoms, aryloxy group having 6 to 30 ring carbon atoms, heteroaryloxy group having 5 to 30 ring atoms, substituted amino group, alkylthio group having 1 to 25 carbon atoms, arylthio group having 6 to 30 ring carbon atoms, heteroarylthio group having 5 to 30 ring atoms, aralkyl group having 7 to 30 carbon atoms, alkyl group substituted by a heteroaryl group having 5 to 30 carbon atoms, alkenyl group having 2 to 30 carbon atoms, alkynyl group having 2 to 30 carbon atoms, phosphoryl group substituted by an aryl group having 6 to 30 carbon atoms or a heterocyclic group having 5 to 30 atoms, boryl group substituted by an aryl group having 6 to 30 carbon atoms or a heterocyclic group having 5 to 30 atoms, halogen atom, cyano group, hydroxyl group, nitro group, and carboxy group.

Herein, the substituent in the description of "substituted or unsubstituted" is preferably at least one group selected from the group consisting of an aryl group having 6 to 30 ring carbon atoms, heteroaryl group having 5 to 30 ring atoms, an alkyl group having 1 to 25 carbon atoms (a linear or branched alkyl group), alkylsilyl group having 3 to 25 carbon atoms, arylsilyl group having 6 to 30 ring carbon atoms, and cyano group, further preferably the preferable examples of each of the substituents in the description.

Herein, the substituent in the description of "substituted or unsubstituted" may be further substituted by at least one group selected from the group consisting of an aryl group having 6 to 30 carbon atoms, heteroaryl group having 5 to 30 ring atoms, alkyl group (a linear or branched alkyl group) having 1 to 25 carbon atoms, cycloalkyl group having 3 to 25 ring carbon atoms, alkylsilyl group having 3 to 25 carbon atoms, arylsilyl group having 6 to 30 ring carbon atoms, alkoxy group having 1 to 25 carbon atoms, aryloxy group having 6 to 30 ring carbon atoms, substituted amino group, alkylthio group having 1 to 25 carbon atoms, arylthio group having 6 to 30 ring carbon atoms, aralkyl group having 7 to 30 carbon atoms, alkenyl group having 2 to 30 carbon atoms, alkynyl group having 2 to 30 carbon atoms, halogen atom, cyano group, hydroxyl group, nitro group, and carboxy group. In addition, plural ones of these substituents may be mutually bonded to form a ring.

Herein, the substituent in the description of "substituted or unsubstituted" is preferably at least one group selected from the group consisting of an aryl group having 6 to 30 ring carbon atoms, heteroaryl group having 5 to 30 ring atoms, an alkyl group having 1 to 25 carbon atoms (a linear or branched alkyl group), halogen atom, and cyano group, further preferably the preferable examples of each of the substituents in the description.

Examples of the alkyl group include a methyl group, ethyl group, n-propyl group, isopropyl group, n-butyl group, isobutyl group, s-butyl group, t-butyl group, pentyl group (including an isomer group thereof), hexyl group (including an isomer group thereof), heptyl group (including an isomer group thereof), octyl group (including an isomer group thereof), nonyl group (including an isomer group thereof), decyl group (including an isomer group thereof), undecyl group (including an isomer group thereof), and dodecyl group (including an isomer group thereof). Among the examples, a methyl group, ethyl group, n-propyl group, isopropyl group, n-butyl group, isobutyl group, s-butyl group, t-butyl group and pentyl group (including an isomer group of each group) are preferable. A methyl group, ethyl group, n-propyl group, isopropyl group, n-butyl group, isobutyl group, s-butyl group and t-butyl group are more preferable. A methyl group, ethyl group, isopropyl group and t-butyl group are particularly preferable.

An alkyl group has 1 to 25 carbon atoms, preferably 1 to 10 carbon atoms.

A halogenated alkyl group provided by substituting the alkyl group with a halogen atom is exemplified by a halogenated alkyl group provided by substituting the alkyl group having 1 to 25 carbon atoms with one or more halogen atoms, preferably with a fluorine atom(s).

Specific examples of the halogenated alkyl group having 1 to 25 carbon atoms includes a fluoromethyl group, difluoromethyl group, trifluoromethyl group, fluoroethyl group, trifluoromethylmethyl group, trifluoroethyl group, and pentafluoroethyl group.

An alkenyl group is a group having a double bond in the above alkyl group and has 2 to 25 carbon atoms, preferably 2 to 10 carbon atoms. An alkenyl group is more preferably a vinyl group.

An alkynyl group is a group having a triple bond in the above alkyl group and has 2 to 25 carbon atoms, preferably 2 to 10 carbon atoms. The alkynyl group is more preferably an ethynyl group.

Examples of the cycloalkyl group are a cyclopropyl group, cyclobutyl group, cyclopentyl group, cyclohexyl group, cycloheptyl group, cyclooctyl group and adamantly group. Among the examples, a cyclopentyl group and a cyclohexyl group are preferable.

The cycloalkyl group has 3 to 25 ring carbon atoms, preferably 3 to 10 ring carbon atoms, more preferably 3 to 8 ring carbon atoms, further preferably 3 to 6 ring carbon atoms.

An alkoxy group is represented by —OY$^{10}$. Examples of Y$^{10}$ are the same as the examples of the alkyl group and the cycloalkyl group. The alkoxy group preferably has 1 to 25 carbon atoms, more preferably 1 to 10 carbon atoms.

An alkylthio group is represented by —SY$^{10}$. Examples of Y$^{10}$ are the same as the examples of the alkyl group and the cycloalkyl group.

The alkylthio group has 1 to 25 carbon atoms, preferably 1 to 10 carbon atoms.

Examples of the halogen atom include a fluorine atom, a chlorine atom, a bromine atom and a iodine atom, among which the fluorine atom is preferable.

Examples of the aryl group include a phenyl group, biphenylyl group, terphenylyl group, naphthyl group, acenaphthylenyl group, anthryl group, benzanthryl group, aceanthryl group, phenanthryl group, benzo[c]phenanthryl group, phenalenyl group, fluorenyl group, picenyl group, pentaphenyl group, pyrenyl group, chrysenyl group, benzo[g]chrysenyl group, s-indacenyl group, as-indacenyl group, fluoranthenyl group, benzo[k]fluoranthenyl group, triphenylenyl group, benzo[b]triphenylenyl group and perylenyl group. Among the examples, a phenyl group, biphenylyl group, terphenylyl group, naphthyl group, phenanthryl group, triphenylenyl group, fluoranthenyl group, and fluorenyl group are preferable. A phenyl group, biphenylyl group, and terphenylyl group are more are preferable. A phenyl group is further preferable.

The aryl group has 6 to 30 ring carbon atoms, preferably 6 to 24 ring carbon atoms, more preferably 6 to 20 ring carbon atoms, further preferably 6 to 18 ring carbon atoms.

An arylene group is a divalent group Y$^{21}$ provided by further removing one hydrogen atom or substituent from the above aryl group.

An aralkyl group is represented by —Y$^{11}$—Y$^{20}$. Y$^{11}$ is exemplified by a divalent group (an alkylene group or cycloalkylene group) provided by further removing one hydrogen atom or substituent from the above examples of the alkyl group and the cycloalkyl group. Y$^{20}$ is exemplified by the above aryl group.

An aryloxy group is represented by —OY$^{20}$. Examples of Y$^{20}$ are the same as the examples of the aryl group.

A heteroaryloxy group is represented by —OY$^{30}$. Examples of Y$^{30}$ are the same as the examples of the heteroaryl group.

An arylthio group is represented by —SY$^{20}$. Examples of Y$^{20}$ are the same as the examples of the aryl group.

A heteroarylthio group is represented by —SY$^{30}$. Examples of Y$^{30}$ are the same as the examples of the heteroaryl group.

An arylcarbonyloxy group is represented by —O—(C=O)—Y$^{20}$. Examples of Y$^{20}$ are the same as the examples of the aryl group.

A substituted carbonyl group having a substituent selected from an alkyl group and an aryl group is represented by —(C=O)—Y$^{10}$ or —(C=O)—Y$^{20}$. Examples of Y$^{10}$ are the same as the examples of the alkyl group and the cycloalkyl group. Examples of Y$^{20}$ are the same as the examples of the aryl group.

A heterocyclic group includes a heterocyclic group having no aromatic property and an aromatic heterocyclic group having an aromatic property (i.e., referred to as a heteroaryl group when the heterocyclic group is monovalent, and a heteroarylene group when the heterocyclic group is divalent).

Examples of the heterocyclic group having no aromatic property include a cyclic group having 3 to 30 ring atoms, preferably 3 to 20 ring atoms, including a nitrogen atom, oxygen atom and/or sulfur atom. Specific examples of the heterocyclic group having no aromatic property include aziridine, oxirane, thiirane, azetidine, oxetane, trimethylene sulfide, pyrrolidine, tetrahydrofuran, tetrahydrothiophene, piperidine, tetrahydropyrane, and tetrahydrothiopyrane.

The heterocyclic group is exemplified by a cyclic group including a hetero atom such as a nitrogen atom, oxygen atom, sulfur atom, and phosphorus atom. The ring atoms preferably include an atom selected from the group consisting of a nitrogen atom, oxygen atom and sulfur atom. The heterocyclic group is preferably a heteroaryl group having an aromatic property. Examples of the heteroaryl group includes a pyrrolyl group, furyl group, thienyl group, pyridyl group, imidazopyridyl group, pyridazynyl group, pyrimidinyl group, pyrazinyl group, triazinyl group, imidazolyl group, oxazolyl group, thiazolyl group, pyrazolyl group, isooxazolyl group, isothiazolyl group, oxadiazolyl group, thiadiazolyl group, triazolyl group, tetrazolyl group, indolyl group, isoindolyl group, benzofuranyl group, isobenzofuranyl group, benzothiophenyl group, isobenzothiophenyl group, indolizinyl group, quinolizinyl group, quinolyl group, isoquinolyl group, cinnolyl group, phthalazinyl group, quinazolinyl group, quinoxalinyl group, benzimidazolyl group, benzoxazolyl group, benzothiazolyl group, indazolyl group, benzisoxazolyl group, benzisothiazolyl group, dibenzofuranyl group, dibenzothiophenyl group, carbazolyl group, 9-phenylcarbazolyl group, phenanthridinyl group, acridinyl group, phenanthrolinyl group, phenazinyl group, phenothiazinyl group, phenoxazinyl group and xanthenyl group. Among the example, a pyridyl group, imidazopyridyl group, pyridazynyl group, pyrimidinyl group, pyrazinyl group, triazinyl group, benzimidazolyl group, dibenzofuranyl group, dibenzothiophenyl group, carbazolyl group, carbazolyl group substituted at a position 9 by an aryl group or a heterocyclic group, phenanthrolinyl group and quinazolinyl group are preferable.

The heterocyclic group has 3 to 30 ring atoms, preferably 5 to 24 ring atoms, more preferably 5 to 18 ring atoms.

The heteroaryl group has 5 to 30 ring atoms, preferably 5 to 24 ring atoms, more preferably 5 to 18 ring atoms.

The ring atoms of the heteroaryl group are preferably a nitrogen atom, oxygen atom or sulfur atom in addition to a carbon atom.

A heteroarylene group is a divalent group Y$^{31}$ provided by further removing one hydrogen atom or substituent from the above heteroaryl group.

Herein, the heterocyclic group may be a group derived from any one of partial structures represented by formulae (XY-1) to (XY-18) below.

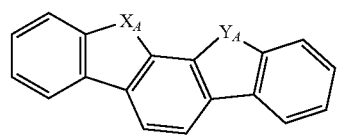

(XY-1)

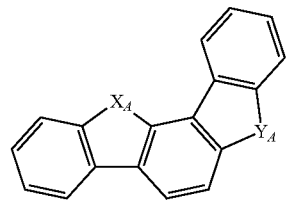

(XY-2)

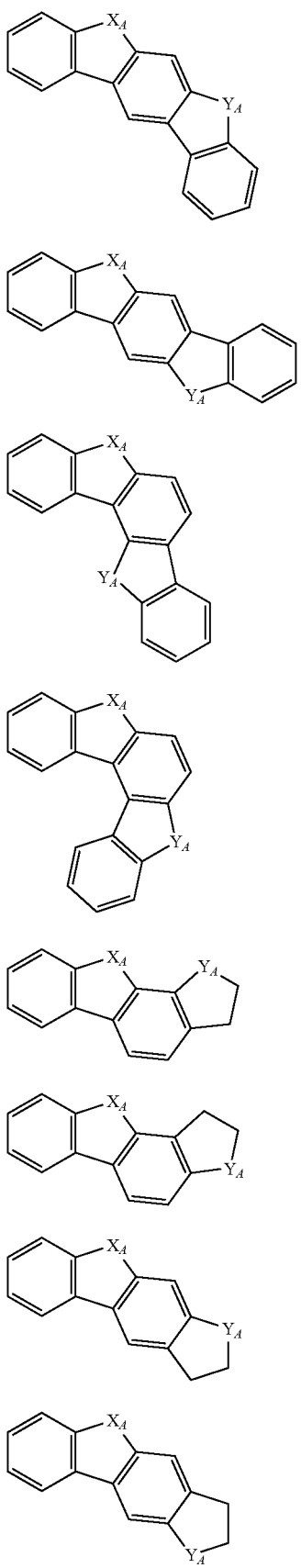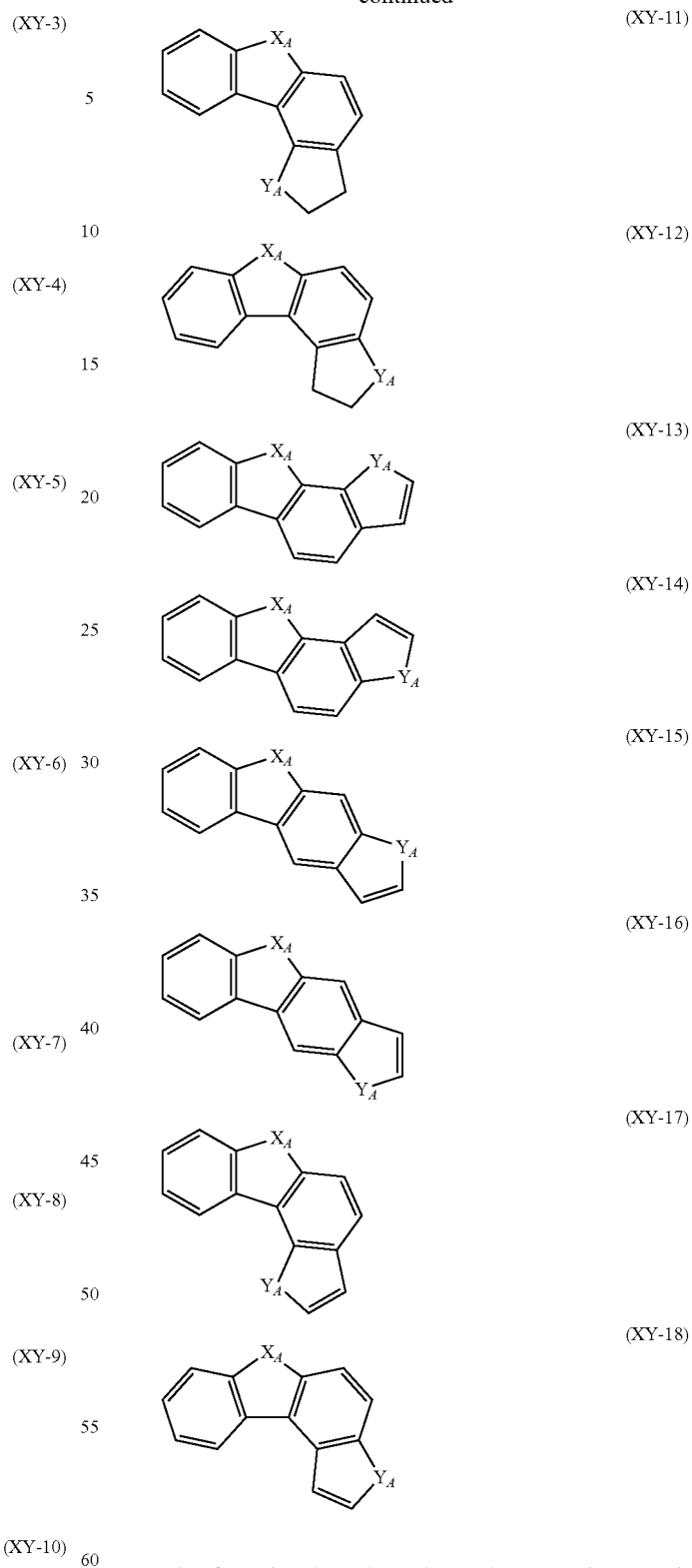
In the formulae (XY-1) to (XY-18), $X_A$ and $Y_A$ each independently represent a hetero atom, and preferably represent an oxygen atom, sulfur atom, selenium atom, silicon atom or germanium atom. The partial structures represented by the formulae (XY-1) to (XY-18) may each be bonded in any position to be a heterocyclic group, which may be substituted.

A mono-substituted amino group having a substituent selected from an alkyl group and aryl group is represented by —NH($Y^{10}$) or —NH($Y^{20}$), in which $Y^{10}$ and $Y^{20}$ are the same as the above.

A di-substituted amino group having substituents selected from an alkyl group and aryl group is represented by —N($Y^{10}$)$_2$—N($Y^{20}$)$_2$ or —N($Y^{10}$)($Y^{20}$) in which $Y^{10}$ and $Y^{20}$ are the same as the above. When two $Y^{10}$ or two $Y^{20}$ are present, the two $Y^{10}$ or two $Y^{20}$ may be mutually the same or different.

A mono-substituted silyl group having a substituent selected from an alkyl group and aryl group is represented by —SiH$_2$($Y^{10}$) or —SiH$_2$($Y^{20}$).

A di-substituted silyl group having substituents selected from an alkyl group and aryl group is represented by —SiH($Y^{10}$)$_2$, —SiH($Y^{20}$)$_2$ or —SiH($Y^{10}$)($Y^{20}$).

A tri-substituted silyl group having substituents selected from an alkyl group and aryl group is represented by —Si($Y^{10}$)$_3$, —Si($Y^{20}$)$_3$, —Si($Y^{10}$)$_2$($Y^{20}$) or —Si($Y^{10}$)($Y^{20}$)$_2$. $Y^{10}$ and $Y^{20}$ are the same as the above. When a plurality of $Y^{10}$ or a plurality of $Y^{20}$ are present, the plurality of $Y^{10}$ or the plurality of $Y^{20}$ may be mutually the same or different.

A substituted sulfonyl group having a substituent selected from an alkyl group and aryl group is represented by —S(=O)$_2$—$Y^{10}$ or —S(=O)$_2$—$Y^{20}$ in which $Y^{10}$ and $Y^{20}$ are the same as the above.

A di-substituted phosphoryl group having substituents selected from an alkyl group and aryl group is represented by —O—P(=O)($Y^{10}$)$_2$, —O—P(=O)($Y^{20}$)$_2$ or —O—P(=O)($Y^{10}$)($Y^{20}$). $Y^{10}$ and $Y^{20}$ are the same as the above. When two $Y^{10}$ or two $Y^{20}$ are present, the two $Y^{10}$ or the two $Y^{20}$ may be mutually the same or different.

An alkylsulphonyl group having an alkyl group is represented by —O—S(=O)$_2$($Y^{10}$), in which $Y^{10}$ is the same as the above.

An arylsulphonyloxy group having a substituent selected from an aryl group is represented by —O—S(=O)$_2$($Y^{20}$), in which $Y^{20}$ is the same as the above.

Electronic Device

An electronic device according to an exemplary embodiment of the invention includes the organic electroluminescence device of the above exemplary embodiment.

The organic electroluminescence device of the above exemplary embodiment is usable for various electronic devices. For example, the organic electroluminescence device of the above exemplary embodiment is usable for a light source of a flat light-emitting body, a backlight, instruments and the like, a display plate, sign lamp and the like. The flat light-emitting body is exemplified by a flat panel display of a wall-hanging TV. The backlight is exemplified by a backlight of a copier, a printer, a liquid crystal display and the like.

Moreover, the compound according to the exemplary embodiment is usable not only in the organic EL device but also in fields such as an electrophotographic photoreceptor, photoelectric conversion element, solar battery and image sensor.

Modification of Embodiments

It should be noted that the invention is not limited to the above exemplary embodiments but may include any modification and improvement as long as such modification and improvement are compatible with the invention.

In the above exemplary embodiment, the composition being contained in the emitting layer is exemplarily described. An organic EL device according to still another exemplary embodiment includes a composition in a single layer of the organic layer(s) except for the emitting layer. For instance, an organic EL device includes an anode, a cathode, an emitting layer provided between the anode and the cathode, and an electron transporting zone provided between the emitting layer and the cathode, in which the electron transporting zone includes the composition of the above exemplary embodiment.

For instance, the emitting layer is not limited to a single layer, but may be provided by laminating a plurality of emitting layers. When the organic EL device has a plurality of emitting layers, it is only required that at least one of the emitting layers satisfies the conditions described in the above exemplary embodiment. For instance, the rest of the emitting layer may be a fluorescent emitting layer or a phosphorescent emitting layer with use of emission by electron transfer from the triplet state directly to the ground state.

When the organic EL device includes a plurality of emitting layers, the plurality of emitting layers may be adjacent to each other, or provide a so-called tandem-type organic EL device in which a plurality of emitting units are layered through an intermediate layer.

For instance, a blocking layer may be provided adjacent to at least one side of a side near the anode and a side near the cathode of the emitting layer. The blocking layer is preferably provided in contact with the emitting layer to at least block holes, electrons or excitons.

For instance, when the blocking layer is provided in contact with the cathode-side of the emitting layer, the blocking layer permits transport of electrons, but blocks holes from reaching a layer provided near the cathode (e.g., the electron transporting layer) beyond the blocking layer. When the organic EL device includes the electron transporting layer, the blocking layer is preferably interposed between the emitting layer and the electron transporting layer.

When the blocking layer is provided in contact with the anode-side of the emitting layer, the blocking layer permits transport of holes, but blocks electrons from reaching a layer provided near the anode (e.g., the hole transporting layer) beyond the blocking layer. When the organic EL device includes the hole transporting layer, the blocking layer is preferably interposed between the emitting layer and the hole transporting layer.

Further, the blocking layer may be provided in contact with the emitting layer to prevent an excitation energy from leaking from the emitting layer into neighboring layers. The blocking layer blocks excitons generated in the emitting layer from moving into a layer provided near the electrode (e.g., the electron transporting layer and the hole transporting layer) beyond the blocking layer.

The emitting layer is preferably in contact with the blocking layer.

Specific structure and shape of the components in the present invention may be designed in any manner as long as the object of the present invention can be achieved.

EXAMPLE(S)

Example(s) of the invention will be described below. However, the invention is not limited to Example(s).

Compounds

Compounds used for manufacturing the organic EL device will be shown below.

HAT
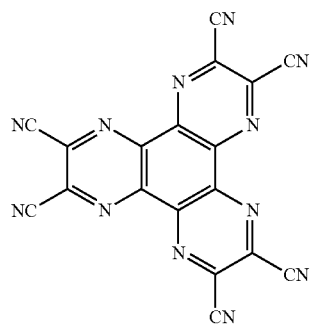
ET-1
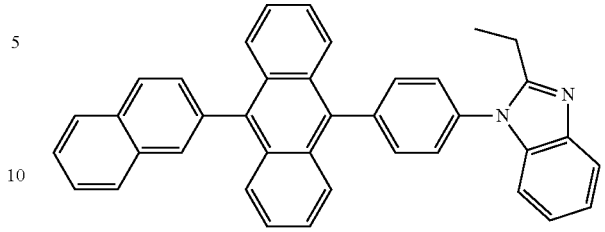
HT-1
PGH-P1
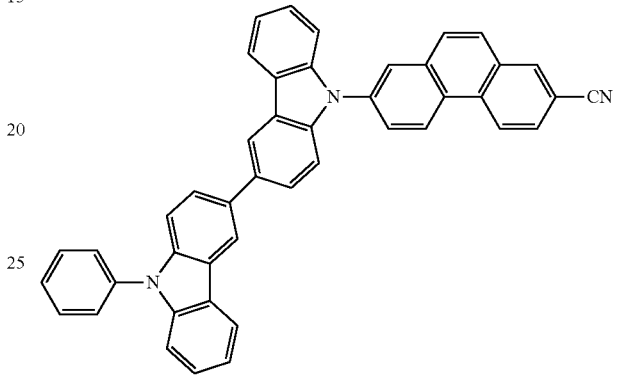
HT-2
PGH-N1
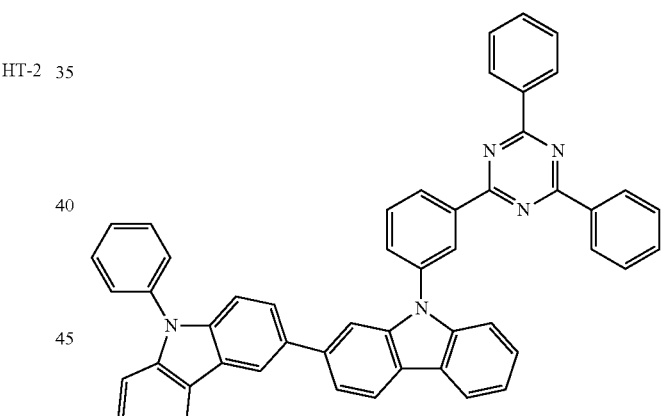
PGD-1
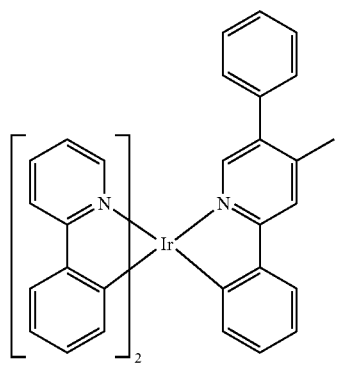
PGH-C1
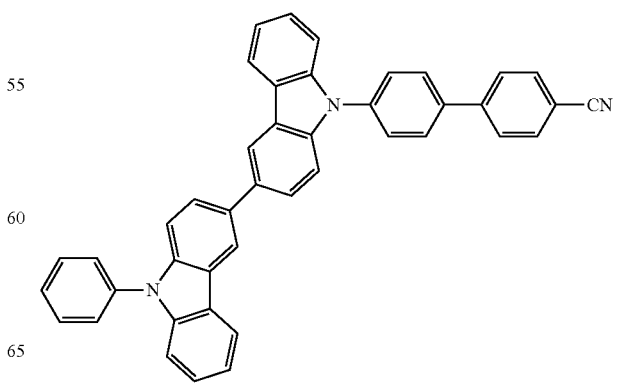

Manufacturing of Organic EL Device

The organic EL device was manufactured as follows.

Example 1

1.1 g of a compound PGH-P1 was measured. 1.1 g of a compound PGH-N1 was measured. The obtained two compounds were mixed in a mortar. After being mixed, 2 g of the obtained mixture was fed into a quartz crucible for a vacuum evaporator. A part of the mixture of the compound PGH-P1 and the compound PGH-N1 in the crucible was collected. The collected substance was dissolved in tetrahydrofuran. Based on a peak area value of each of components detected by HPLC (High Performance Liquid Chromatography), a ratio between the compound PGH-P1 and the compound PGH-N1 was measured to find that a mass ratio (initial ratio) was compound PGH-P1:compound PGH-N1=5:5.

The crucible filled with the compound PGH-P1 and the compound PGH-N1, a crucible filled with a compound HAT, a crucible filled with a compound HT-1, a crucible filled with a compound HT-2, a crucible filled with a compound PGD-1, a crucible filled with a compound ET-1, and a crucible filled with a 8-quinolinolato lithium (Liq) were set in the vacuum evaporator.

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was set to be 130-nm thick. After the glass substrate having the transparent electrode line was cleaned, the glass substrate was mounted on a substrate holder of the vacuum evaporator. Initially, a compound HAT was deposited on a first surface of the glass substrate where the transparent electrode line was provided in a manner to cover the transparent electrode while a second side of the glass substrate was protected by a mask, thereby forming a 10-nm thick HAT film of the compound HAT to form a hole injecting layer.

Next, on the hole injecting layer, a compound HT-1 was deposited to form a 110-nm thick HT-1 film, thereby providing a first hole transporting layer.

Next, on the first hole transporting layer, a compound HT-2 was deposited to form a 35-nm thick HT-2 film, thereby providing a second hole transporting layer.

Next, on the second hole transporting layer, the mixture of the compound PGH-P1 and the compound PGH-N1 were co-deposited with the compound PGD-1 to form a 40-nm-thick emitting layer. A concentration of the compound PGD-1 in the emitting layer was set at 5 mass %.

Subsequent to the formation of the emitting layer, the compound ET-1 and 8-quinolinolato lithium (Liq) were co-deposited at a mass ratio of 50:50 to form a 30-nm thick electron transporting layer.

Liq was deposited on the electron transporting layer to form a 1-nm thick electron injecting layer.

A metal Al was deposited on the electron injecting layer to form an 80-nm thick metal cathode.

The thus manufactured organic EL device was defined as an organic EL device at an evaporation initial stage.

After the organic EL device was manufactured, the ITO substrate was moved out of the chamber. The evaporation of the mixture of the compound PGH-P1 and the compound PGH-N1 was continued until the mass of the materials in the crucible reached 0.4 g (the residue of 20 mass %). Subsequently, the ITO substrate was returned in the chamber and the manufactured part of the organic EL device was protected by a mask. Subsequently, the compound HAT was deposited on the first surface of the glass substrate where the transparent electrode line was provided in a manner to cover the transparent electrode, thereby forming a 10-nm thick HAT film of the compound HAT to form the hole injecting layer.

Next, on the hole injecting layer, the compound HT-1 was deposited to form a 110-nm thick HT-1 film, thereby providing the first hole transporting layer.

Next, on the first hole transporting layer, the compound HT-2 was deposited to form a 35-nm thick HT-2 film, thereby providing the second hole transporting layer.

Next, on the second hole transporting layer, the mixture of the compound PGH-P1 and the compound PGH-N1 were co-deposited with the compound PGD-1 to form a 40-nm-thick emitting layer. A concentration of the compound PGD-1 in the emitting layer was set at 5 mass %.

Subsequent to the formation of the emitting layer, the compound ET-1 and 8-quinolinolato lithium (Liq) were co-deposited at the mass ratio of 50:50 to form a 30-nm thick electron transporting layer.

Liq was deposited on the electron transporting layer to form a 1-nm thick electron injecting layer.

A metal Al was deposited on the electron injecting layer to form an 80-nm thick metal cathode.

The thus manufactured organic EL device was defined as an organic EL device at an evaporation terminal stage.

Lastly, the residue in the crucible was taken out of the evaporator and was dissolved in tetrahydrofuran. Based on a peak area value of each of components detected by HPLC, the ratio (residual ratio) between the compound PGH-P1 and the compound PGH-N1 was calculated.

Table 1 shows the ratio (initial ratio) between the first compound and the second compound in the crucible in the initial stage (before the evaporation) and the ratio (residual ratio) between the first compound and the second compound in the crucible after evaporation.

Comparative 1

An organic EL device of Comparative 1 was manufactured in the same manner as the organic EL device of Example 1 except for using a compound PGH-C1 in place of the PGH-P1.

TABLE 1

|  | First Compound | Second Compound | Material Ratio in Crucible | |
| --- | --- | --- | --- | --- |
|  |  |  | Initial Ratio | Residual Ratio |
| Example 1 | PGH-N1 | PGH-P1 | 5:5 | 5:5 |
| Comparative 1 | PGH-N1 | PGH-C1 | 5:5 | 2:8 |

In the organic EL device in the evaporation initial stage in Example 1, the mass ratio (film ratio) between the compound PGH-P1 and the compound PGH-N1 in the emitting layer was analyzed by HPLC to find the compound PGH-P1:compound PGH-N1=5:5.

In the organic EL device in the evaporation initial stage in Comparative 1, the mass ratio (film ratio) between the compound PGH-C1 and the compound PGH-N1 in the emitting layer was analyzed by HPLC to find the compound PGH-C1:compound PGH-N1=8:2.

With respect to the organic EL device of Example 1 (at the initial stage), the mass ratio (film ratio) between the first compound and the second compound in the emitting layer was the same as the mass ratio (initial ratio) between the first compound and the second compound in the crucible at the initial stage (before the evaporation).

However, with respect to the organic EL device of Comparative 1 (at the initial stage), the mass ratio (film ratio) between the first compound and the second compound in the emitting layer was significantly different from the mass ratio (initial ratio) between the first compound and the second compound in the crucible at the initial stage (before the evaporation). In Comparative 1, the first compound and the second compound were mixed at the mass ratio of 5:5 in the crucible. However, the mass ratio between the first compound and the second compound in the film was at 8:2, which showed that the mass ratio between the first compound and the second compound in the emitting layer was not the same ratio as the ratio of the used materials.

Evaluation of Organic EL Devices

The manufactured organic EL devices in the evaporation initial stage and the evaporation terminal stage in Example 1 and Comparative 1 were evaluated as follows. The evaluation results are shown in Table 2.

Drive Voltage V

Voltage was applied between the ITO transparent electrode and the metal Al cathode such that a current density was 10 mA/cm², where the voltage (unit: V) was measured.

External Quantum Efficiency EQE

Voltage was applied on each of the organic EL devices such that a current density was 10 mA/cm², where spectral radiance spectra were measured by a spectroradiometer CS-1000 (manufactured by Konica Minolta, Inc.). The external quantum efficiency EQE (unit: %) was calculated based on the obtained spectral-radiance spectra, assuming that the spectra was provided under a Lambertian radiation.

Lifetime LT97

A continuous direct current test was conducted at the initial current density of 10 mA/cm². An elapsed time until the luminance was decreased to 97% from the luminance at the start of the test was measured. The measured time was defined as a lifetime LT97 (unit: time (hrs)).

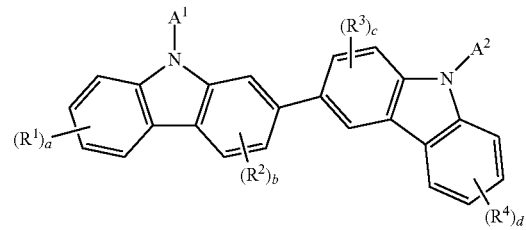

where: $R^1$ to $R^4$ each independently represent a halogen atom, a substituted or unsubstituted alkyl group having 1 to 25 carbon atoms, a substituted or unsubstituted cycloalkyl group having 3 to 25 ring carbon atoms, a substituted or unsubstituted aryl group having 6 to 18 ring carbon atoms, a substituted or unsubstituted heterocyclic group having 6 to 18 ring atoms, a silyl group substituted by at least one group selected from the group consisting of an alkyl group having 1 to 25 carbon atoms and an aryl group having 6 to 18 ring carbon atoms, or a cyano group;

a is 0, 1, 2, 3 or 4;
b is 0, 1, 2 or 3;
c is 0, 1, 2 or 3;
d is 0, 1, 2, 3 or 4;
a plurality of $R^1$ are mutually the same or different when a is 2 or more;
a plurality of $R^2$ are mutually the same or different when b is 2 or more;
a plurality of $R^3$ are mutually the same or different when c is 2 or more;
a plurality of $R^4$ are mutually the same or different when d is 2 or more;
$A^1$ and $A^2$ each independently represent a substituted or unsubstituted aryl group having 6 to 24 ring carbon atoms, or a substituted or unsubstituted heterocyclic group having 6 to 24 ring atoms; and

TABLE 2

|  | First Compound | Second Compound | Organic EL device | Voltage (V) | EQE (%) | LT97 (hrs) |
|---|---|---|---|---|---|---|
| Example 1 | PGH-N1 | PGH-P1 | Evaporation initial stage | 4.66 | 20.2 | 100 |
|  |  |  | Evaporation terminal stage | 4.65 | 20.1 | 100 |
| Comparative 1 | PGH-N1 | PGH-C1 | Evaporation initial stage | 5.35 | 17.5 | 100 |
|  |  |  | Evaporation terminal stage | 4.88 | 18.9 | 40 |

With respect to the organic EL devices in the evaporation initial stage and the evaporation terminal stage in Example 1 and Comparative 1, it was observed that the organic EL devices of Example 1 exhibited less variable performance than those of Comparative 1. It is found that use of the composition containing the first compound represented by the formula (1) and the second compound represented by the formula (2) allows evaporation at a stable material ratio from a single evaporation source while maintaining a performance of an organic electroluminescence device.

What is claimed is:

1. A composition comprising: a mixture of at least two compounds,
the at least two compounds comprising a first compound represented by a formula (1) and a second compound represented by a formula (5) below, $R^1$ to $R^4$, $A^1$ and $A^2$ comprise five cyclic structures in total each represented by a formula (1a) below,

where: $X^1$, $X^2$ and $X^3$ each independently represent $CR^X$ or a nitrogen atom; in at least one cyclic structure of the five cyclic structures each represented by the formula (1a), at least one of $X^1$, $X^2$ and $X^3$ is a nitrogen atom;

the cyclic structures each represented by the formula (1a) are bonded to each other to form a fused ring, or are not bonded;

$R^X$, $R^{X1}$, $R^{X2}$ and $R^{X3}$ each independently represent a single bond, a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group;

when a plurality of $R^X$ are present, the plurality of $R^X$ are mutually the same or different; and at least one of $R^{X1}$, $R^{X2}$, $R^{X3}$ and one or more $R^X$ is a single bond,

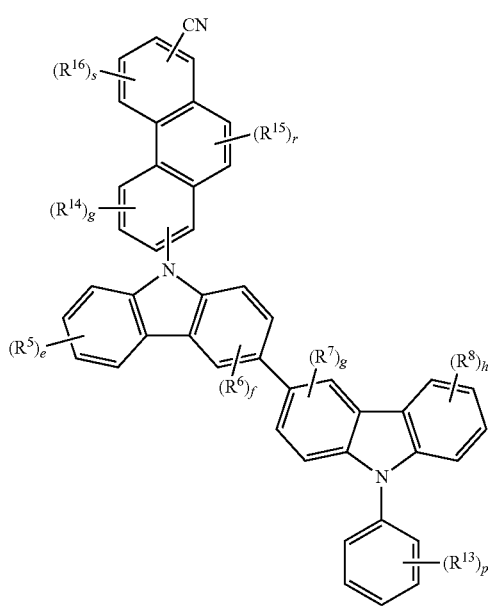

(5)

where: $R^5$ to $R^8$ and $R^{13}$ to $R^{16}$ each independently represent: a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group;

e is 0;
f is 0;
g is 0;
h is 0;
p is 0;
q is 0;
r is 0; and
s is 0.

2. The composition according to claim 1, wherein
a, b, c and d are 0.

3. The composition according to claim 1, wherein
the first compound is a compound represented by a formula (3) below,

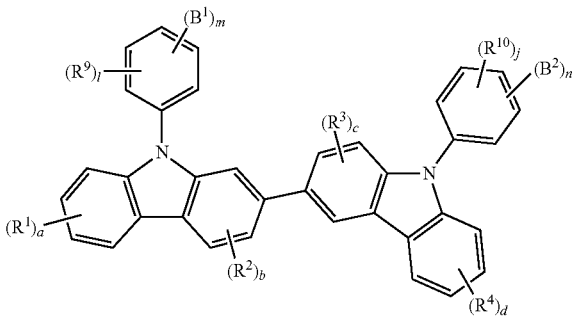

(3)

where: $R^1$ to $R^4$, $R^9$ and $R^{10}$ each independently represent a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group;

a is 0, 1, 2, 3 or 4;
b is 0, 1, 2 or 3;
c is 0, 1, 2 or 3;
d is 0, 1, 2, 3 or 4;
i is 0, 1, 2, 3, 4 or 5;
j is 0, 1, 2, 3, 4 or 5;

a plurality of $R^1$ are mutually the same or different when a is 2 or more;
a plurality of $R^2$ are mutually the same or different when b is 2 or more;
a plurality of $R^3$ are mutually the same or different when c is 2 or more;
a plurality of $R^4$ are mutually the same or different when d is 2 or more;
a plurality of $R^9$ are mutually the same or different when i is 2 or more;
a plurality of $R^{10}$ are mutually the same or different when j is 2 or more;

$B^1$ and $B^2$ each independently represent a substituent represented by a formula (4) below;

m is 0 or 1;
n is 0 or 1; and
m+n=1,

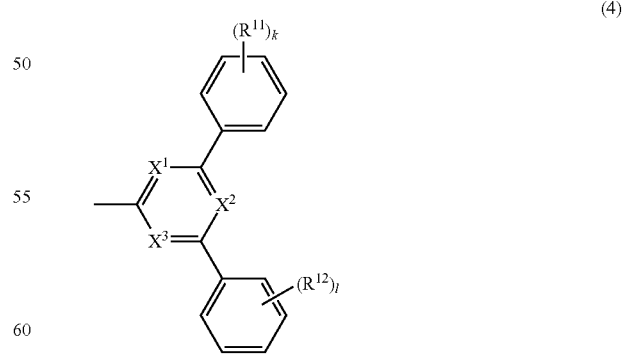

(4)

where: $X^1$ to $X^3$ each independently represent $CR^Z$ or a nitrogen atom;

$R^Z$ represents a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group;

a plurality of $R^Z$ are mutually the same or different;

$R^{11}$ and $R^{12}$ each independently represent a halogen atom, a substituted or unsubstituted alkyl group having 1 to 25 carbon atoms, a substituted or unsubstituted cycloalkyl group having 3 to 25 ring carbon atoms, or a cyano group;

k is 0, 1, 2, 3, 4 or 5;

l is 0, 1, 2, 3, 4 or 5;

a plurality of $R^{11}$ are mutually the same or different when k is 2 or more; and a plurality of $R^{12}$ are mutually the same or different when l is 2 or more.

4. The composition according to claim 3, wherein a, b, c, d, i and j are 0.

5. The composition according to claim 3, wherein $X^1$, $X^2$ and $X^3$ are nitrogen atoms in the formula (4).

6. The composition according to claim 3, wherein m is 1 and n is 0.

7. An organic-electroluminescence-device material comprising the composition according to claim 1.

8. A composition film comprising the composition according to claim 1.

9. An organic electroluminescence device, comprising:
an anode;
a cathode; and
at least one organic layer provided between the anode and the cathode, wherein
the at least one organic layer comprises the composition according to claim 1.

10. The organic electroluminescence device according to claim 9, wherein
the at least one organic layer comprises a plurality of organic layers, and
one of the plurality of organic layers comprises the composition.

11. The organic electroluminescence device according to claim 9, wherein
the at least one organic layer comprises an emitting layer, the emitting layer comprises the composition.

12. The organic electroluminescence device according to claim 11, wherein
the emitting layer further comprises a luminescent material.

13. The organic electroluminescence device according to claim 12, wherein
the emitting layer comprises a phosphorescent material as the luminescent material, and
the phosphorescent material is an ortho-metalated complex of a metal atom selected from the group consisting of iridium, osmium and platinum.

14. The organic electroluminescence device according to claim 11, further comprising:
a hole transporting layer between the anode and the emitting layer.

15. The organic electroluminescence device according to claim 11, further comprising:
an electron transporting layer between the cathode and the emitting layer.

16. An organic electroluminescence device, comprising:
an anode;
a cathode;
an emitting layer provided between the anode and the cathode; and
an electron transporting zone provided between the emitting layer and the cathode, wherein
the electron transporting zone comprises a composition comprising: a mixture of at least two compounds,
the at least two compounds comprising a first compound represented by a formula (1) and a second compound represented by a formula (2) below,

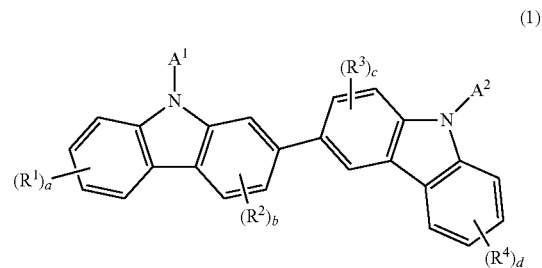

(1)

where: $R^1$ to $R^4$ each independently represent a halogen atom, a substituted or unsubstituted alkyl group having 1 to 25 carbon atoms, a substituted or unsubstituted cycloalkyl group having 3 to 25 ring carbon atoms, a substituted or unsubstituted aryl group having 6 to 18 ring carbon atoms, a substituted or unsubstituted heterocyclic group having 6 to 18 ring atoms, a silyl group substituted by at least one group selected from the group consisting of an alkyl group having 1 to 25 carbon atoms and an aryl group having 6 to 18 ring carbon atoms, or a cyano group;

a is 0, 1, 2, 3 or 4;

b is 0, 1, 2 or 3;

c is 0, 1, 2 or 3;

d is 0, 1, 2, 3 or 4;

a plurality of $R^1$ are mutually the same or different when a is 2 or more;

a plurality of $R^2$ are mutually the same or different when b is 2 or more;

a plurality of $R^3$ are mutually the same or different when c is 2 or more;

a plurality of $R^4$ are mutually the same or different when d is 2 or more;

$A^1$ and $A^2$ each independently represent a substituted or unsubstituted aryl group having 6 to 24 ring carbon atoms, or a substituted or unsubstituted heterocyclic group having 6 to 24 ring atoms; and $R^1$ to $R^4$, $A^1$ and $A^2$ comprise five cyclic structures in total each represented by a formula (1a) below,

(1a)

where: $X^1$, $X^2$ and $X^3$ each independently represent $CR^X$ or a nitrogen atom; in at least one cyclic structure of the five cyclic structures each represented by the formula (1a), at least one of $X^1$, $X^2$ and $X^3$ is a nitrogen atom; the cyclic structures each represented by the formula (1a) are bonded to each other to form a fused ring, or are not bonded;

$R^X$, $R^{X1}$, $R^{X2}$ and $R^{X3}$ each independently represent a single bond, a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group;

when a plurality of $R^X$ are present, the plurality of Rx are mutually the same or different; and at least one of $R^{X1}$, $R^{X2}$, $R^{X3}$ and one or more $R^X$ is a single bond,

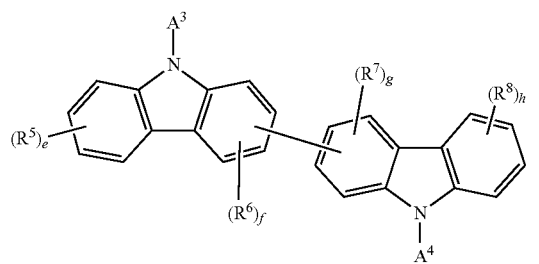

(2)

where: $R^5$ to $R^8$ each independently represent: a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group;

e is 0, 1, 2, 3 or 4;

f is 0, 1, 2 or 3;

g is 0, 1, 2 or 3;

h is 0, 1, 2, 3 or 4;

a plurality of $R^5$ are mutually the same or different when e is 2 or more;

a plurality of $R^6$ are mutually the same or different when f is 2 or more;

a plurality of $R^7$ are mutually the same or different when g is 2 or more;

a plurality of $R^8$ are mutually the same or different when h is 2 or more; and one of $A^3$ and $A^4$ is a substituent represented by a formula (2a), and the other of $A^3$ and $A^4$ is represented by a formula (2b), —Ar—CN (2a)

where: Ar represents a substituted or unsubstituted phenanthrylene group,

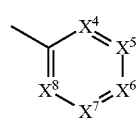

(2b)

where: $X^4$, $X^5$, $X^6$, $X^7$ and $X^8$ each independently represent $CR^Y$ or a nitrogen atom;

$R^Y$ represents a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group; and a plurality of $R^Y$ are mutually the same or different.

17. An electronic device comprising the organic electroluminescence device according to claim 9.

18. The organic electroluminescence device according claim 16, wherein a, b, c and d are 0.

19. The organic electroluminescence device according claim 16, wherein
the first compound is a compound represented by a formula (3) below,

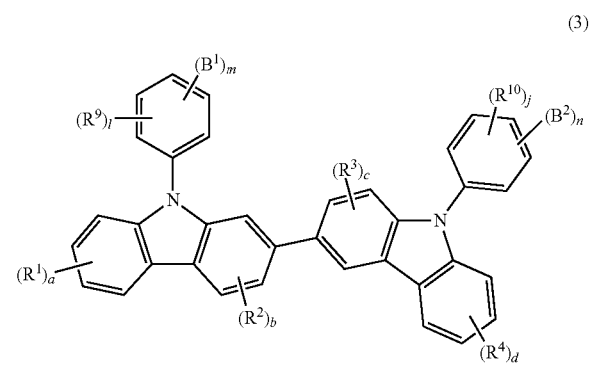

(3)

where: $R^1$ to $R^4$, $R^9$ and $R^{10}$ each independently represent a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group;

a is 0, 1, 2, 3 or 4;

b is 0, 1, 2 or 3;

c is 0, 1, 2 or 3;

d is 0, 1, 2, 3 or 4;

i is 0, 1, 2, 3, 4 or 5;

j is 0, 1, 2, 3, 4 or 5;

a plurality of $R^1$ are mutually the same or different when a is 2 or more;

a plurality of $R^2$ are mutually the same or different when b is 2 or more;

a plurality of $R^3$ are mutually the same or different when c is 2 or more;

a plurality of $R^4$ are mutually the same or different when d is 2 or more;

a plurality of $R^5$ are mutually the same or different when i is 2 or more;

a plurality of $R^{10}$ are mutually the same or different when j is 2 or more;

$B^1$ and $B^2$ each independently represent a substituent represented by a formula (4) below;

m is 0 or 1;

n is 0 or 1; and m+n=1,

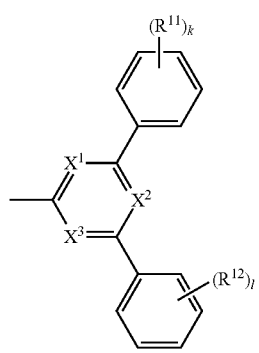

(4)

where: $X^1$ to $X^3$ each independently represent $CR^Z$ or a nitrogen atom;

$R^Z$ represents a hydrogen atom, a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group;

a plurality of $R^Z$ are mutually the same or different;

$R^{11}$ and $R^{12}$ each independently represent a halogen atom, a substituted or unsubstituted alkyl group having 1 to 25 carbon atoms, a substituted or unsubstituted cycloalkyl group having 3 to 25 ring carbon atoms, or a cyano group;

k is 0, 1, 2, 3, 4 or 5;

l is 0, 1, 2, 3, 4 or 5;

a plurality of $R^{11}$ are mutually the same or different when k is 2 or more; and a plurality of $R^{12}$ are mutually the same or different when l is 2 or more.

20. The organic electroluminescence device according claim 19, wherein a, b, c, d, i and j are 0.

21. The organic electroluminescence device according claim 19, wherein $X^1$, $X^2$ and $X^3$ are nitrogen atoms in the formula (4).

22. The organic electroluminescence device according claim 19, wherein m is 1 and n is 0.

23. The organic electroluminescence device according claim 16, wherein the second compound is a compound represented by a formula (5) below,

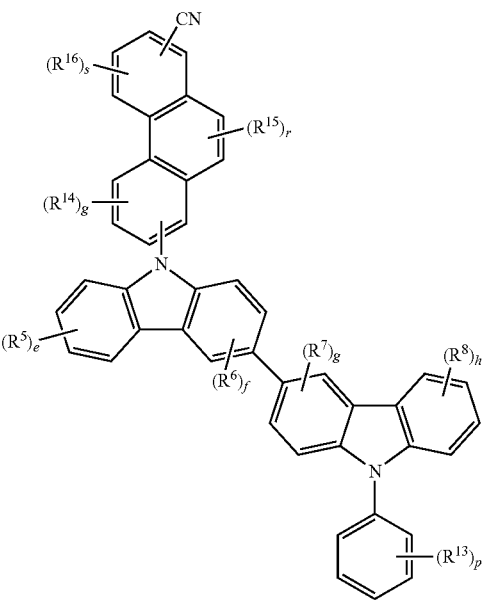

(5)

where: $R^5$ to $R^8$ and $R^{13}$ to $R^{16}$ each independently represent: a halogen atom, a substituted or unsubstituted alkyl group having 1 to 25 carbon atoms, a substituted or unsubstituted cycloalkyl group having 3 to 25 ring carbon atoms, a silyl group substituted by an alkyl group having 1 to 25 carbon atoms, or a cyano group;

e is 0, 1, 2, 3 or 4;

f is 0, 1, 2 or 3;

g is 0, 1, 2 or 3;

h is 0, 1, 2, 3 or 4;

p is 0, 1, 2, 3, 4 or 5;

q is 0, 1, 2 or 3;

r is 0, 1 or 2;

s is 0, 1, 2 or 3;

a plurality of $R^5$ are mutually the same or different when e is 2 or more;

a plurality of $R^6$ are mutually the same or different when f is 2 or more;

a plurality of $R^7$ are mutually the same or different when g is 2 or more;

a plurality of $R^8$ are mutually the same or different when h is 2 or more;

a plurality of $R^{13}$ are mutually the same or different when p is 2 or more;

a plurality of $R^{14}$ are mutually the same or different when q is 2 or more;

a plurality of $R^{15}$ are mutually the same or different when r is 2 or more; and a plurality of $R^{16}$ are mutually the same or different when s is 2 or more.

24. The organic electroluminescence device according claim 23, wherein e, f, g, h, p, q, r and s are 0.

25. The organic electroluminescence device according claim 16, wherein the emitting layer comprises a phosphorescent material as a luminescent material, and the phosphorescent material is an ortho-metalated complex of a metal atom selected from the group consisting of iridium, osmium and platinum.

26. The organic electroluminescence device according claim 16, further comprising: a hole transporting layer between the anode and the emitting layer.

27. The organic electroluminescence device according claim 16, further comprising: an electron transporting layer between the cathode and the emitting layer.

28. An electronic device comprising the organic electroluminescence device according to claim 16.

* * * * *